(12) United States Patent
Holstein et al.

(10) Patent No.: US 10,105,419 B2
(45) Date of Patent: Oct. 23, 2018

(54) DIETARY SUPPLEMENTS AND FORMULATIONS

(71) Applicant: Eastern Vision Limited, Wanchai (HK)

(72) Inventors: Michael Holstein, Clearwater, FL (US); Eric Huntington, Clearwater, FL (US)

(73) Assignee: Eastern Vision Limited, Wanchai (HK)

( * ) Notice: Subject to any disclaimer, the term of this patent is extended or adjusted under 35 U.S.C. 154(b) by 97 days.

(21) Appl. No.: 15/240,859

(22) Filed: Aug. 18, 2016

(65) Prior Publication Data

US 2017/0000856 A1 Jan. 5, 2017

Related U.S. Application Data

(62) Division of application No. 14/662,143, filed on Mar. 18, 2015, now Pat. No. 9,446,100.

(Continued)

(51) Int. Cl.

| | |
|---|---|
| *A61K 38/44* | (2006.01) |
| *A61K 33/06* | (2006.01) |
| *A61K 38/06* | (2006.01) |
| *A61K 31/385* | (2006.01) |
| *A61K 38/54* | (2006.01) |
| *A61K 31/197* | (2006.01) |
| *A61K 31/4188* | (2006.01) |
| *A61K 31/59* | (2006.01) |
| *A61K 36/42* | (2006.01) |
| *A61K 36/24* | (2006.01) |
| *A61K 36/81* | (2006.01) |
| *A61K 36/53* | (2006.01) |
| *A61K 36/41* | (2006.01) |
| *A61K 31/685* | (2006.01) |
| *A61K 31/122* | (2006.01) |
| *A61K 35/60* | (2006.01) |
| *A61K 33/24* | (2006.01) |
| *A61K 31/202* | (2006.01) |
| *A61K 36/88* | (2006.01) |

(Continued)

(52) U.S. Cl.
CPC .......... *A61K 38/446* (2013.01); *A61K 31/047* (2013.01); *A61K 31/07* (2013.01); *A61K 31/10* (2013.01); *A61K 31/12* (2013.01); *A61K 31/122* (2013.01); *A61K 31/14* (2013.01); *A61K 31/145* (2013.01); *A61K 31/16* (2013.01); *A61K 31/185* (2013.01); *A61K 31/19* (2013.01); *A61K 31/197* (2013.01); *A61K 31/198* (2013.01); *A61K 31/202* (2013.01); *A61K 31/205* (2013.01); *A61K 31/25* (2013.01); *A61K 31/352* (2013.01); *A61K 31/355* (2013.01); *A61K 31/375* (2013.01); *A61K 31/385* (2013.01); *A61K 31/4188* (2013.01); *A61K 31/4415* (2013.01); *A61K 31/455* (2013.01); *A61K 31/519* (2013.01); *A61K 31/525* (2013.01); *A61K 31/59* (2013.01); *A61K 31/592* (2013.01); *A61K 31/593* (2013.01); *A61K 31/685* (2013.01); *A61K 31/7048* (2013.01); *A61K 31/7076* (2013.01); *A61K 31/714* (2013.01); *A61K 31/733* (2013.01); *A61K 33/04* (2013.01); *A61K 33/06* (2013.01); *A61K 33/24* (2013.01); *A61K 33/30* (2013.01); *A61K 33/34* (2013.01); *A61K 33/42* (2013.01); *A61K 35/60* (2013.01); *A61K 36/068* (2013.01); *A61K 36/185* (2013.01); *A61K 36/24* (2013.01); *A61K 36/41* (2013.01); *A61K 36/42* (2013.01); *A61K 36/53* (2013.01); *A61K 36/81* (2013.01); *A61K 36/88* (2013.01); *A61K 38/063* (2013.01); *A61K 38/168* (2013.01); *A61K 38/465* (2013.01); *A61K 38/47* (2013.01); *A61K 38/4873* (2013.01); *A61K 38/54* (2013.01); *A61K 45/06* (2013.01); *C12Y 115/01001* (2013.01)

(58) Field of Classification Search
None
See application file for complete search history.

(56) References Cited

U.S. PATENT DOCUMENTS

| | | | |
|---|---|---|---|
| 5,569,458 | A | 10/1996 | Greenberg |
| 6,759,061 | B2 | 7/2004 | Watson et al. |

(Continued)

FOREIGN PATENT DOCUMENTS

| | | |
|---|---|---|
| CA | 2484691 A1 | 5/2006 |
| EP | 1537865 A1 | 6/2005 |

(Continued)

OTHER PUBLICATIONS

Anderson et al. Elevated intakes of supplemental chromium improve glucose and insulin variables in individuals with type 2 diabetes. Diabetes 46:1786-1791 (1997).

(Continued)

*Primary Examiner* — Sharmila G Landau
*Assistant Examiner* — Stephen M Chong
(74) *Attorney, Agent, or Firm* — Paul Murty; Nicholas Pfeifer; Smith & Hopen, P.A.

(57) ABSTRACT

Provided are dietary supplements, formulations, kits and methods for administration to an individual with type II diabetes or at risk of developing type II diabetes. Provided herein are formulations, kits and methods useful for treating, preventing, supporting, controlling, restoring, and/or maintaining blood sugar levels in individuals with type II diabetes or at risk of developing the same. Also provided are formulations, kits and methods useful for reducing and/or eliminating requirement of ex-vivo insulin administration in an individual diagnosed with type II diabetes.

12 Claims, 4 Drawing Sheets

Related U.S. Application Data

(60) Provisional application No. 62/116,315, filed on Feb. 13, 2015.

(51) Int. Cl.

| | | |
|---|---|---|
| *A61K 45/06* | (2006.01) | |
| *A61K 31/07* | (2006.01) | |
| *A61K 31/10* | (2006.01) | |
| *A61K 31/12* | (2006.01) | |
| *A61K 31/14* | (2006.01) | |
| *A61K 31/185* | (2006.01) | |
| *A61K 31/198* | (2006.01) | |
| *A61K 31/205* | (2006.01) | |
| *A61K 31/25* | (2006.01) | |
| *A61K 31/352* | (2006.01) | |
| *A61K 31/355* | (2006.01) | |
| *A61K 31/375* | (2006.01) | |
| *A61K 31/4415* | (2006.01) | |
| *A61K 31/455* | (2006.01) | |
| *A61K 31/519* | (2006.01) | |
| *A61K 31/525* | (2006.01) | |
| *A61K 31/592* | (2006.01) | |
| *A61K 31/593* | (2006.01) | |
| *A61K 31/7048* | (2006.01) | |
| *A61K 31/7076* | (2006.01) | |
| *A61K 31/714* | (2006.01) | |
| *A61K 31/733* | (2006.01) | |
| *A61K 33/04* | (2006.01) | |
| *A61K 33/30* | (2006.01) | |
| *A61K 33/34* | (2006.01) | |
| *A61K 33/42* | (2006.01) | |
| *A61K 38/16* | (2006.01) | |
| *A61K 38/46* | (2006.01) | |
| *A61K 38/47* | (2006.01) | |
| *A61K 38/48* | (2006.01) | |
| *A61K 36/068* | (2006.01) | |
| *A61K 31/047* | (2006.01) | |
| *A61K 31/145* | (2006.01) | |
| *A61K 31/16* | (2006.01) | |
| *A61K 31/19* | (2006.01) | |
| *A61K 36/185* | (2006.01) | |

(56) References Cited

U.S. PATENT DOCUMENTS

| | | | |
|---|---|---|---|
| 7,923,044 B2 | 4/2011 | Bias | |
| 8,017,147 B2 | 9/2011 | Mazed et al. | |
| 8,343,517 B1 | 1/2013 | Bezzek | |
| 8,877,239 B2 | 11/2014 | Settineri et al. | |
| 8,883,205 B2 | 11/2014 | Roehr et al. | |
| 2003/0008048 A1 | 1/2003 | Winston et al. | |
| 2004/0175439 A1 | 9/2004 | Cyr | |
| 2006/0134300 A1 | 6/2006 | Newman | |
| 2006/0189512 A1 | 8/2006 | Ehrenkranz | |
| 2006/0228426 A1 | 10/2006 | Cyr | |
| 2007/0009576 A1 | 1/2007 | Stillman | |
| 2007/0065456 A1 | 3/2007 | Woods | |
| 2007/0166411 A1 | 7/2007 | Anthony et al. | |
| 2007/0190114 A1 | 8/2007 | Smart | |
| 2007/0202215 A1 | 8/2007 | Lak | |
| 2007/0218170 A1 | 9/2007 | Kendrick | |
| 2008/0268042 A1 | 10/2008 | Feuerstein et al. | |
| 2009/0232916 A1 | 9/2009 | Shulman et al. | |
| 2009/0252796 A1 | 10/2009 | Mazed et al. | |
| 2010/0074969 A1 | 3/2010 | Hughes et al. | |
| 2010/0323041 A1 | 12/2010 | Cyr | |
| 2011/0097427 A1 | 4/2011 | Ramakrishnan et al. | |
| 2011/0300081 A1 | 12/2011 | Seneci | |
| 2012/0177730 A1 | 7/2012 | Baron et al. | |
| 2013/0203664 A1 | 8/2013 | Bolster et al. | |
| 2014/0017337 A1 | 1/2014 | Amoruso | |
| 2014/0335061 A1 | 11/2014 | Tripp et al. | |
| 2016/0235822 A1 | 8/2016 | Holstein et al. | |

FOREIGN PATENT DOCUMENTS

| | | |
|---|---|---|
| EP | 2184069 A1 | 5/2010 |
| IN | 2011DE03821 | 12/2014 |
| RU | 2274400 C1 | 4/2006 |
| RU | 2007121946 A | 12/2008 |
| WO | WO-9961038 A1 | 12/1999 |
| WO | WO-2010051792 A1 | 5/2010 |
| WO | WO-2010146601 A1 | 12/2010 |
| WO | WO-2012143860 A1 | 10/2012 |
| WO | WO-2014179341 A1 | 11/2014 |

OTHER PUBLICATIONS

Boden et al. Effects of vanadyl sulfate on carbohydrate and lipid metabolism in patients with non-insulin dependent diabetes mellitus. Metabolism 45:1130-1135 (1996).

Cohen et al. Oral vanadyl sulfate improves hepatic and peripheral insulin insensitivity in patients with non-insulin dependent diabetes mellitus. J Clin Invest. 95:2501-2509 (1995).

French et al. Role of vanadium in nutrition: metabolism, essential and dietary considerations. Life Sciences. 52:339-346 (1992).

Goldfine et al. Metabolic effects of sodium metavandate in humans with insulin-dependent and noninsulin-dependent diabetes mellitus in vivo and vitro studies. J Clin Endo and Meta 80(11):3311-3331 (1995).

Halberstam et al. Oral vanadyl sulfate improves insulin sensitivity NIDOM but not in obese nondiabetic subjects. Diabetes. 45:659-665 (1996).

Jacob et al. Enhancement of glucose disposal in patients with Type 2 diabetes by alpha-lipoic acid. Arzneim-Rosch Drug Res 45(2):872-874(1995).

Jacob et al. The antioxidant alpha-lipoic acid enhances insulin-stimulated glucose metabolism in insulin resistant rate skeletal muscle. Diabetes 45:1024-1029 (1996).

Konard et al. Alpha-lipoic acid treatment decreases serum actate and pyruvate concentrations and improves glucose effectiveness in lean and obese patients with type 2 diabetes. Diabetes Care 22:4280-4287 (1999).

Levine et al. Effect of oral chromium supplementation on the glucose tolerance of elderly human subjects. Metabolism 17:114-125 (1968).

Shechter et al. Insulin-like actions of vanadate are mediated in an insulin receptor independent manner via non-receptor protein tyrosine kinases and protein phospholyrisine phosphates. Mol Cell Biochem. 153(1-2):39-47 (1995).

Streeper et al. Differential effects of lipoic acid stereo-isomers on glucose metabolism in insulin resistant skeletal muscle. Am J Physiol 273:E185-E191 (1997).

U.S. Appl. No. 14/662,143 Office Action dated Mar. 25, 2016.

U.S. Appl. No. 14/662,143 Office Action dated Sep. 2, 2015.

Zhang et al. A high biotin diet improves the impaired glucose tolerance of long-term spontaneously hyperglycemic rats with non-insulin dependent diabetes mellitus. J Nutr Sci Vitamin 42:517-526 (1996).

Results of Statistical Patient Survey (151 cases)

Average reduction of A1C = 18%

- 84% of type II diabetics reduced their oral medication
- 74% of type II diabetics got off ALL oral blood sugar
- 100% of type II diabetics reduced their insulin dosage
- 50% got off ALL insulin
- 24 lbs. of weight loss
- 45% of type II diabetics become NON-DIABETIC!!!

Figure 2

DIETARY SUPPLEMENTS AND FORMULATIONS

CROSS-REFERENCE TO RELATED APPLICATIONS

This application is a divisional application of U.S. application Ser. No. 14/662,143, filed Mar. 18, 2015, which claims the benefit of U.S. Provisional Application No. 62/116,315, filed Feb. 13, 2015, each of which are incorporated by reference herein in their entirety.

BACKGROUND

Diabetes mellitus (DM), commonly referred to as diabetes, is a group of conditions characterized by high blood sugar levels presented in a patient potentially over a prolonged duration of time. Type II diabetes is a form of diabetes that is generally associated with insulin resistance, a condition in which cells fail to respond to insulin properly. As the disease progresses, a lack of insulin may also develop. Type II diabetes was previously referred to as "non-insulin-dependent diabetes mellitus" (NIDDM) or "adult-onset diabetes."

Disclosed herein are dietary supplements, formulations and methods useful for treating, preventing, supporting, controlling, restoring, and/or maintaining blood sugar levels in individuals suffering from pre-diabetic conditions and/or diabetes. The formulations of dietary supplements and methods of use thereof disclosed herein are also useful for treating, preventing, supporting, controlling, restoring, and/or maintaining blood sugar levels in an individual or a patient or for support or treatment of other physiological conditions generally associated with type II diabetes.

SUMMARY

An object of the present disclosure is to provide dietary supplements, formulations, kits and methods for administration to an individual with type II diabetes, an individual who is at risk of developing type II diabetes, or to a healthy individual that desires to avoid developing diabetes. Provided herein are formulations, kits and methods useful for treating, preventing, supporting, controlling, restoring, or maintaining blood sugar levels in individuals with type II diabetes or at risk of developing the same. Also provided are formulations, kits and methods useful for reducing and/or eliminating requirement of ex-vivo insulin administration in an individual diagnosed with type II diabetes.

In one aspect, provided herein is a formulation comprising:
 a) group A components consisting essentially of one or more protein;
 b) at least one group B component that comprises dandelion extract, milk thistle extract, phospholipids, ginger, taurine, turmeric extract, vitamin C, methionine or combinations thereof;
 c) at least one group C component that comprises magnesium, trimethylglycine, glutathione, N-acetyl-cysteine, *Cordyceps sinensis* extract, glutamine, alpha lipoic acid, glycine or combinations thereof; and
 d) an excipient.

Also provided herein is a formulation comprising: group A components consisting essentially of protein selected from the group consisting of pea protein isolate, sacha inchi protein, hemp protein, rice protein, artichoke protein, chia seed protein, beef protein or combinations thereof; at least one group B component that comprises dandelion extract, milk thistle extract, phospholipids, ginger, taurine, turmeric extract, vitamin C, methionine or combinations thereof; at least one group C component that comprises magnesium, trimethylglycine, glutathione, N-acetyl-cysteine, glutamine, alpha lipoic acid, glycine or combinations thereof; at least one group D component that comprises hesperidin, beet root, enzyme blend, sarsparilla root, bromelain, betaine, methylsulfonylmethane (MSM), choline bitartarate, primrose, inulin, watercress leaf, *Panax ginseng* root extract, selenium, lecithin, or S-anenosylmethionine (SAM-e), thiamine, vitamin B5, niacin, vitamin E, riboflavin, vitamin B6, folate, vitamin B12, biotin, zinc, copper, molybdenum, carotene, calcium, vitamin D, sodium phosphate, vitamin A, calcium, phosphorus, chromium, triglyceride, quercetin, rutin, Marshmallow extract, Jerusalem artichoke tuber, fiber or combinations thereof; and an excipient. In some embodiments, the enzyme blend comprises a lactase, a cellulase, a protease, a lipase, a dismutase, a catalase, or a combination thereof.

Provided herein are formulations useful for treatment and/or stabilization of individuals suffering from type II diabetes or at risk of developing type II diabetes. In some embodiments, provided is a formulation comprising: group A components consisting essentially of protein selected from pea protein isolate, sacha inchi protein, hemp protein, rice protein, artichoke protein, chia seed protein, beef protein or combinations thereof; at least one group B component that comprises dandelion extract, milk thistle extract, phospholipids, ginger, taurine, turmeric extract, vitamin C, methionine or combinations thereof; at least one group C component that comprises magnesium, trimethylglycine, glutathione, N-acetyl-cysteine, *Cordyceps sinensis* extract, glutamine, alpha lipoic acid, glycine or combinations thereof; and an excipient. In some embodiments, the formulation further comprises pea protein isolate and sacha inchi protein. In some embodiments, the formulation further comprises a protein derived from a source which is not pea protein isolate. In some embodiments, the formulation further comprises a protein derived from a source which is not sacha inchi protein.

Further provided is a formulation comprising: group A components consisting essentially of maca, *Cornus officinalis* fruit extract or combinations thereof; at least one group B component that comprises berberine, bitter melon extract, *Gymnema sylvestre* leaf extract, banaba, carnitine or combinations thereof; at least one group C component that comprises vitamin C, *Panax ginseng* root extract, Aswagandha root extract, holy basil leaf extract, *Rhodiola rosea* extract, *Eleutherococcus senticosus* extract, vitamin B5, cactus stem extract, phosphatidylserine, vitamin D or combinations thereof; and an excipient. In some embodiments, the formulation further comprises a fish oil formulation. The fish oil formulation may comprise omega-3 at a range of about 15% to about 100%.

Also provided is a formulation comprising: group A components consisting essentially of maca, *Cornus officinalis* fruit extract or combinations thereof; at least one group B component that comprises berberine, bitter melon extract, *Gymnema sylvestre* leaf extract, banaba, or carnitine; at least one group C component that comprises vitamin C, *Panax ginseng* root extract, Aswagandha root extract, holy basil leaf extract, *Rhodiola rosea* extract, *Eleutherococcus senticosus* extract, vitamin B5, cactus stem extract, phosphatidylserine, vitamin D or combinatins thereof; at least one group D component that comprises *Cordyceps sinesis* extract, *Gingko biloba* leaf extract, suma root, *Garcinia*

*cambogia* extract, *Rehmannia glutinosa* extract, *Poria cocos* root extract, cinnamon extract, Fenugreek, Guggul, citrimax extract, *salacia oblonga* extract, vitamin E, thiamin, riboflavin, niacin, vitamin B6, folate, vitamin B12, biotin, magnesium, zinc, selenium, manganese, chromium, vanadium, zinc, biotin, alpha lipoic acid, N-acetyl-cysteine, 4-aminobenzoic acid (PABA), choline bitartrate, glutamine, glutathione, protein, fiber, inositol or combinations thereof; and an excipient.

Still further provided is a formulation comprising: group A components consisting essentially of cactus stem extract; at least one group B component that comprises berberine, bitter melon extract, *Gymnema sylvestre* leaf extract, banaba, carnitine or combinations thereof; at least one group C component that comprises *Garcinia cambogia* extract, *Rehmannia glutinosa* extract, *Poria cocos* root extract, cinnamon extract, Fenugreek, Guggul, Vitamin D or combinations thereof; and an excipient.

Additionally provided is a formulation comprising: group A component comprising cactus stem extract; at least one of group B component that comprises berberine, bitter melon extract, *Gymnema sylvestre* leaf extract, banaba, carnitine or combinations thereof; at least one group C component that comprises *Garcinia cambogia* extract, *Rehmannia glutinosa* extract, *Poria cocos* root extract, cinnamon extract, Fenugreek, or Guggul; at least one group D component that comprises vitamin D, vitamin E, thiamin, riboflavin, niacin, vitamin B6, folate, vitamin B12, biotin, vitamin B5, magnesium, zinc, selenium, manganese, chromium, vanadium, alpha lipoic acid, N-acetyl-cysteine, 4-aminobenzoic acid (PABA), choline bitartarate, citrimax extract, taurine, coenzyme Q10, calcium, vitamin K2, vitamin C, protein, fiber, inositol or combinations thereof; and an excipient.

In some embodiments is a formulation described herein, wherein dandelion extract is dandelion root extract. In some embodiments is a formulation described herein, wherein the phospholipids comprise about 40% phosphatidylcholine. In some embodiments is a formulation described herein, wherein the turmeric extract comprises about 95% curcumin. In some embodiments is a formulation described herein, wherein milk thistle extract is milk thistle seed extract comprises about 80% silymarin. In some embodiments is a formulation described herein, optionally further comprising a gotu kola extract, which is optionally a gotu kola leaf extract. In some embodiments is a formulation described herein, wherein vitamin C comprises L-ascorbic acid, calcium ascorbate, or a combination thereof. In some embodiments is a formulation described herein, wherein magnesium is magnesium citrate. In some embodiments is a formulation described herein, wherein glutathione comprises L-glutathione, S-acetyl L-glutathione, or a combination thereof. In some embodiments is a formulation described herein, wherein N-acetyl-cysteine is N-Acetyl L-cysteine. In some embodiments is a formulation described herein, wherein *Cordyceps sinensis* extract comprises about 7% cordycepic acid. In some embodiments is a formulation described herein, wherein glutamine is L-glutamine. In some embodiments is a formulation described herein, wherein alpha lipoic acid is alpha R-lipoic acid. In some embodiments is a formulation described herein, wherein glycine is L-glycine. In some embodiments is a formulation described herein, further comprising at least one group D component that comprises hesperidin, beet root, enzyme blend, sarsaparilla root, bromelain, betaine, methylsulfonylmethane (MSM), choline bitartarate, luo han guo, *stevia* extract rebaudioside, primrose, inulin, watercress leaf, *Panax ginseng* root extract, selenium, or S-anenosylmethionine (SAM-e). In some embodiments is a formulation described herein, wherein luo han guo comprises about 40% mogrosides. In some embodiments is a formulation described herein, wherein the *stevia* extract rebaudioside is *stevia* extract 97% rebaudioside. In some embodiments is a formulation described herein, wherein the primrose is evening primrose oil powder. In some embodiments is a formulation described herein, wherein hesperidin is hesperidin complex. In some embodiments is a formulation described herein, wherein beet root is beet root powder. In some embodiments is a formulation described herein, wherein the enzyme blend comprises a lactase, a cellulase, a protease, a lipase, a dismutase, a catalase, or a combination thereof. In some embodiments is a formulation described herein, wherein betaine is betaine hydrochloride. In some embodiments is a formulation described herein, wherein choline is choline bitartarate. In some embodiments is a formulation described herein, wherein the watercress leaf is watercress leaf powder. In some embodiments is a formulation described herein, wherein selenium is L-selenomethionine. In some embodiments is a formulation described herein, further comprising at least one group E component that comprises thiamine, vitamin B5, niacin, vitamin E, vitamin B6, folate, vitamin B12, biotin, zinc, copper, molybdenum, carotene, calcium, vitamin D, sodium phosphate, triglyceride, quercetin, rutin, Marshmallow extract, or Jerusalem artichoke tuber.

In some embodiments is a formulation described herein, wherein thiamine is optionally benfotiamine. In some embodiments is a formulation described herein, wherein vitamin B5 comprises at least one of pantothenic acid, pantethine, d-calcium pantothenate, or a combination thereof. In some embodiments is a formulation described herein, wherein niacin comprises at least one of niacinamide, nicotinic acid, or a combination thereof. In some embodiments is a formulation described herein, wherein vitamin E is d-alpha tocopherol succinate. In some embodiments is a formulation described herein, optionally further comprising riboflavin, wherein said riboflavin is optionally riboflavin-5'-phosphate. In some embodiments is a formulation described herein, wherein vitamin B6 comprises at least one of pyridoxal-5-phosphate, pyridoxine HCl, or a combination thereof. In some embodiments is a formulation described herein, wherein folate is L-5-methyltetrahydrofolate.

In some embodiments is a formulation described herein, wherein vitamin B12 is methylcobalamin. In some embodiments is a formulation described herein, wherein zinc is zinc glycinate. In some embodiments is a formulation described herein, wherein copper is copper gluconate. In some embodiments is a formulation described herein, wherein molybdenum is molybdenum amino acid chelate. In some embodiments is a formulation described herein, wherein carotene is beta carotene. In some embodiments is a formulation described herein, wherein calcium is calcium ascorbate. In some embodiments is a formulation described herein, wherein vitamin D is vitamin D3. In some embodiments is a formulation described herein, wherein sodium phosphate is disodium phosphate. In some embodiments is a formulation described herein, wherein the triglyceride is a triglyceride comprising about 6-12 carbon fatty acid esters.

In some embodiments is a formulation described herein, wherein quercetin is quercetin dihydrate. In some embodiments is a formulation described herein, wherein Marshmallow extract is Marshmallow root extract. In some embodiments is a formulation described herein, wherein the concentration of pea protein isolate in the formulation is from about 5% to about 70% by weight. In some embodiments is a formulation described herein, wherein the concentration of sacha inchi protein in the formulation is from about 0.5% to about 10% by weight. In some embodiments is a formulation described herein, wherein the concentration of dandelion extract in the formulation is from about 5% to about 40% by weight. In some embodiments is a formulation described herein, wherein the concentration of milk thistle extract in the formulation is from about 3% to about 15% by weight. In some embodiments is a formulation described herein, wherein the concentration of phospholipids in the formulation is from about 1% to about 12% by weight. In some embodiments is a formulation described herein, wherein the concentration of ginger in the formulation is from about 1% to about 10% by weight. In some embodiments is a formulation described herein, wherein the concentration of taurine in the formulation is from about 0.5% to about 8% by weight.

In some embodiments is a formulation described herein, wherein the concentration of turmeric extract in the formulation is from about 0.5% to about 8% by weight. In some embodiments is a formulation described herein, wherein the optionally comprising gotu kola extract in a concentration up to about 8% by weight. In some embodiments is a formulation described herein, wherein the concentration of vitamin C in the formulation is from about 1% to about 8% by weight. In some embodiments is a formulation described herein, wherein the concentration of methionine in the formulation is from about 1% to about 11% by weight. In some embodiments is a formulation described herein, wherein the concentration of magnesium in the formulation is from about 10% to about 55% by weight. In some embodiments is a formulation described herein, wherein the concentration of trimethylglycine in the formulation is from about 1% to about 40% by weight. In some embodiments is a formulation described herein, wherein the concentration of glutathione in the formulation is from about 0.5% to about 35% by weight. In some embodiments is a formulation described herein, wherein the concentration of N-acetylcysteine in the formulation is from about 0.5% to about 30% by weight. In some embodiments is a formulation described herein, wherein the concentration of *Cordyceps sinensis* extract in the formulation is from about 0.5% to about 6% by weight. In some embodiments is a formulation described herein, wherein the concentration of glutamine in the formulation is from about 0.5% to about 6% by weight. In some embodiments is a formulation described herein, wherein the concentration of alpha lipoic acid in the formulation is from about 0.5% to about 6% by weight. In some embodiments is a formulation described herein, wherein the concentration of glycine in the formulation is from about 0.5% to about 6% by weight.

In some embodiments is a formulation described herein, wherein the excipient comprises gelatin, cellulose, medium-chain triglyceride (MCT) oil, silicon dioxide, stearic acid, xanthan gum, potassium sorbate, turmeric powder, primrose oil, lemon oil, or combinations thereof. In some embodiments is a formulation described herein, wherein the formulation is in a powder form, a semi-solid form, a liquid form, an emulsion form, or a combination thereof.

In some embodiments is a formulation described herein, further comprising at least one component that comprises hesperidin, beet root, enzyme blend, sarsaparilla root, bromelain, betaine, methylsulfonylmethane (MSM), choline bitartarate, luo han guo, *stevia* extract rebaudioside, primrose, inulin, watercress leaf, *Panax ginseng* root extract, selenium, or S-anenosylmethionine (SAM-e). In some embodiments is a formulation described herein, further comprising at least one component that comprises thiamine, vitamin B5, niacin, vitamin E, riboflavin, vitamin B6, folate, vitamin B12, biotin, zinc, copper, molybdenum, carotene, calcium, vitamin D, sodium phosphate, triglyceride, quercetin, rutin, Marshmallow extract, or Jerusalem artichoke tuber. In some embodiments is a formulation described herein, wherein the phospholipids comprise about 40% phosphatidylcholine. In some embodiments is a formulation described herein, wherein the turmeric extract comprises about 95% curcumin. In some embodiments is a formulation described herein, wherein milk thistle extract is milk thistle seed extract comprising about 80% silymarin.

In some embodiments is a formulation described herein, further comprising gotu kola extract, wherein optionally said gotu kola extract is gotu kola leaf extract. In some embodiments is a formulation described herein, wherein vitamin C comprises L-ascorbic acid, calcium ascorbate, or a combination thereof. In some embodiments is a formulation described herein, wherein glutathione comprises L-glutathione, S-acetyl L-glutathione, or a combination thereof. In some embodiments is a formulation described herein, wherein *Cordyceps sinensis* extract comprises about 7% cordycepic acid. In some embodiments is a formulation described herein, wherein luo han guo comprises about 40% mogrosides.

In some embodiments is a formulation described herein, wherein the *stevia* extract rebaudioside is *stevia* extract 97% rebaudioside. In some embodiments is a formulation described herein, wherein the concentration of pea protein isolate in the formulation is from about 5% to about 70% by weight. In some embodiments is a formulation described herein, wherein the concentration of sacha inchi protein in the formulation is from about 0.5% to about 10% by weight.

In an embodiment is a formulation described herein, wherein berberine is berberine hydrochloride. In some embodiments is a formulation described herein, wherein carnitine is carnitine tartrate. In some embodiments is a formulation described herein, wherein carnitine is L-carnitine L-tartrate. In some embodiments is a formulation described herein, wherein the *Cordyceps sinesis* extract is a *Cordyceps sinesis* mycelium extract. In some embodiments is a formulation described herein, wherein vitamin C is L-ascorbic acid. In some embodiments is a formulation described herein, wherein vitamin B5 comprises at least one of pantothenic acid, pantethine, d-calcium pantothenate, or a combination thereof. In some embodiments is a formulation described herein, wherein the phosphatidylserine is a phospholipid complex supplement. In an embodiment is a formulation described herein, wherein vitamin D is a powder. In some embodiments is a formulation described herein, further comprising at least one component that comprises *Cordyceps sinesis* extract, *Gingko biloba* leaf extract, suma root, *Garcinia cambogia* extract, *Rehmannia glutinosa* extract, *Poria cocos* root extract, cinnamon extract, Fenugreek, or Guggul.

In some embodiments is a formulation described herein, wherein *Rehmannia glutinosa* extract is *Rehmania glutinosa* rhizome extract. In some embodiments is a formulation described herein, wherein the *Rehmania glutinosa* rhizome extract is a *Rehmania glutinosa* rhizome 5:1 extract.

In some embodiments is a formulation described herein, further comprising a fish oil formulation. In some embodiments is a formulation described herein, wherein the fish oil formulation comprises omega-3 at a range of about 15% to about 100%. In some embodiments is a formulation described herein, wherein the fish oil formulation comprises eicosapentaenoic acid (EPA) at a range of about 5% to about 100%. In some embodiments the fish oil formulation comprises docosahexaenoic acid (DHA) at a range of about 10% to about 100%. In some embodiments is a formulation described herein, wherein the fish oil formulation is in a powder form. In some embodiments is a formulation described herein, wherein the fish oil formulation is in a liquid form. In some embodiments is a formulation described herein, wherein the fish oil formulation is in an emulsion form. In some embodiments is a formulation described herein, wherein the fish oil formulation further comprises one or more of citric acid, luo han guo, sodium citrate, calcium glycinate amino acid complex, magnesium glycinate, zinc glycinate chelate, zinc L-monomethionine, pyridoxal-5-phosphate drum, niacin, molybdenum amino acid chelate, taurine, lecithin, glycerine, and vitamin E.

In some embodiments is a formulation described herein, further comprising at least one component that comprises one or more of vitamin E, thiamin, riboflavin, niacin, vitamin B6, folate, vitamin B12, biotin, magnesium, zinc, selenium, manganese, chromium, vanadium, alpha lipoic acid, N-acetyl-cysteine, 4-aminobenzoic acid (PABA), choline bitartrate, or inositol. In some embodiments is a formulation described herein, wherein the concentration of berberine hydrochloride in the formulation is from about 6% to about 28% by weight. In some embodiments is a formulation described herein, wherein the concentration of bitter melon extract in the formulation is from about 0.2% to about 18% by weight. In some embodiments is a formulation described herein, wherein the concentration of *Gymnema sylvestre* leaf extract in the formulation is from about 8% to about 18% by weight. In some embodiments is a formulation described herein, wherein the concentration of banaba in the formulation is from about 0.2% to about 18% by weight. In some embodiments is a formulation described herein, wherein the concentration of cactus stem extract in the formulation is from about 1% to about 8% by weight. In some embodiments is a formulation described herein, wherein the concentration of L-carnitine L-tartrate in the formulation is from about 1% to about 5% by weight. In some embodiments is a formulation described herein, wherein the concentration of *Garcinia cambogia* extract in the formulation is from about 0.1% to about 1% by weight. In some embodiments is a formulation described herein, wherein the concentration of *Rehmannia glutinosa* extract in the formulation is from about 0.1% to about 3% by weight. In some embodiments is a formulation described herein, wherein the concentration of *Poria cocos* root extract in the formulation is from about 0.1% to about 1% by weight. In some embodiments is a formulation described herein, wherein the concentration of cinnamon extract in the formulation is from about 0.1% to about 1% by weight. In some embodiments is a formulation described herein, wherein the concentration of Fenugreek extract in the formulation is from about 0.1% to about 1% by weight.

In some embodiments is a formulation described herein, wherein the concentration of Guggul extract in the formulation is from about 0.1% to about 1% by weight. In some embodiments is a formulation described herein, optionally comprising broad bean extract which is optionally in a concentration from about 0.05% to about 0.25% by weight. In some embodiments is a formulation described herein, wherein the concentration of *Cordyceps sinesis* extract in the formulation is from about 0.5% to about 3% by weight. In some embodiments is a formulation described herein, wherein the concentration of maca in the formulation is from about 0.5% to about 3% by weight. In some embodiments is a formulation described herein, wherein the concentration of *Gingko biloba* leaf extract in the formulation is from about 0.5% to about 3% by weight. In some embodiments is a formulation described herein, wherein the concentration of suma root extract in the formulation is from about 0.5% to about 3% by weight. In some embodiments is a formulation described herein, wherein the concentration of *Cornus officinalis* fruit extract in the formulation is from about 0.5% to about 3% by weight.

In some embodiments is a formulation described herein, wherein the concentration of vitamin C in the formulation is from about 2% to about 9% by weight. In some embodiments is a formulation described herein, wherein the concentration of *Panax ginseng* root extract in the formulation is from about 5% to about 21% by weight. In some embodiments is a formulation described herein, wherein the concentration of Aswagandha root extract in the formulation is from about 4% to about 16% by weight. In some embodiments is a formulation described herein, wherein the concentration of holy basil leaf extract in the formulation is from about 3% to about 13% by weight. In some embodiments is a formulation described herein, wherein the concentration of *Rhodiola rosea* extract in the formulation is from about 2% to about 10% by weight. In some embodiments is a formulation described herein, wherein the concentration of *Eleutherococcus senticosus* extract in the formulation is from about 1% to about 7% by weight.

In some embodiments is a formulation described herein, wherein the concentration of vitamin B5 in the formulation is from about 1% to about 7% by weight. In some embodiments is a formulation described herein, wherein the concentration of phosphatidylserine is from about 20% to about 90% by weight. In some embodiments is a formulation described herein, wherein the excipient comprises gelatin, cellulose, medium-chain triglyceride (MCT) oil, silicon dioxide, stearic acid, or combinations thereof.

In some embodiments is a formulation described herein, optionally comprising broad bean. In some embodiments is a formulation described herein, wherein berberine is berberine hydrochloride. In some embodiments is a formulation described herein, wherein carnitine is carnitine tartrate. In some embodiments is a formulation described herein, wherein carnitine is L-carnitine L-tartrate. In some embodiments is a formulation described herein, wherein *Rehmannia glutinosa* extract is *Rehmania glutinosa* rhizome extract. In some embodiments is a formulation described herein, wherein the *Rehmania glutinosa* rhizome extract is a *Rehmania glutinosa* rhizome 5:1 extract. In some embodiments is a formulation described herein, wherein vitamin D is a powder. In some embodiments is a formulation described herein, further comprising at least one component that comprises vitamin E, thiamin, riboflavin, niacin, vitamin B6, folate, vitamin B12, biotin, vitamin B5, magnesium, zinc, selenium, manganese, chromium, vanadium, alpha lipoic acid, N-acetyl-cysteine, 4-aminobenzoic acid (PABA), choline bitartrate, or inositol. In some embodiments is a formulation described herein, wherein vitamin E is d-alpha tocopherol succinate. In some embodiments is a formulation described herein, wherein thiamin is at least one of benfotiamine and thiamine HCl. In some embodiments is a formulation described herein, wherein riboflavin is roboflavin-5'-phosphate. In some embodiments is a formulation described herein, wherein niacin comprises at least one of niacinamide, nicotinic acid, or a combination thereof. In some embodiments is a formulation described herein, wherein vitamin B6 is at least one of pyridoxal-5-phospate and pyridoxine HCl. In some embodiments is a formulation described herein, wherein folate is L-5-metyltetrahydrofolate.

In some embodiments is a formulation described herein, wherein vitamin B12 is cyanocobalamin. In some embodiments is a formulation described herein, wherein vitamin B5 comprises at least one of pantothenic acid, d-calcium pantothenate, pantethine, or a combination thereof. In some embodiments is a formulation described herein, wherein magnesium is magnesium citrate.

In some embodiments is a formulation described herein, wherein zinc is zinc glycinate. In some embodiments is a formulation described herein, wherein selenium is L-selenomethionine. In some embodiments is a formulation described herein, wherein manganese is manganese gluconate. In some embodiments is a formulation described herein, wherein chromium is chromium niacin complex. In some embodiments is a formulation described herein, wherein vanadium is vanadium sulfate. In some embodiments is a formulation described herein, wherein alpha lipoic acid is alpha R-lipoic acid. In some embodiments is a formulation described herein, wherein N-acetyl-cysteine is N-Acetyl L-cysteine. In some embodiments is a formulation described herein, wherein the concentration of berberine hydrochloride in the formulation is from about 6% to about 28% by weight. In some embodiments is a formulation described herein, wherein the concentration of bitter melon extract in the formulation is from about 0.2% to about 18% by weight. In some embodiments is a formulation described herein, wherein the concentration of *Gymnema sylvestre* leaf extract in the formulation is from about 8% to about 18% by weight. In some embodiments is a formulation described herein, wherein the concentration of banaba in the formulation is from about 0.2% to about 18% by weight. In some embodiments is a formulation described herein, wherein the concentration of cactus stem extract in the formulation is from about 3% to about 8% by weight. In some embodiments is a formulation described herein, wherein the concentration of L-carnitine L-tartrate in the formulation is from about 2% to about 5% by weight.

In some embodiments is a formulation described herein, wherein the concentration of *Garcinia cambogia* extract in the formulation is from about 0.2% to about 0.6% by weight. In some embodiments is a formulation described herein, wherein the concentration of *Rehmannia glutinosa* extract in the formulation is from about 0.2% to about 0.6% by weight.

In some embodiments is a formulation described herein, wherein the concentration of *Poria cocos* root extract in the formulation is from about 0.2% to about 0.6% by weight. In some embodiments is a formulation described herein, wherein the concentration of cinnamon extract in the formulation is from about 0.2% to about 0.6% by weight. In some embodiments is a formulation described herein, wherein the concentration of Fenugreek in the formulation is from about 0.2% to about 0.6% by weight. In some embodiments is a formulation described herein, wherein the concentration of Guggul in the formulation is from about 0.2% to about 0.6% by weight.

In some embodiments is a formulation described herein, optionally further comprising broad bean powder in a concentration from about 0.2% to about 0.6% by weight. In some embodiments is a formulation described herein, wherein the excipient comprises gelatin, cellulose, medium-chain triglyceride (MCT) oil, silicon dioxide, stearic acid, xanthan gum, potassium sorbate, turmeric powder, primrose oil, lemon oil, or combinations thereof.

Provided herein are methods comprising administration of at least one formulation described herein, for the treatment of diabetes in subject. In some embodiments, provided are methods for the treatment of pre-diabetic symptoms in a subject. In certain embodiments, provided are methods for the regulation of blood sugar in a subject. Certain methods described herein may comprise administration of a formulation described herein for the regulation of insulin levels in a subject.

Further provided are methods for the treatment of type II diabetes in a subject comprising: administering to the subject a first formulation described herein for at least about 10 days; administering to the subject a second formulation described herein for at least about 30 days; and optionally administering to the subject a third formulation described herein. In some embodiments, a formulation described herein is administered with an additional agent. The additional agent may comprise insulin, metformin, sulfonylureas, meglitinides, thiazolidinediones, DPP-4 inhibitors, GLP-1 receptor agonists, SGLT2 inhibitors, or a combination thereof.

In some embodiments, provided is a method of supporting glucose level in a subject's blood comprising administering to the subject one or more formulations described herein. In some embodiments is a method of supporting glucose level in a subject's blood comprising administering to the subject a formulation described herein, and optionally administering to the subject a second or additional formulation or agent described herein.

Provided are kits for use in the methods described herein. In some embodiments, provided are kits comprising at least one formulation described herein; and instructions for use thereof. In certain embodiments, provided is a kit that further comprises at least one diet plan or meal plan. In some embodiments, the kit further comprises at least one recipe.

In some embodiments is a kit useful for treating, preventing, supporting, controlling, restoring, or maintaining blood sugar levels in an individual comprising: at least one formulation described herein; instructions for use of the at least one formulation; and optionally at least one diet plan.

A diet plan described herein may further comprise recipes. In some embodiments, the diet plan further comprises recipes for at least one of breakfast, lunch, snacks, and dinner. In some embodiments, at least one diet plan is tailored to complement said at least one formulation. In some embodiments, the diet plan is tailored based on the level of at least one indicator in the individual. In certain cases, the at least one indicator is body mass index (BMI), liver fat level or hemoglobin A1C count.

In some embodiments provided herein are diet plans (also referred to as diet regimens or regimens) for implementation in conjugation with the methods and formulations described herein. A diet plan described herein is optionally included in a method and/or kit described herein. In certain embodiments, a diet plan described herein is tailored for the individual based on an understanding of the symptoms exhibited by the individual. In some embodiments, a diet plan described herein works in synergy with a method and/or formulation described herein to achieve a desired result. In some embodiments, the desired result in a reduction or stabilization of blood glucose levels. In certain embodiments, the desired result is a reduction or elimination of insulin administration. In certain embodiments, the desired result is a reduction in BMI. In some embodiments, the desired result is a reduction or elimination of one or more symptoms of type II diabetes or an associated condition described herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGS." herein), of which:

FIG. 1A shows that in an exemplary case study, upon administration of dietary supplement formulations provided herein, insulin requirement was reduced from 30 units daily to 10 units daily, and the requirement for insulin was eliminated after 4 months of administration of dietary supplement formulations provided herein. FIG. 1A also shows a significant drop in blood glucose levels as demonstrated by a two point drop in hemoglobin A1C upon four months of administration of formulations described herein. FIG. 1B shows that in another exemplary case study, upon administration of dietary supplement formulations provided herein, the individual was able to reduce insulin requirement, lost 20 lb without any additional exercise and felt an improvement in foot pain and energy levels. FIG. 1C shows that in a further exemplary case study, the individual was able to reduce insulin requirement within one week upon administration of dietary supplement formulations provided herein. FIG. 1C also demonstrates that regular administration of dietary supplement formulations provided herein resulted in a two-fold reduction in blood sugar levels, and elimination of requirements for cholesterol medication and insulin.

FIG. 2 provides results of statistical survey of 151 diabetic individuals who were administered formulations and diet plans described herein.

DETAILED DESCRIPTION

Figure 1A:
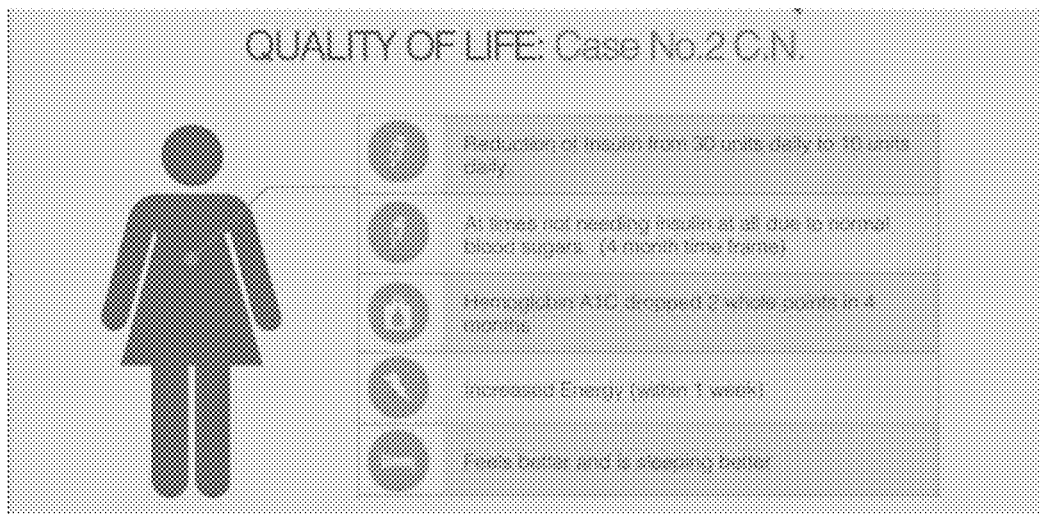
FIGS. 1A-1C provide summaries of clinical improvement in individuals diagnosed with type II diabetes upon use of the dietary supplement formulations and methods described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. It shall be understood that different aspects of the invention can be appreciated individually, collectively, or in combination with each other.

An object of the present disclosure is to provide dietary supplements, formulations and methods for administration to an individual with type II diabetes or at risk of developing type II diabetes. Provided herein are formulations and methods useful for treating, preventing, supporting, controlling, restoring, and/or maintaining blood sugar levels in individuals with type II diabetes or at risk of developing the same. Also provided are formulations and methods useful for reducing and/or eliminating requirement of ex-vivo insulin administration in an individual diagnosed with type II diabetes.

Provided herein are methods and formulations of dietary supplements that when administered to an individual treat, support and/or enhance at least one of: detoxification, eyes and ears health, natural blood sugar metabolism, male reproductive health, weight control, skin, soft tissue, skeletal tissue health, natural blood sugar levels, female reproductive health, healthy blood pressure levels, male sexual function health, glutathione levels, connective tissue health, triglyceride levels, circulatory system health, homocysteine levels, musculoskeletal health, LDL levels, antioxidant health, energy levels, reproductive health, natural pH levels, natural insulin response to glucose load, healthy HDL cholesterol levels, natural stress responses, natural glutathione levels, natural growth and repair of tissues, natural biliary levels, natural glucose tolerance, adrenal function, natural insulin receptor site sensitivity, platelet function, natural recovery time, brain function and memory, natural nerve transmission, heart and cardiovascular health, natural cell division, liver health, natural breakdown of fats, insulin health, natural bone growth, natural white blood cell levels, natural tryptophan metabolism, healthy red blood cells, natural thermogenesis, small blood vessel health, natural iron and sugar utilization, health and integrity of cellular tissue, natural secretions of insulin and glucagon, the immune system health, natural nutrient utilization, metabolism health, natural absorption of minerals, cardiovascular health, natural protein synthesis, kidney health, natural production of nucleic acids, creatine phosphate, gall bladder health, natural heme production, muscle health, natural enzymatic reactions, bone health, healthy stress responses, oral health, methionine metabolism, joint health, maintenance of a healthy nervous system, hormone health, appetite control, digestion health, glycemic control, colon health, gene expression, menstruation health, cellular repair, scalp health, nutrient transportation, intestinal health, adrenal hormones, respiratory health, chemical reactions, healthy hair, mucous membranes, and nails and overall physical and mental well-being health.

Provided herein are methods and formulations of dietary supplements that when administered to an individual treat, support and/or enhance at least one of: neutralization of toxins, eyes and ears health, natural blood sugar metabolism, male reproductive health, weight control, skin/soft tissue/ skeletal tissue health, natural blood sugar levels, female reproductive health, healthy blood pressure levels, male sexual function health, beta cells of the pancreas, connective tissue health, removal of heavy metal toxins, circulatory system health, homocysteine levels, musculoskeletal health, LDL levels, antioxidant health, energy levels, reproductive health, natural pH levels, natural cellular uptake of glucose, healthy HDL cholesterol levels, natural stress responses, natural glutathione levels, natural growth and repair of tissues, natural biliary levels, natural glucose tolerance, adrenal function, natural insulin receptor site sensitivity, platelet function, natural recovery time, brain function and memory, natural nerve transmission, heart and cardiovascular health, natural cell division, liver health, natural breakdown of fats, insulin health, natural bone growth, natural white blood cell levels, natural tryptophan metabolism, healthy red blood cells, natural thermogenesis, small blood vessel health, natural iron and sugar utilization, health and integrity of cellular tissue, natural secretions of insulin and glucagon, the immune system health, natural nutrient utilization, metabolism health, natural absorption of minerals, cardiovascular health, natural protein synthesis, kidney health, natural production of nucleic acids, creatine phosphate, gall bladder health, natural heme production, muscle health, natural enzymatic reactions, bone health, healthy stress responses, oral health, methionine metabolism, joint health, maintain a healthy nervous system, hormone health, appetite control, digestion health, glycemic control, colon health, gene expression, menstruation health, cellular repair, scalp health, nutrient transportation, intestinal health, adrenal hormones, beta cells of the pancreas, chemical reactions, healthy hair/mucous membranes/nails and physical and mental well-being. In certain embodiments, the formulations and methods further comprise fish oils or derivatives thereof, administration of which enhances and/or supports at least one of: heart health, cardiovascular health, immune system, natural liver function, natural hormones function, natural brain function, cell health, natural adrenal glands function, healthy cholesterol levels, normal blood pressure levels and insulin health.

Provided herein are methods and formulations of dietary supplements that when administered to an individual treat, support and/or enhance at least one of: blood sugar metabolism, healthy hair/mucous membranes/nails, weight control, adrenal function, natural blood sugar levels, natural fat burning, healthy blood pressure levels, cognitive function, beta cells of the pancreas, eyes and ears health, triglyceride levels, male reproductive health, natural white blood cell levels, female reproductive health, LDL levels, antioxidant health, energy levels, neuro protection, pH levels, cellular uptake of glucose, healthy HDL cholesterol levels, stamina, glutathione levels, glucokinase activity, natural biliary levels, GABA, natural hormone levels, natural insulin receptor site sensitivity, brain function and memory, natural insulin health, platelet function, natural adrenal hormones, heart and cardiovascular health, natural adrenal glands function, natural liver function, nutrient transportation, insulin health, digestion health, healthy red blood cells, glycemic control, colon health, healthy uric acid levels, small blood vessel health, gene expression, gastrointestinal health, physical and mental well-being health, hormone health, maintain a healthy nervous system, health and integrity of cellular tissue, natural secretions of insulin and glucagon, the immune system health, joint health, healthy metabolic processes, secretions of insulin and glucagon, glucose tolerance, natural enzymatic reactions, tryptophan metabolism, intestinal health, kidney health, cartilage, thyroid health, peripheral glucose utilization, muscle health, natural insulin production, bone health, natural stress responses, oral health, methionine metabolism, the manufacture and utilization of carbohydrates/fats/amino acids, and formation of fats/proteins/carbohydrates/amino acids/antibiotics. In certain embodiments, the formulations and methods further comprise fish oils or derivatives thereof, administration of which enhances and/or supports at least one of: heart health, cardiovascular health, immune system, natural liver function, natural hormones function, natural brain function, cell health, natural adrenal glands function, healthy cholesterol levels, normal blood pressure levels and insulin health.

Unless defined otherwise, all technical and scientific terms used herein have the same meaning as is commonly understood by one of skill in the art to which the claimed subject matter belongs.

It is to be understood that the foregoing general description and the following detailed description are exemplary and explanatory only and are not restrictive of any subject matter claimed. In this application, the use of the singular includes the plural unless specifically stated otherwise.

In the present description, any concentration range, percentage range, ratio range, or integer range is to be understood to include the value of any integer within the recited range and, when appropriate, fractions thereof (such as one tenth and one hundredth of an integer), unless otherwise indicated. As used herein, "about" means±10% of the indicated range, value, sequence, or structure, unless otherwise indicated. It should be understood that the terms "a" and "an" as used herein refer to "one or more" of the enumerated components unless otherwise indicated or dictated by its context. The use of the alternative (e.g., "or") should be understood to mean either one, both, or any combination thereof of the alternatives. As used herein, the terms "include" and "comprise" are used synonymously.

It is to be understood that the methods, formulations and compositions described herein are not limited to the particular methodology, protocols, methods, and reagents described herein and as such may vary. It is also to be understood that the terminology used herein is for the purpose of describing particular embodiments only, and is not intended to limit the scope of the methods and compositions described herein, which will be limited only by the appended claims.

Exemplary Ingredients

The methods, dietary supplements and formulations described herein may comprise at least one of the ingredients discussed below. In certain embodiments, formulations described herein comprise a plurality of ingredients described below. In certain embodiments, two or more ingredients are combined in an amount suitable to provide synergistic effects. Formulations and dietary supplements described herein may contain other active and inactive ingredients in addition to one or more ingredients described herein.

Biotin: Alternatively called vitamin H or coenzyme R a water-soluble B-vitamin (vitamin $B_7$). Certain methods and formulations described herein comprise a suitable amount of biotin or derivative or analog thereof. In certain embodiments, methods and formulations of dietary supplements comprise biotin or derivative or analog thereof in an amount suitable to support and/or enhance at least one of: blood sugar control, cholesterol levels, insulin response to glucose load, manufacture and utilization of carbohydrates/fats/amino acids, maintenance of insulin receptor site sensitivity, glucokinase activity, hair growth, nail health and metabolism.

Chromium Picloinate: In some embodiments, the source of chromium is chromium polynicotinate. Certain methods and formulations described herein comprise a suitable amount of chromium piclonate or derivative or analog thereof, including for instance any type of chromium. In certain embodiments, methods and formulations of dietary supplements comprise chromium piclonate or derivative or analog thereof in an amount suitable to support and/or enhance at least one of: blood sugar level, cholesterol level, optimizing the impact of insulin on insulin receptor sites, thermogenesis, healthy triglyceride levels, healthy HDL cholesterol, metabolism, regulating food cravings and normal blood pressure.

Vitamin A: is a group of unsaturated nutritional organic compounds, that includes retinol, retinal, retinoic acid, and several provitamin A carotenoids, among which beta-carotene is the most important. Certain methods and formulations described herein comprise a suitable amount of vitamin A or derivative or analog thereof. In certain embodiments, methods and formulations of dietary supplements comprise vitamin A or derivative or analog thereof in an amount suitable to support and/or enhance at least one of: eye health, healthy vision, cofactors for toxin breakdown, homocysteine levels, moisture levels for eyes/skin/mucous membranes, antioxidant levels, heart health, skin/soft tissue/skeletal tissue health.

Vitamin C or L-ascorbic acid, or ascorbate: Certain methods and formulations described herein comprise a suitable amount of vitamin C or derivative or analog thereof. In certain embodiments, methods and formulations of dietary supplements comprise vitamin C or derivative or analog thereof in an amount suitable to support and/or enhance at least one of: neutralization of toxins, glutathione levels, immune system, removal of heavy metal toxins, blood sugar metabolism, beta cells of the pancreas, antioxidation, and growth and repair of tissues Vitamin D: In some embodiments, the source of Vitamin D is vitamin D3 (also known as cholecalciferol). In some embodiments, the source of Vitamin D is vitamin D2 (ergocalciferol). Certain methods and formulations described herein comprise a suitable amount of vitamin D or derivative or analog thereof. In certain embodiments, methods and formulations of dietary supplements comprise vitamin D or derivative or analog thereof in an amount suitable to support and/or enhance at least one of: blood sugar metabolism, heart and cardiovascular health, immune function, insulin receptor site activity, bone health, reducing the risk of some forms of cancer, alleviating musculoskeletal pain Vitamin E: In some embodiments the source of Vitamin E is a tocopherol. In some embodiments, the source of Vitamin E is a tocotrienol. In some embodiments, tocopherol is γ-tocopherol. In some embodiments, tocopherol is α-tocopherol. In some embodiments, the source of Vitamin E is α-tocopherol succinate. Certain methods and formulations described herein comprise a suitable amount of vitamin E or derivative or analog thereof. In certain embodiments, methods and formulations of dietary supplements comprise vitamin E or derivative or analog thereof in an amount suitable to support and/or enhance at least one of: free radical elimination, health and integrity of cellular tissue, healthy insulin receptor site activity, triglyceride levels, LDL levels, platelet function, glycemic control, antioxidant levels, and immune function.

Vitamin B1: In some embodiments, the source of Vitamin B1 is thiamine (or thiamin). In some embodiments, the source of Vitamin B1 is thiamine hydrochloride. In some embodiments, the source of vitamin B1 is Benfotiamine. Certain methods and formulations described herein comprise a suitable amount of vitamin B1 or derivative or analog thereof. In certain embodiments, methods and formulations of dietary supplements comprise vitamin B1 or derivative or analog thereof in an amount suitable to support and/or enhance at least one of: cofactor levels for energy production, antioxidation, neuro-protection, small blood vessel health, blood sugar metabolism, cholesterol levels, energy production, heart and cardiovascular health, and brain function and memory.

Vitamin B2 or riboflavin: Certain methods and formulations described herein comprise a suitable amount of vitamin B2 or derivative or analog thereof. In certain embodiments, methods and formulations of dietary supplements comprise vitamin B2 or derivative or analog thereof in an amount suitable to support and/or enhance at least one of: antioxidation, energy production, immune function, energy levels, maintenance of healthy hair, skin, mucous membranes, and nails, reproductive function, liver and memory.

Niacin also known as vitamin $B_3$ or nicotinic acid: Certain methods and formulations described herein comprise a suitable amount of niacin or derivative or analog thereof. In certain embodiments, methods and formulations of dietary supplements comprise niacin or derivative or analog thereof in an amount suitable to support and/or enhance at least one of: energy production, oxidation, cholesterol levels, blood sugar metabolism, beta cells of the pancreas, adrenal function, support and maintenance of a healthy nervous system, one or more metabolic processes, and healthy cardiovascular function.

Vitamin B6: In some embodiments, the source of Vitamin B6 is Pyridoxal 5'-phosphate (PLP).: In some embodiments, the source of Vitamin B6 is pyridoxine. Certain methods and formulations described herein comprise a suitable amount of vitamin B6 or derivative or analog thereof. In certain embodiments, methods and formulations of dietary supplements comprise vitamin B6 or derivative or analog thereof in an amount suitable to support and/or enhance at least one of: antioxidation, energy production, homocysteine levels, blood sugar metabolism, glucose tolerance, secretions of insulin and glucagon, tryptophan metabolism and neuro-protection.

Vitamin B12 also called cobalamin: In some embodiments the source of vitamin B12 is methylcobalamin. In some embodiments, the source of Vitamin B12 is cyanocobalamin. Certain methods and formulations described herein comprise a suitable amount of vitamin B12 or derivative or analog thereof. In certain embodiments, methods and formulations of dietary supplements comprise vitamin B12 or derivative or analog thereof in an amount suitable to support and/or enhance at least one of: healthy homocysteine levels, healthy red blood cells, energy production, immune system and neuro-protection.

Magnesium: In some embodiments, the source of magnesium is magnesium citrate. In some embodiments, the source of magnesium is magnesium glycinate. Certain methods and formulations described herein comprise a suitable amount of magnesium or derivative or analog thereof. In certain embodiments, methods and formulations of dietary supplements comprise magnesium or derivative or analog thereof in an amount suitable to support and/or enhance at least one of: mood stabilization, muscle health, blood pressure, cardiovascular system, bone health, metabolism, blood sugar levels, insulin receptor site sensitivity, cholesterol levels and platelet activity.

*Ginseng*: In some embodiments, the *ginseng* is Asian or Korean *ginseng* (*Panax ginseng*). In some embodiments, the *ginseng* is American *ginseng* (*Panax quinquefolius*). Certain methods and formulations described herein comprise a suitable amount of *ginseng* or derivative or analog thereof. In certain embodiments, methods and formulations of dietary supplements comprise *ginseng* or derivative or analog thereof in an amount suitable to support and/or enhance at least one of: immune function, carbohydrate absorption by the intestines, blood sugar metabolism, insulin production, menstruation, weight control, physical and mental well-being and male sexual function Fenugreek: Certain methods and formulations described herein comprise a suitable amount of fenugreek or derivative or analog thereof. In certain embodiments, methods and formulations of dietary supplements comprise fenugreek or derivative or analog thereof in an amount suitable to support and/or enhance at least one of: blood sugar metabolism, insulin sensitivity, cholesterol levels, insulin production, minerals inclusive of iron, potassium, calcium, selenium, copper, zinc, manganese, and magnesium, thiamin, folic acid, riboflavin, pyridoxine (vitamin B6), niacin, and vitamins A and C, LDL levels and mental aging.

Holy Basil Leaf also known as *Ocimum sanctum, Ocimum tenuifloru* or *Tulsi*: Certain methods and formulations described herein comprise a suitable amount of holy basil leaf or derivative or analog thereof. In certain embodiments, methods and formulations of dietary supplements comprise holy basil leaf or derivative or analog thereof in an amount suitable to support and/or enhance at least one of: blood sugar metabolism, stress responses, immune responses, platelet activity, cholesterol levels, storage of glucose as glycogen, adaptogen and therefore supports healthy stress responses, and support for gastro-intestinal health.

Bitter Melon: Certain methods and formulations described herein comprise a suitable amount of bitter melon or derivative or analog thereof. In certain embodiments, methods and formulations of dietary supplements comprise bitter melon or derivative or analog thereof in an amount suitable to support and/or enhance at least one of: blood sugar metabolism, pancreatic beta cells, gastro-intestinal health, and liver function.

*Gymnema* also known as *Gymnema Sylvestre*: Certain methods and formulations described herein comprise a suitable amount of *gymnema* or derivative or analog thereof. In certain embodiments, methods and formulations of dietary supplements comprise *gymnema* or derivative or analog thereof in an amount suitable to support and/or enhance at least one of: blood sugar metabolism, sugar cravings, insulin responses, insulin receptor site sensitivity, cholesterol levels, weight loss, digestion, and pancreatic beta cells.

Prickly Pear Cactus (Nopal): Certain methods and formulations described herein comprise a suitable amount of prickly pear cactus or derivative or analog thereof. In certain embodiments, methods and formulations of dietary supplements comprise prickly pear cactus or derivative or analog thereof in an amount suitable to support and/or enhance at least one of: blood sugar metabolism and regulation of cholesterol levels.

Cinammon: Certain methods and formulations described herein comprise a suitable amount of cinnamon or derivative or analog thereof. In certain embodiments, methods and formulations of dietary supplements comprise cinnamon or derivative or analog thereof in an amount suitable to support and/or enhance at least one of: blood sugar metabolism, digestion, appetite normalization, alleviation of fungal infection, and cholesterol levels.

Vanadium: Certain methods and formulations described herein comprise a suitable amount of vanadium or derivative or analog thereof. In certain embodiments, methods and formulations of dietary supplements comprise vanadium or derivative or analog thereof in an amount suitable to support and/or enhance at least one of: blood sugar metabolism, cholesterol levels, heart health and water retention. In some embodiments, the source of vanadium is vanadium sulfate.

Lipoic Acid: Certain methods and formulations described herein comprise a suitable amount of Lipoic Acid or derivative or analog thereof. In certain embodiments, methods and formulations of dietary supplements comprise Lipoic Acid or derivative or analog thereof in an amount suitable to support and/or enhance at least one of: blood sugar metabolism, enzymatic reactions in the body, insulin sensitivity, mediation of oxidative stress, liver, bone health, eye health, neurological system, skin, blood pressure, cholesterol and weight regulation. In some embodiments, lipoic acid is R-lipoic acid.

Zinc: Certain methods and formulations described herein comprise a suitable amount of zinc or derivative or analog thereof. In certain embodiments, methods and formulations of dietary supplements comprise zinc or derivative or analog thereof in an amount suitable to support and/or enhance at least one of: immune function, cell division, hormone levels, antioxidation, healthy stress responses, red blood cells, white blood cells, male reproductive health, female reproductive health, cardiovascular system, blood sugar metabolism, brain health, cholesterol stabilization and mood stabilization. In some embodiments, the source of zinc is zinc glycinate. In some embodiments the source of zinc is zinc L-monomethionine.

Calcium: Certain methods and formulations described herein comprise a suitable amount of calcium or derivative or analog thereof. In certain embodiments, methods and formulations of dietary supplements comprise calcium or derivative or analog thereof in an amount suitable to support and/or enhance at least one of: bone health, nerve transmission, blood sugar metabolism, oral health, weight regulation, colon health, muscle health, heart health, normal blood pressure, blood sugar metabolism, joint health, kidney health, pH level, and nutrient transportation. In some embodiments calcium is calcium ascorbate. In some embodiment calcium is calcium citrate malate.

Selenium: Certain methods and formulations described herein comprise a suitable amount of selenium or derivative or analog thereof. In certain embodiments, methods and formulations of dietary supplements comprise selenium or derivative or analog thereof in an amount suitable to support and/or enhance at least one of: thyroid health, DNA synthesis, immune function, reproduction, blood sugar metabolism, antioxidation, and bone growth. In some embodiments, the source of selenium is L-selenomethionine.

Artichoke extract: Certain methods and formulations described herein comprise a suitable amount of artichoke extract or derivative or analog thereof. In certain embodiments, methods and formulations of dietary supplements comprise artichoke extract or derivative or analog thereof in an amount suitable to support and/or enhance at least one of: cholesterol, heart function, liver function, blood sugar metabolism, antioxidation, digestion, and apoptosis.

*Ginkgo Biloba*: Certain methods and formulations described herein comprise a suitable amount of gingko *biloba*, extract or derivative or analog thereof. In certain embodiments, methods and formulations of dietary supplements comprise gingko *biloba*, extract or derivative or analog thereof in an amount suitable to support and/or enhance at least one of: platelet function, memory, blood flow to the brain, oxygen utilization, vision, eyes, and mood stabilization.

Vitamin B5. In some embodiments, the source of Vitamin B5 is Pantothenic Acid. In some embodiments the source of vitamin B5 is calcium pantothenate. In some embodiments, the source of Vitamin B5 is pantethine. Certain methods and formulations described herein comprise a suitable amount of Vitamin B5 or derivative or analog thereof. In certain embodiments, methods and formulations of dietary supplements comprise Vitamin B5 or derivative or analog thereof in an amount suitable to support and/or enhance at least one of: acetylcholine, hair, mood stabilization, stress responses, heart health, immune health, joint health, adrenal hormones, formation of fats/proteins/carbohydrates/amino acids/antibiotics, and stamina.

Phosphorus: Certain methods and formulations described herein comprise a suitable amount of phosphorous or derivative or analog thereof. In certain embodiments, methods and formulations of dietary supplements comprise phosphorus or derivative or analog thereof in an amount suitable to support and/or enhance at least one of: bone, digestion, hormones, energy, cellular repair, chemical reactions, proper nutrient utilization, kidneys, brain support and protein formation. In some embodiments, the source of phosphorus is disodium phosphate.

Copper: Certain methods and formulations described herein comprise a suitable amount of copper or derivative or analog thereof. In certain embodiments, methods and formulations of dietary supplements comprise copper or derivative or analog thereof in an amount suitable to support and/or enhance at least one of: joint health, proper growth, connective tissues, brain, enzymatic reactions, iron and sugar utilization, energy production, thyroid health, red blood cell formation, immune system, and healthy cholesterol levels. In some embodiments, the source of copper is copper gluconate.

Manganese: Certain methods and formulations described herein comprise a suitable amount of manganese or derivative or analog thereof. In certain embodiments, methods and formulations of dietary supplements comprise manganese or derivative or analog thereof in an amount suitable to support and/or enhance at least one of: GABA, bones, antioxidation, blood sugar metabolism, overall metabolism, inflammation alleviation, thyroid, absorption, brain, nervous system and digestion. In some embodiments, the source of manganese is manganese gluconate.

Molybdenum: Certain methods and formulations described herein comprise a suitable amount of molybdenum or derivative or analog thereof. In certain embodiments, methods and formulations of dietary supplements comprise molybdenum or derivative or analog thereof in an amount suitable to support and/or enhance at least one of: uric acid stabilization, sulfation, enzyme levels, inflammation alleviation, and detoxification. In some embodiments the source of molybdenum is molybdenum amino acid chelate.

Trimethylglycine: Certain methods and formulations described herein comprise a suitable amount of trimethylglycine or derivative or analog thereof. In certain embodiments, methods and formulations of dietary supplements comprise trimethylglycine or derivative or analog thereof in an amount suitable to support and/or enhance at least one of: methionine metabolism, homocysteine levels and liver function.

Evening Primrose Oil also known as Cis-Linoleic Acid Certain methods and formulations described herein comprise a suitable amount of evening primrose oil or derivative or analog thereof. In certain embodiments, methods and formulations of dietary supplements comprise evening primrose oil or derivative or analog thereof in an amount suitable to support and/or enhance at least one of: skin health and function, inflammation alleviation, menstruation, neuro-protection, memory, nails, scalp, and hair, prostaglandin E2, and gastro-intestinal tract.

Inulin: Certain methods and formulations described herein comprise a suitable amount of inulin or derivative or analog thereof. In certain embodiments, methods and formulations of dietary supplements comprise inulin or derivative or analog thereof in an amount suitable to support and/or enhance at least one of: intestinal health, immune system, short-chain fatty acids, liver, cardiovascular functions, absorption of minerals and digestion.

Medium Chain Triglycerides: Certain methods and formulations described herein comprise a suitable amount of medium chain triglycerides or derivative or analog thereof. In certain embodiments, methods and formulations of dietary supplements comprise medium chain triglycerides or derivative or analog thereof in an amount suitable to support and/or enhance at least one of: absorption, energy, weight control, appetite control, cardiovascular system, and immune system.

Quercetin, also known as 3,3',4'5,7-Penthydroxyflavone, bioflavonoid, bioflavonoid complex, bioflavonoid concentrate, bioflavonoid extract: In some embodiments, the source of quercetin is quercetin dihydrate. Certain methods and formulations described herein comprise a suitable amount of quercetin or derivative or analog thereof. In certain embodiments, methods and formulations of dietary supplements comprise quercetin or derivative or analog thereof in an amount suitable to support and/or enhance at least one of: antioxidation, inflammation alleviation, histamine regulation, respiratory health, cardiovascular system, blood pressure regulation and stress management.

Rutin, also called rutoside, quercetin-3-O-rutinoside and sophorin: Certain methods and formulations described herein comprise a suitable amount of rutin or derivative or analog thereof. In certain embodiments, methods and formulations of dietary supplements comprise rutin or derivative or analog thereof in an amount suitable to support and/or enhance at least one of: antioxidation, inflammation alleviation, utilization of vitamin C, high blood pressure regulation, hemorrhoid alleviation, cholesterol and blood vessel health.

Hesperidin: Certain methods and formulations described herein comprise a suitable amount of hersperidin or derivative or analog thereof. In certain embodiments, methods and formulations of dietary supplements comprise hersperidin or derivative or analog thereof in an amount suitable to support and/or enhance at least one of: antioxidation, inflammation alleviation, blood pressure regulation, and blood vessel health.

Milk thistle, also known as silybum marianum, or silymarin: Certain methods and formulations described herein comprise a suitable amount of milk thistle or extract or derivative or analog thereof. In certain embodiments, methods and formulations of dietary supplements comprise milk thistle or extract or derivative or analog thereof in an amount suitable to support and/or enhance at least one of: bile levels, biliary cholesterol levels, bile saturation index, antioxidation, detoxification pathways, inflammation alleviation and protein synthesis.

Taurine also known as 2-aminoethanesulfonic acid: In some embodiment the source of taurine is L-taurine. Certain methods and formulations described herein comprise a suitable amount of taurine or derivative or analog thereof. In certain embodiments, methods and formulations of dietary supplements comprise taurine or derivative or analog thereof in an amount suitable to support and/or enhance at least one of: obesity management, blood sugar metabolism, heart health, life-span improvements, eyes and ears health, liver health, cardiovascular system, insulin action, antioxidation, calcium, magnesium, potassium, sodium, blood pressure, platelet activity, bile acids and cholesterol.

Choline: In some embodiments, the source of choline is choline bitartrate. Certain methods and formulations described herein comprise a suitable amount of choline or derivative or analog thereof. In certain embodiments, methods and formulations of dietary supplements comprise choline or derivative or analog thereof in an amount suitable to support and/or enhance at least one of: liver function, moods, memory, endurance, and cholesterol levels.

Betaine Hydrochloride: Certain methods and formulations described herein comprise a suitable amount of betaine hydrochloride or derivative or analog thereof. In certain embodiments, methods and formulations of dietary supplements comprise betaine hydrochloride or derivative or analog thereof in an amount suitable to support and/or enhance at least one of: digestion and gall bladder function.

Marshmallow root: Certain methods and formulations described herein comprise a suitable amount of marshmallow root or extract or derivative or analog thereof. In certain embodiments, methods and formulations of dietary supplements comprise marshmallow root or extract or derivative or analog thereof in an amount suitable to support and/or enhance at least one of: inflammation alleviation, intestinal and digestive health.

Curcumin: Certain methods and formulations described herein comprise a suitable amount of curcumin or derivative or analog thereof. In certain embodiments, methods and formulations of dietary supplements comprise curcumin or derivative or analog thereof in an amount suitable to support and/or enhance at least one of: inflammation response, antioxidation, liver and brain health, immune system, dopanergic neurons and neuro-protection L-glutamine: Certain methods and formulations described herein comprise a suitable amount of L-glutamine or derivative or analog thereof. In certain embodiments, methods and formulations of dietary supplements comprise L-glutamine or derivative or analog thereof in an amount suitable to support and/or enhance at least one of: sulfation, methylation, detoxification, glutathione storage, oxidative stress management and small intestine health.

N-Acetyl-L-Cysteine: Certain methods and formulations described herein comprise a suitable amount of N-Acetyl-L-Cystine or derivative or analog thereof. In certain embodiments, methods and formulations of dietary supplements comprise N-Acetyl-L-Cystine or derivative or analog thereof in an amount suitable to support and/or enhance at least one of: glutathione level management, gene expression, inflammation alleviation, antioxidation and insulin receptor site sensitivity.

Ginger root: Certain methods and formulations described herein comprise a suitable amount of ginger root or extract or derivative or analog thereof. In certain embodiments, methods and formulations of dietary supplements comprise ginger root or extract or derivative or analog thereof in an amount suitable to support and/or enhance at least one of: bile secretion, liver cholesterol levels, inflammation alleviation, blood sugar metabolism, cholesterol management, insulin levels, insulin sensitivity, digestion, heart health, and weight management.

Bromelain: Certain methods and formulations described herein comprise a suitable amount of bromelian or derivative or analog thereof. In certain embodiments, methods and formulations of dietary supplements comprise bromelain or derivative or analog thereof in an amount suitable to support and/or enhance at least one of: digestion, inflammation alleviation, recovery time, and joint health Methyl sulfonyl methane (MSM): Certain methods and formulations described herein comprise a suitable amount of MSM or derivative or analog thereof. In certain embodiments, methods and formulations of dietary supplements comprise MSM or derivative or analog thereof in an amount suitable to support and/or enhance at least one of: inflammation alleviation, sulfation and liver-gut axis health.

S-Adenosyl Methionine (sam-E): Certain methods and formulations described herein comprise a suitable amount of sam-E or derivative or analog thereof. In certain embodiments, methods and formulations of dietary supplements comprise sam-E or derivative or analog thereof in an amount suitable to support and/or enhance at least one of: mood stabilization, brain, liver, joints support.

Dandelion root: Certain methods and formulations described herein comprise a suitable amount of dandelion root or extract or derivative or analog thereof. In certain embodiments, methods and formulations of dietary supplements comprise dandelion root or extract or derivative or analog thereof in an amount suitable to support and/or enhance at least one of: liver, gall bladder, bile function, digestion and cholesterol level.

Lecithin: Certain methods and formulations described herein comprise a suitable amount of lecithin or derivative or analog thereof. In certain embodiments, methods and formulations of dietary supplements comprise lecithin or derivative or analog thereof in an amount suitable to support and/or enhance at least one of: biliary system, lipids, nervous system, circulatory system, metabolism, heart health, and memory.

Beet root: Certain methods and formulations described herein comprise a suitable amount of beet root or extract or derivative or analog thereof. In certain embodiments, methods and formulations of dietary supplements comprise beet root or extract or derivative or analog thereof in an amount suitable to support and/or enhance at least one of: blood pressure, stamina, inflammation management, and detoxification.

Superoxide Dismutase: Certain methods and formulations described herein comprise a suitable amount of superoxide dismutase or derivative or analog thereof. In certain embodiments, methods and formulations of dietary supplements comprise superoxide dismutase or derivative or analog thereof in an amount suitable to support and/or enhance at least one of: antioxidation, and inflammation management.

Sarsparilla root: Certain methods and formulations described herein comprise a suitable amount of sarsparilla root or extract or derivative or analog thereof. In certain embodiments, methods and formulations of dietary supplements comprise sarsparilla root or extract or derivative or analog thereof in an amount suitable to support and/or enhance at least one of: skin, kidney, detoxification and inflammation alleviation.

DL-Methionine: Certain methods and formulations described herein comprise a suitable amount of DL-methionine or derivative or analog thereof. In certain embodiments, methods and formulations of dietary supplements comprise DL-methionine or derivative or analog thereof in an amount suitable to support and/or enhance at least one of: liver, breakdown of fats and antioxidation.

Gotu Kola: Certain methods and formulations described herein optionally comprise a suitable amount of gotu kola or extract or derivative or analog thereof. In certain embodiments, methods and formulations of dietary supplements comprise gota kola or extract or derivative or analog thereof in an amount suitable to support and/or enhance at least one of: detoxification, liver and venous system health.

L-glutathione: Certain methods and formulations described herein comprise a suitable amount of L-glutathione or derivative or analog thereof. In certain embodiments, methods and formulations of dietary supplements comprise L-glutathione or derivative or analog thereof in an amount suitable to support and/or enhance at least one of: heart functioning and health, cardiovascular system, detoxification, liver health, mood stabilization, respiratory system, antioxidation, and inflammation alleviation.

L-Glycine: Certain methods and formulations described herein comprise a suitable amount of L-glycine or derivative or analog thereof. In certain embodiments, methods and formulations of dietary supplements comprise L-glycine or derivative or analog thereof in an amount suitable to support and/or enhance at least one of: production of nucleic acids, bile acids, creatine phosphate; breakdown of fats; heme production; mood stabilization; blood sugar metabolism; muscle growth; hormones and heart health.

Watercress Leaf: Certain methods and formulations described herein comprise a suitable amount of watercress leaf or extract or derivative or analog thereof. In certain embodiments, methods and formulations of dietary supplements comprise watercress leaf or extract or derivative or analog thereof in an amount suitable to support and/or enhance at least one of: antioxidation and DNA against damage.

Banaba Leaf: Certain methods and formulations described herein comprise a suitable amount of banaba leaf or extract or derivative or analog thereof. In certain embodiments, methods and formulations of dietary supplements comprise banaba leaf or extract or derivative or analog thereof in an amount suitable to support and/or enhance at least one of: blood sugar metabolism, peripheral glucose utilization, weight control, cholesterol maintenance, insulin sensitivity, cellular uptake of glucose, triglyceride levels, antioxidation, inflammation response and bone health.

Berberine Hydrochloride: Certain methods and formulations described herein comprise a suitable amount of berberine hydrochloride or derivative or analog thereof. In certain embodiments, methods and formulations of dietary supplements comprise berberine hydrochloride or derivative or analog thereof in an amount suitable to support and/or enhance at least one of: blood sugar metabolism, weight management, cholesterol, triglycerides, cognitive function, heart health, cardiovascular, cartilage and bone health, neuroprotection, inflammation alleviation and intestinal health.

Bitter Melon: Certain methods and formulations described herein comprise a suitable amount of bitter melon or extract or derivative or analog thereof. In certain embodiments, methods and formulations of dietary supplements comprise bitter melon or extract or derivative or analog thereof in an amount suitable to support and/or enhance at least one of: blood sugar levels/metabolism, cholesterol and weight management, triglycerides, antioxidation and digestion.

Citrimax: Certain methods and formulations described herein comprise a suitable amount of citrimax or extract or derivative or analog thereof. In certain embodiments, methods and formulations of dietary supplements comprise citrimax or extract or derivative or analog thereof in an amount suitable to support and/or enhance at least one of: weight loss and appetite control.

Guggul: Certain methods and formulations described herein comprise a suitable amount of guggul or extract or derivative or analog thereof. In certain embodiments, methods and formulations of dietary supplements comprise guggul or extract or derivative or analog thereof in an amount suitable to support and/or enhance at least one of: blood sugar levels/metabolism, cholesterol and weight management, triglycerides, antioxidation and digestion, thyroid health, LDL levels, lipid peroxidation and cholesterol maintenance.

*Poria Cocos* Root: Certain methods and formulations described herein comprise a suitable amount of *poria cocos* root or extract or derivative or analog thereof. In certain embodiments, methods and formulations of dietary supplements comprise *poria cocos* root or extract or derivative or analog thereof in an amount suitable to support and/or enhance at least one of: inflammation alleviation, gastrointestinal health, mood stabilization, water retention (diuretic), and central nervous system maintenance.

*Rehmannia Glutinosa* or Chinese Foxglove: Certain methods and formulations described herein comprise a suitable amount of *rehmannia glutinosa* or extract or derivative or analog thereof. In certain embodiments, methods and formulations of dietary supplements comprise *rehmannia glutinosa* or extract or derivative or analog thereof in an amount suitable to support and/or enhance at least one of: inflammation alleviation, blood sugar metabolism, red blood cell formation, kidneys, and energy.

Broad Bean: Certain methods and formulations described herein optionally comprise a suitable amount of broad bean or extract or derivative or analog thereof. In certain embodiments, methods and formulations of dietary supplements comprise broad bean or extract or derivative or analog thereof in an amount suitable to support and/or enhance at least one of: antioxidation support, dopamine, and cholesterol maintenance.

Inositol or cyclohexane-1,2,3,4,5,6-hexol: Certain methods and formulations described herein comprise a suitable amount of inositol or derivative or analog thereof. In certain embodiments, methods and formulations of dietary supplements comprise inositol or derivative or analog thereof in an amount suitable to support and/or enhance at least one of: neuroprotection, hair health, cholesterol stabilization, mood stabilization, blood sugar metabolism, and digestion.

L-Carnitine tartrate: Certain methods and formulations described herein comprise a suitable amount of L-carnitine tartrate or derivative or analog thereof. In certain embodiments, methods and formulations of dietary supplements comprise L-carnitine tartrate or derivative or analog thereof in an amount suitable to support and/or enhance at least one of: heart health, cardiovascular system, fat burning, brain, fatty liver alleviation, insulin sensitivity, blood sugar metabolism, neuroprotection and cholesterol maintenance.

Para-aminobenzoic acid (PABA): Certain methods and formulations described herein comprise a suitable amount of PABA or derivative or analog thereof. In certain embodiments, methods and formulations of dietary supplements comprise PABA or derivative or analog thereof in an amount suitable to support and/or enhance at least one of: antioxidation and utilization of B5.

Asiatic Dogwood Fruit: Certain methods and formulations described herein comprise a suitable amount of asiatic dogwood fruit or extract or derivative or analog thereof. In certain embodiments, methods and formulations of dietary supplements comprise asiatic dogwood fruit or extract or derivative or analog thereof in an amount suitable to support and/or enhance at least one of: inflammation control, antioxidation, cholesterol maintenance, liver and kidney health, cardiovascular health, menstruation, immune system regulation and blood sugar metabolism.

*Cordyceps*: Certain methods and formulations described herein comprise a suitable amount of *cordyceps* or extract or derivative or analog thereof. In certain embodiments, methods and formulations of dietary supplements comprise *cordyceps* or extract or derivative or analog thereof in an amount suitable to support and/or enhance at least one of: cholesterol stabilization, cellular repair, DNA repair, liver and kidney health, immune system health, antioxidation and energy.

Maca also known as Peruvian *Ginseng*: Certain methods and formulations described herein comprise a suitable amount of maca or extract or derivative or analog thereof. In certain embodiments, methods and formulations of dietary supplements comprise maca or extract or derivative or analog thereof in an amount suitable to support and/or enhance at least one of: stress management, and mood stabilization.

Suma root: Certain methods and formulations described herein comprise a suitable amount of suma root or extract or derivative or analog thereof. In certain embodiments, methods and formulations of dietary supplements comprise suma root or extract or derivative or analog thereof in an amount suitable to support and/or enhance at least one of: blood sugar metabolism, adaptogenic/stress, adrenal glands, hormones, blood sugar metabolism, energy, heart health and inflammation alleviation.

Aswagandha Root, also known as *Withania somnifera*: Certain methods and formulations described herein comprise a suitable amount of aswagandha root or extract or derivative or analog thereof. In certain embodiments, methods and formulations of dietary supplements comprise aswagandha root or extract or derivative or analog thereof in an amount suitable to support and/or enhance at least one of: stress reduction, adrenal glands function, liver, antioxidation, thyroid and healthy cortisol levels.

*Rhodiola Rosea*: Certain methods and formulations described herein comprise a suitable amount of *rhodiola rosea* or extract or derivative or analog thereof. In certain embodiments, methods and formulations of dietary supplements comprise *rhodiola rosea* or extract or derivative or analog thereof in an amount suitable to support and/or enhance at least one of: central nervous system, mood stabilization, heart health, cardiovascular health, healthy stress response, immune system, cognitive function, and mental energy.

*Eleutherococcus Senticosus*: Certain methods and formulations described herein comprise a suitable amount of *eleutherococcus senticosus* or extract or derivative or analog thereof. In certain embodiments, methods and formulations of dietary supplements comprise *eleutherococcus senticosus* or extract or derivative or analog thereof in an amount suitable to support and/or enhance at least one of: stress management, energy, LDL cholesterol, and adrenal feedback loop.

Pantethine: Certain methods and formulations described herein comprise a suitable amount of pantethine or extract or derivative or analog thereof. In certain embodiments, methods and formulations of dietary supplements comprise pantetheine or extract or derivative or analog thereof in an amount suitable to support and/or enhance at least one of: adrenals, adrenal hormones, stress, and cortisol.

*Salacia oblonga*: Certain methods and formulations described herein comprise a suitable amount of *salacia oblonga* or extract or derivative or analog thereof. In certain embodiments, methods and formulations of dietary supplements comprise *salacia oblonga* or extract or derivative or analog thereof in an amount suitable to support and/or enhance at least one of: blood sugar metabolism, joint health, menstruation, and weight management.

Phosphatidyl Serine: Certain methods and formulations described herein comprise a suitable amount of phosphatidyl serine or derivative or analog thereof. In certain embodiments, methods and formulations of dietary supplements comprise phosphatidyl serine or derivative or analog thereof in an amount suitable to support and/or enhance at least one of: cellular chemical signaling, brain health, hippocampus function, stress alleviation, HPA axis, cortisol levels, and sleep.

Eicosapentaenoic acid and Docosahexaenoic acid (EPA/DHA): Certain methods and formulations described herein comprise a suitable amount of EPA/DHA or derivative or analog thereof. In certain embodiments, methods and formulations of dietary supplements comprise EPA/DHA or derivative or analog thereof in an amount suitable to support and/or enhance at least one of: inflammation alleviation, heart health, cardiovascular health, immune system regulation, liver health, hormones, brain health, cells, adrenal glands, cholesterol management, blood pressure management, and insulin sensitivity.

Exemplary Formulations

Provided herein are formulations useful for treatment and stabilization of individuals suffering from type II diabetes or at risk of developing type II diabetes.

Provided herein is a formulation comprising: group A components consisting essentially of protein selected from pea protein isolate, sacha inchi protein, hemp protein, rice protein, artichoke protein, chia seed protein, beef protein or combinations thereof; at least one group B component that comprises dandelion extract, milk thistle extract, phospholipids, ginger, taurine, turmeric extract, vitamin C, methionine or combinations thereof; at least one group C component that comprises magnesium, trimethylglycine, glutathione, N-acetyl-cysteine, glutamine, alpha lipoic acid, glycine or combinations thereof; at least one group D component that comprises hesperidin, beet root, enzyme blend, sarsparilla root, bromelain, betaine, methylsulfonylmethane (MSM), choline bitartarate, primrose, inulin, watercress leaf, *Panax ginseng* root extract, selenium, lecithin, or S-anenosylmethionine (SAM-e), thiamine, vitamin B5, niacin, vitamin E, riboflavin, vitamin B6, folate, vitamin B12, biotin, zinc, copper, molybdenum, carotene, calcium, vitamin D, sodium phosphate, vitamin A, calcium, phosphorus, chromium, triglyceride, quercetin, rutin, Marshmallow extract, Jerusalem artichoke tuber, fiber or combinations thereof; and an excipient. In some embodiments, the enzyme blend comprises a lactase, a cellulase, a protease, a lipase, a dismutase, a catalase, or a combination thereof.

Provided herein are formulations useful for treatment and/or stabilization of individuals suffering from type II diabetes or at risk of developing type II diabetes. In some embodiments, provided is a formulation comprising: group A components consisting essentially of protein selected from pea protein isolate, sacha inchi protein, hemp protein, rice protein, artichoke protein, chia seed protein, beef protein or combinations thereof; at least one group B component that comprises dandelion extract, milk thistle extract, phospholipids, ginger, taurine, turmeric extract, vitamin C, methionine or combinations thereof; at least one group C component that comprises magnesium, trimethylglycine, glutathione, N-acetyl-cysteine, *Cordyceps sinensis* extract, glutamine, alpha lipoic acid, glycine or combinations thereof; and an excipient. In some embodiments, the formulation further comprises pea protein isolate and sacha inchi protein. In some embodiments, the formulation further comprises a protein derived from a source which is not pea protein isolate. In some embodiments, the formulation further comprises a protein derived from a source which is not sacha inchi protein.

Further provided is a formulation comprising: group A components consisting essentially of maca, *Cornus officinalis* fruit extract or combinations thereof at least one group B component that comprises berberine, bitter melon extract, *Gymnema sylvestre* leaf extract, banaba, carnitine or combinations thereof; at least one group C component that comprises vitamin C, *Panax ginseng* root extract, Aswagandha root extract, holy basil leaf extract, *Rhodiola rosea* extract, *Eleutherococcus senticosus* extract, vitamin B5, cactus stem extract, phosphatidylserine, vitamin D or combinations thereof; and an excipient. In some embodiments, the formulation further comprises a fish oil formulation. The fish oil formulation may comprise omega-3 at a range of about 15% to about 100%.

Also provided is a formulation comprising: group A components consisting essentially of maca, *Cornus officinalis* fruit extract or combinations thereof; at least one group B component that comprises berberine, bitter melon extract, *Gymnema sylvestre* leaf extract, banaba, or carnitine; at least one group C component that comprises vitamin C, *Panax ginseng* root extract, Aswagandha root extract, holy basil leaf extract, *Rhodiola rosea* extract, *Eleutherococcus senticosus* extract, vitamin B5, cactus stem extract, phosphatidylserine, vitamin D or combinations thereof; at least one group D component that comprises *Cordyceps sinesis* extract, *Gingko biloba* leaf extract, suma root, *Garcinia cambogia* extract, *Rehmannia glutinosa* extract, *Poria cocos* root extract, cinnamon extract, Fenugreek, Guggul, citrimax extract, *salacia oblonga* extract, vitamin E, thiamin, riboflavin, niacin, vitamin B6, folate, vitamin B12, biotin, magnesium, zinc, selenium, manganese, chromium, vanadium, zinc, biotin, alpha lipoic acid, N-acetyl-cysteine, 4-aminobenzoic acid (PABA), choline bitartrate, glutamine, glutathione, protein, fiber, inositol or combinations thereof; and an excipient.

Still further provided is a formulation comprising: group A components consisting essentially of cactus stem extract; at least one group B component that comprises berberine, bitter melon extract, *Gymnema sylvestre* leaf extract, banaba, carnitine or combinations thereof; at least one group C component that comprises *Garcinia cambogia* extract, *Rehmannia glutinosa* extract, *Poria cocos* root extract, cinnamon extract, Fenugreek, Guggul, Vitamin D or combinations thereof; and an excipient.

Additionally provided is a formulation comprising: group A component comprising cactus stem extract; at least one of group B component that comprises berberine, bitter melon extract, *Gymnema sylvestre* leaf extract, banaba, carnitine or combinations thereof; at least one group C component that comprises *Garcinia cambogia* extract, *Rehmannia glutinosa* extract, *Poria cocos* root extract, cinnamon extract, Fenugreek, or Guggul; at least one group D component that comprises vitamin D, vitamin E, thiamin, riboflavin, niacin, vitamin B6, folate, vitamin B12, biotin, vitamin B5, magnesium, zinc, selenium, manganese, chromium, vanadium, alpha lipoic acid, N-acetyl-cysteine, 4-aminobenzoic acid (PABA), choline bitartarate, citrimax extract, taurine, coenzyme Q10, calcium, vitamin K2, vitamin C, protein, fiber, inositol or combinations thereof; and an excipient.

In some embodiments, is a formulation comprising: group A components consisting essentially of at least one protein optionally selected from a list comprising pea protein isolate and sacha inchi protein; at least one group B component that comprises dandelion extract, milk thistle extract, phospholipids, ginger, taurine, turmeric extract, vitamin C, or methionine; at least one group C component that comprises magnesium, trimethylglycine, glutathione, N-acetyl-cysteine, *Cordyceps sinensis* extract, glutamine, alpha lipoic acid, or glycine; and an excipient. In some embodiments, the formulation further comprises pea protein isolate and sacha inchi protein. In some embodiments, the formulation further comprises a protein derived from a source which is not pea protein isolate. In some embodiments, the formulation further comprises a protein derived from a source which is not sacha inchi protein. Provided is a formulation comprising: group A components consisting essentially of at least one protein optionally selected from a list comprising pea protein isolate and sacha inchi protein; at least one group B component that comprises about 5% to about 40% by weight of dandelion extract, about 3% to about 15% by weight of milk thistle extract, about 1% to about 12% by weight of phospholipids, about 1% to about 10% by weight of ginger, about 0.5% to about 8% by weight of taurine, about 0.5% to about 8% by weight of turmeric extract, about 1% to about 8% by weight of vitamin C, or about 1% to about 11% by weight of methionine; at least one group C component that comprises about 10% to about 55% by weight of magnesium, about 1% to about 40% by weight of trimethylglycine, about 0.5% to about 35% by weight of glutathione, about 0.5% to about 30% by weight of N-acetyl-cysteine, about 0.5% to about 6% by weight of *Cordyceps sinensis* extract, about 0.5% to about 6% by weight of glutamine, about 0.5% to about 6% by weight of alpha lipoic acid, or about 0.5% to about 6% by weight of glycine; and an excipient. In some embodiments, a formulation described herein is administered to the subject between about 2 and about 60 days. In some embodiments, the formulation is administered for about 10, 15, 20, 30, 40, 45, 50, or 60 days. In certain further embodiments, the formulation is administered for about 30 days. In some additional embodiments, a formulation described herein may be administered at fixed intervals during administration of a second formulation described herein. The fixed interval may be between about two and about four months. In some embodiments, the fixed interval is about three months.

Provided is a formulation comprising: group A components consisting essentially of maca, *Cornus officinalis* fruit extract, and optionally broad bean; at least one group B component that comprises berberine, bitter melon extract, *Gymnema sylvestre* leaf extract, banaba, or carnitine; at least one group C component that comprises vitamin C, *Panax ginseng* root extract, Aswagandha root extract, holy basil leaf extract, *Rhodiola rosea* extract, *Eleutherococcus senticosus* extract, vitamin B5, cactus stem extract, phosphatidylserine, or vitamin D; and an excipient. In some embodiments, the formulation further comprises a fish oil formulation. The fish oil formulation may comprise omega-3 at a range of about 15% to about 100%. The fish oil formulation may also comprise eicosapentaenoic acid (EPA) at a range of about 5% to about 100%. In some embodiments, the fish oil formulation comprises docosahexaenoic acid (DHA) at a range of about 10% to about 100%. In certain embodiments, a formulation described herein is provided to a subject for a period of time which is from about one month to about sixty months. In some embodiments, the period of time may be from about six months to about thirty six months. In some cases, this period of time is from about twelve months to about twenty four months. In certain cases, the period of time is the time required for the subject to achieve a predetermined change in blood sugar level. In an embodiment, the period of time is the time required for the subject to achieve a predetermined reduction in hemoglobin A1C level.

Provided is a formulation comprising: group A components consisting essentially of maca, *Cornus officinalis* fruit extract, and optionally broad bean; at least one group B component that comprises about 6% to about 18% by weight of berberine, about 0.2% to about 18% by weight of bitter melon extract, about 8% to about 18% by weight of *Gymnema sylvestre* leaf extract, about 0.2% to about 18% by weight of banaba, or about 1% to about 5% by weight of carnitine; at least one group C component that comprises about 2% to about 9% by weight of vitamin C, about 5% to about 21% by weight of *Panax ginseng* root extract, about 4% to about 16% by weight of Aswagandha root extract, about 3% to about 13% by weight of holy basil leaf extract, about 2% to about 10% by weight of *Rhodiola rosea* extract, about 1% to about 7% by weight of *Eleutherococcus senticosus* extract, about 1% to about 7% by weight vitamin B5, about 1% to about 8% by weight of cactus stem extract, about 20% to about 90% by weight of phosphatidylserine, or vitamin D; and an excipient. In some embodiments, the formulation further comprises a fish oil formulation. The fish oil formulation may comprise omega-3 at a range of about 15% to about 100%. The fish oil formulation may also comprise eicosapentaenoic acid (EPA) at a range of about 5% to about 100%. In some embodiments, the fish oil formulation comprises docosahexaenoic acid (DHA) at a range of about 10% to about 100%.

Provided is a formulation comprising: group A components consisting essentially of cactus stem extract and optionally broad bean; at least one group B component that comprises berberine, bitter melon extract, *Gymnema sylvestre* leaf extract, banaba, or carnitine; at least one group C component that comprises *Garcinia cambogia* extract, *Rehmannia glutinosa* extract, *Poria cocos* root extract, cinnamon extract, Fenugreek, Guggul, or Vitamin D; and an excipient. In some embodiments is provided a formulation comprising: group A components cactus stem extract and optionally broad bean; group B components comprising one or more of about 6% to about 28% by weight of berberine, about 0.2% to about 18% by weight of bitter melon extract, about 8% to about 18% by weight of *Gymnema sylvestre* leaf extract, about 0.2% to about 18% by weight of banaba, and about 2% to about 5% by weight of carnitine; group C components comprising one or more of *Garcinia cambogia* extract, *Rehmannia glutinosa* extract, *Poria cocos* root extract, cinnamon extract, Fenugreek, and Guggul, wherein the concentration of each of the group C components is from about 0.2% to about 0.6% by weight; vitamin D; and an excipient. In certain cases, the formulation is provided to a subject for a period of time which is from about 1 month to about the remaining lifetime of the subject.

In some embodiments is a formulation described herein, wherein dandelion extract is dandelion root extract. In some embodiments is a formulation described herein, wherein the phospholipids comprise about 40% phosphatidylcholine. In some embodiments is a formulation described herein, wherein the turmeric extract comprises about 95% curcumin. In some embodiments is a formulation described herein, wherein milk thistle extract is milk thistle seed extract comprises about 80% silymarin. In some embodiments is a formulation described herein, optionally further comprising a gotu kola extract, which is optionally a gotu kola leaf extract. In some embodiments is a formulation described herein, wherein vitamin C comprises L-ascorbic acid, calcium ascorbate, or a combination thereof. In some embodiments is a formulation described herein, wherein magnesium is magnesium citrate. In some embodiments is a formulation described herein, wherein glutathione comprises L-glutathione, S-acetyl L-glutathione, or a combination thereof. In some embodiments is a formulation described herein, wherein N-acetyl-cysteine is N-Acetyl L-cysteine. In some embodiments is a formulation described herein, wherein *Cordyceps sinensis* extract comprises about 7% cordycepic acid. In some embodiments is a formulation described herein, wherein glutamine is L-glutamine. In some embodiments is a formulation described herein, wherein alpha lipoic acid is alpha R-lipoic acid. In some embodiments is a formulation described herein, wherein glycine is L-glycine. In some embodiments is a formulation described herein, further comprising at least one group D component that comprises hesperidin, beet root, enzyme blend, sarsaparilla root, bromelain, betaine, methylsulfonylmethane (MSM), choline bitartarate, luo han guo, *stevia* extract rebaudioside, primrose, inulin, watercress leaf, *Panax ginseng* root extract, selenium, or S-anenosylmethionine (SAM-e). In some embodiments is a formulation described herein, wherein luo han guo comprises about 40% mogrosides. In some embodiments is a formulation described herein, wherein the *stevia* extract rebaudioside is *stevia* extract 97% rebaudioside. In some embodiments is a formulation described herein, wherein the primrose is evening primrose oil powder. In some embodiments is a formulation described herein, wherein hesperidin is hesperidin complex. In some embodiments is a formulation described herein, wherein beet root is beet root powder. In some embodiments is a formulation described herein, wherein the enzyme blend comprises a lactase, a cellulase, a protease, a lipase, a dismutase, a catalase, or a combination thereof. In some embodiments is a formulation described herein, wherein betaine is betaine hydrochloride. In some embodiments is a formulation described herein, wherein choline is choline bitartarate. In some embodiments is a formulation described herein, wherein the watercress leaf is watercress leaf powder. In some embodiments is a formulation described herein, wherein selenium is L-selenomethionine. In some embodiments is a formulation described herein, further comprising at least one group E component that comprises thiamine, vitamin B5, niacin, vitamin E, vitamin B6, folate, vitamin B12, biotin, zinc, copper, molybdenum, carotene, calcium, vitamin D, sodium phosphate, triglyceride, quercetin, rutin, Marshmallow extract, or Jerusalem artichoke tuber.

In some embodiments is a formulation described herein, wherein thiamine is optionally benfotiamine. In some embodiments is a formulation described herein, wherein vitamin B5 comprises at least one of pantothenic acid, pantethine, d-calcium pantothenate, or a combination thereof. In some embodiments is a formulation described herein, wherein niacin comprises at least one of niacinamide, nicotinic acid, or a combination thereof. In some embodiments is a formulation described herein, wherein vitamin E is d-alpha tocopherol succinate. In some embodiments is a formulation described herein, optionally further comprising riboflavin, wherein said riboflavin is optionally riboflavin-5'-phosphate. In some embodiments is a formulation described herein, wherein vitamin B6 comprises at least one of pyridoxal-5-phosphate, pyridoxine HCl, or a combination thereof. In some embodiments is a formulation described herein, wherein folate is L-5-methyltetrahydrofolate.

In some embodiments is a formulation described herein, wherein vitamin B12 is methylcobalamin. In some embodiments is a formulation described herein, wherein zinc is zinc glycinate. In some embodiments is a formulation described herein, wherein copper is copper gluconate. In some embodiments is a formulation described herein, wherein molybdenum is molybdenum amino acid chelate. In some embodiments is a formulation described herein, wherein carotene is beta carotene. In some embodiments is a formulation described herein, wherein calcium is calcium ascorbate. In some embodiments is a formulation described herein, wherein vitamin D is vitamin D3. In some embodiments is a formulation described herein, wherein sodium phosphate is disodium phosphate. In some embodiments is a formulation described herein, wherein the triglyceride is a triglyceride comprising about 6-12 carbon fatty acid esters.

In some embodiments is a formulation described herein, wherein quercetin is quercetin dihydrate. In some embodiments is a formulation described herein, wherein Marshmallow extract is Marshmallow root extract. In some embodiments is a formulation described herein, wherein the concentration of pea protein isolate in the formulation is from about 5% to about 70% by weight. In some embodiments is a formulation described herein, wherein the concentration of sacha inchi protein in the formulation is from about 0.5% to about 10% by weight. In some embodiments is a formulation described herein, wherein the concentration of dandelion extract in the formulation is from about 5% to about 40% by weight. In some embodiments is a formulation described herein, wherein the concentration of milk thistle extract in the formulation is from about 3% to about 15% by weight. In some embodiments is a formulation described herein, wherein the concentration of phospholipids in the formulation is from about 1% to about 12% by weight. In some embodiments is a formulation described herein, wherein the concentration of ginger in the formulation is from about 1% to about 10% by weight. In some embodiments is a formulation described herein, wherein the concentration of taurine in the formulation is from about 0.5% to about 8% by weight.

In some embodiments is a formulation described herein, wherein the concentration of turmeric extract in the formulation is from about 0.5% to about 8% by weight. In some embodiments is a formulation described herein, wherein the optionally comprising gotu kola extract in a concentration up to about 8% by weight. In some embodiments is a formulation described herein, wherein the concentration of vitamin C in the formulation is from about 1% to about 8% by weight. In some embodiments is a formulation described herein, wherein the concentration of methionine in the formulation is from about 1% to about 11% by weight. In some embodiments is a formulation described herein, wherein the concentration of magnesium in the formulation is from about 10% to about 55% by weight. In some embodiments is a formulation described herein, wherein the concentration of trimethylglycine in the formulation is from about 1% to about 40% by weight. In some embodiments is a formulation described herein, wherein the concentration of glutathione in the formulation is from about 0.5% to about 35% by weight. In some embodiments is a formulation described herein, wherein the concentration of N-acetylcysteine in the formulation is from about 0.5% to about 30% by weight. In some embodiments is a formulation described herein, wherein the concentration of *Cordyceps sinensis* extract in the formulation is from about 0.5% to about 6% by weight. In some embodiments is a formulation described herein, wherein the concentration of glutamine in the formulation is from about 0.5% to about 6% by weight. In some embodiments is a formulation described herein, wherein the concentration of alpha lipoic acid in the formulation is from about 0.5% to about 6% by weight. In some embodiments is a formulation described herein, wherein the concentration of glycine in the formulation is from about 0.5% to about 6% by weight.

In some embodiments is a formulation described herein, wherein the excipient comprises gelatin, cellulose, medium-chain triglyceride (MCT) oil, silicon dioxide, stearic acid, xanthan gum, potassium sorbate, turmeric powder, primrose oil, lemon oil, or combinations thereof. In some embodiments is a formulation described herein, wherein the formulation is in a powder form, a semi-solid form, a liquid form, an emulsion form, or a combination thereof.

In some embodiments is a formulation described herein, further comprising at least one component that comprises hesperidin, beet root, enzyme blend, sarsaparilla root, bromelain, betaine, methylsulfonylmethane (MSM), choline bitartarate, luo han guo, *stevia* extract rebaudioside, primrose, inulin, watercress leaf, *Panax ginseng* root extract, selenium, or S-anenosylmethionine (SAM-e). In some embodiments is a formulation described herein, further comprising at least one component that comprises thiamine, vitamin B5, niacin, vitamin E, riboflavin, vitamin B6, folate, vitamin B12, biotin, zinc, copper, molybdenum, carotene, calcium, vitamin D, sodium phosphate, triglyceride, quercetin, rutin, Marshmallow extract, or Jerusalem artichoke tuber. In some embodiments is a formulation described herein, wherein the phospholipids comprise about 40% phosphatidylcholine. In some embodiments is a formulation described herein, wherein the turmeric extract comprises about 95% curcumin. In some embodiments is a formulation described herein, wherein milk thistle extract is milk thistle seed extract comprising about 80% silymarin.

In some embodiments is a formulation described herein, further comprising gotu kola extract, wherein optionally said gotu kola extract is gotu kola leaf extract. In some embodiments is a formulation described herein, wherein vitamin C comprises L-ascorbic acid, calcium ascorbate, or a combination thereof. In some embodiments is a formulation described herein, wherein glutathione comprises L-glutathione, S-acetyl L-glutathione, or a combination thereof. In some embodiments is a formulation described herein, wherein *Cordyceps sinensis* extract comprises about 7% cordycepic acid. In some embodiments is a formulation described herein, wherein luo han guo comprises about 40% mogrosides.

In some embodiments is a formulation described herein, wherein the *stevia* extract rebaudioside is *stevia* extract 97% rebaudioside. In some embodiments is a formulation described herein, wherein the concentration of pea protein isolate in the formulation is from about 5% to about 70% by weight. In some embodiments is a formulation described herein, wherein the concentration of sacha inchi protein in the formulation is from about 0.5% to about 10% by weight.

In an embodiment is a formulation described herein, wherein berberine is berberine hydrochloride. In some embodiments is a formulation described herein, wherein carnitine is carnitine tartrate. In some embodiments is a formulation described herein, wherein carnitine is L-carnitine L-tartrate. In some embodiments is a formulation described herein, wherein the *Cordyceps sinesis* extract is a *Cordyceps sinesis* mycelium extract. In some embodiments is a formulation described herein, wherein vitamin C is L-ascorbic acid. In some embodiments is a formulation described herein, wherein vitamin B5 comprises at least one of pantothenic acid, pantethine, d-calcium pantothenate, or a combination thereof. In some embodiments is a formulation described herein, wherein the phosphatidylserine is a phospholipid complex supplement. In an embodiment is a formulation described herein, wherein vitamin D is a powder. In some embodiments is a formulation described herein, further comprising at least one component that comprises *Cordyceps sinesis* extract, *Gingko biloba* leaf extract, suma root, *Garcinia cambogia* extract, *Rehmannia glutinosa* extract, *Poria cocos* root extract, cinnamon extract, Fenugreek, or Guggul.

In some embodiments is a formulation described herein, wherein *Rehmannia glutinosa* extract is *Rehmania glutinosa* rhizome extract. In some embodiments is a formulation described herein, wherein the *Rehmania glutinosa* rhizome extract is a *Rehmania glutinosa* rhizome 5:1 extract.

In some embodiments is a formulation described herein, further comprising a fish oil formulation. In some embodiments is a formulation described herein, wherein the fish oil formulation comprises omega-3 at a range of about 15% to about 100%. In some embodiments is a formulation described herein, wherein the fish oil formulation comprises eicosapentaenoic acid (EPA) at a range of about 5% to about 100%. In some embodiments the fish oil formulation comprises docosahexaenoic acid (DHA) at a range of about 10% to about 100%. In some embodiments is a formulation described herein, wherein the fish oil formulation is in a powder form. In some embodiments is a formulation described herein, wherein the fish oil formulation is in a liquid form. In some embodiments is a formulation described herein, wherein the fish oil formulation is in an emulsion form. In some embodiments is a formulation described herein, wherein the fish oil formulation further comprises one or more of citric acid, luo han guo, sodium citrate, calcium glycinate amino acid complex, magnesium glycinate, zinc glycinate chelate, zinc L-monomethionine, pyridoxal-5-phosphate drum, niacin, molybdenum amino acid chelate, taurine, lecithin, glycerine, and vitamin E.

In some embodiments is a formulation described herein, further comprising at least one component that comprises one or more of vitamin E, thiamin, riboflavin, niacin, vitamin B6, folate, vitamin B12, biotin, magnesium, zinc, selenium, manganese, chromium, vanadium, alpha lipoic acid, N-acetyl-cysteine, 4-aminobenzoic acid (PABA), choline bitartrate, or inositol. In some embodiments is a formulation described herein, wherein the concentration of berberine hydrochloride in the formulation is from about 6% to about 28% by weight. In some embodiments is a formulation described herein, wherein the concentration of bitter melon extract in the formulation is from about 0.2% to about 18% by weight. In some embodiments is a formulation described herein, wherein the concentration of *Gymnema sylvestre* leaf extract in the formulation is from about 8% to about 18% by weight. In some embodiments is a formulation described herein, wherein the concentration of banaba in the formulation is from about 0.2% to about 18% by weight. In some embodiments is a formulation described herein, wherein the concentration of cactus stem extract in the formulation is from about 1% to about 8% by weight. In some embodiments is a formulation described herein, wherein the concentration of L-carnitine L-tartrate in the formulation is from about 1% to about 5% by weight. In some embodiments is a formulation described herein, wherein the concentration of *Garcinia cambogia* extract in the formulation is from about 0.1% to about 1% by weight. In some embodiments is a formulation described herein, wherein the concentration of *Rehmannia glutinosa* extract in the formulation is from about 0.1% to about 3% by weight. In some embodiments is a formulation described herein, wherein the concentration of *Poria cocos* root extract in the formulation is from about 0.1% to about 1% by weight. In some embodiments is a formulation described herein, wherein the concentration of cinnamon extract in the formulation is from about 0.1% to about 1% by weight. In some embodiments is a formulation described herein, wherein the concentration of Fenugreek extract in the formulation is from about 0.1% to about 1% by weight.

In some embodiments is a formulation described herein, wherein the concentration of Guggul extract in the formulation is from about 0.1% to about 1% by weight. In some embodiments is a formulation described herein, optionally comprising broad bean extract which is optionally in a concentration from about 0.05% to about 0.25% by weight. In some embodiments is a formulation described herein, wherein the concentration of *Cordyceps sinesis* extract in the formulation is from about 0.5% to about 3% by weight. In some embodiments is a formulation described herein, wherein the concentration of maca in the formulation is from about 0.5% to about 3% by weight. In some embodiments is a formulation described herein, wherein the concentration of *Gingko biloba* leaf extract in the formulation is from about 0.5% to about 3% by weight. In some embodiments is a formulation described herein, wherein the concentration of suma root extract in the formulation is from about 0.5% to about 3% by weight. In some embodiments is a formulation described herein, wherein the concentration of *Cornus officinalis* fruit extract in the formulation is from about 0.5% to about 3% by weight.

In some embodiments is a formulation described herein, wherein the concentration of vitamin C in the formulation is from about 2% to about 9% by weight. In some embodiments is a formulation described herein, wherein the concentration of *Panax ginseng* root extract in the formulation is from about 5% to about 21% by weight. In some embodiments is a formulation described herein, wherein the concentration of Aswagandha root extract in the formulation is from about 4% to about 16% by weight. In some embodiments is a formulation described herein, wherein the concentration of holy basil leaf extract in the formulation is from about 3% to about 13% by weight. In some embodiments is a formulation described herein, wherein the concentration of *Rhodiola rosea* extract in the formulation is from about 2% to about 10% by weight. In some embodiments is a formulation described herein, wherein the concentration of *Eleutherococcus senticosus* extract in the formulation is from about 1% to about 7% by weight.

In some embodiments is a formulation described herein, wherein the concentration of vitamin B5 in the formulation is from about 1% to about 7% by weight. In some embodiments is a formulation described herein, wherein the concentration of phosphatidylserine is from about 20% to about 90% by weight. In some embodiments is a formulation described herein, wherein the excipient comprises gelatin, cellulose, medium-chain triglyceride (MCT) oil, silicon dioxide, stearic acid, or combinations thereof.

In some embodiments is a formulation described herein, optionally comprising broad bean. In some embodiments is a formulation described herein, wherein berberine is berberine hydrochloride. In some embodiments is a formulation described herein, wherein carnitine is carnitine tartrate. In some embodiments is a formulation described herein, wherein carnitine is L-carnitine L-tartrate. In some embodiments is a formulation described herein, wherein *Rehmannia glutinosa* extract is *Rehmania glutinosa* rhizome extract. In some embodiments is a formulation described herein, wherein the *Rehmania glutinosa* rhizome extract is a *Rehmania glutinosa* rhizome 5:1 extract. In some embodiments is a formulation described herein, wherein vitamin D is a powder. In some embodiments is a formulation described herein, further comprising at least one component that comprises vitamin E, thiamin, riboflavin, niacin, vitamin B6, folate, vitamin B12, biotin, vitamin B5, magnesium, zinc, selenium, manganese, chromium, vanadium, alpha lipoic acid, N-acetyl-cysteine, 4-aminobenzoic acid (PABA), choline bitartarate, or inositol. In some embodiments is a formulation described herein, wherein vitamin E is d-alpha tocopherol succinate. In some embodiments is a formulation described herein, wherein thiamin is at least one of benfotiamine and thiamine HCl. In some embodiments is a formulation described herein, wherein riboflavin is roboflavin-5'-phosphate. In some embodiments is a formulation described herein, wherein niacin comprises at least one of niacinamide, nicotinic acid, or a combination thereof. In some embodiments is a formulation described herein, wherein vitamin B6 is at least one of pyridoxal-5-phospate and pyridoxine HCl. In some embodiments is a formulation described herein, wherein folate is L-5-metyltetrahydrofolate.

In some embodiments is a formulation described herein, wherein vitamin B12 is cyanococbalamin. In some embodiments is a formulation described herein, wherein vitamin B5 comprises at least one of pantothenic acid, d-calcium pantothenate, pantethine, or a combination thereof. In some embodiments is a formulation described herein, wherein magnesium is magnesium citrate.

In some embodiments is a formulation described herein, wherein zinc is zinc glycinate. In some embodiments is a formulation described herein, wherein selenium is L-selenomethionine. In some embodiments is a formulation described herein, wherein manganese is manganese gluconate. In some embodiments is a formulation described herein, wherein chromium is chromium niacin complex. In some embodiments is a formulation described herein, wherein vanadium is vanadium sulfate. In some embodiments is a formulation described herein, wherein alpha lipoic acid is alpha R-lipoic acid. In some embodiments is a formulation described herein, wherein N-acetyl-cysteine is N-Acetyl L-cysteine. In some embodiments is a formulation described herein, wherein the concentration of berberine hydrochloride in the formulation is from about 6% to about 28% by weight. In some embodiments is a formulation described herein, wherein the concentration of bitter melon extract in the formulation is from about 0.2% to about 18% by weight. In some embodiments is a formulation described herein, wherein the concentration of *Gymnema sylvestre* leaf extract in the formulation is from about 8% to about 18% by weight. In some embodiments is a formulation described herein, wherein the concentration of banaba in the formulation is from about 0.2% to about 18% by weight. In some embodiments is a formulation described herein, wherein the concentration of cactus stem extract in the formulation is from about 3% to about 8% by weight. In some embodiments is a formulation described herein, wherein the concentration of L-carnitine L-tartrate in the formulation is from about 2% to about 5% by weight.

In some embodiments is a formulation described herein, wherein the concentration of *Garcinia cambogia* extract in the formulation is from about 0.2% to about 0.6% by weight. In some embodiments is a formulation described herein, wherein the concentration of *Rehmannia glutinosa* extract in the formulation is from about 0.2% to about 0.6% by weight.

In some embodiments is a formulation described herein, wherein the concentration of *Poria cocos* root extract in the formulation is from about 0.2% to about 0.6% by weight. In some embodiments is a formulation described herein, wherein the concentration of cinnamon extract in the formulation is from about 0.2% to about 0.6% by weight. In some embodiments is a formulation described herein, wherein the concentration of Fenugreek in the formulation is from about 0.2% to about 0.6% by weight. In some embodiments is a formulation described herein, wherein the concentration of Guggul in the formulation is from about 0.2% to about 0.6% by weight.

In some embodiments is a formulation described herein, optionally further comprising broad bean powder in a concentration from about 0.2% to about 0.6% by weight. In some embodiments is a formulation described herein, wherein the excipient comprises gelatin, cellulose, medium-chain triglyceride (MCT) oil, silicon dioxide, stearic acid, xanthan gum, potassium sorbate, turmeric powder, primrose oil, lemon oil, or combinations thereof.

In some embodiments, formulations that comprise ingredients at additional concentrations are also contemplated. In some instances, the concentration of dandelion extract is from about 5% to about 40%, about 6% to about 36%, about 8% to about 35%, about 9% to about 34%, or about 10% to about 30% by weight.

In some instances, the concentration of milk thistle extract is from about 1% to about 20%, about 3% to about 15%, about 5% to about 12%, or about 8% to about 10% by weight.

In some instances, the concentration of phospholipids is from about 1% to about 15%, about 1% to about 12%, about 2% to about 10%, or about 5% to about 8% by weight. In some cases, the concentration of ginger is from about 0.5% to about 15%, about 1% to about 10%, about 2% to about 8%, or about 3% to about 6% by weight. In some instances, the concentration of taurine is from about 0.5% to about 10%, about 1% to about 8%, about 2% to about 7%, or about 3% to about 6% by weight. In some instances, the concentration of curcumin is from about 0.5% to about 10%, about 1% to about 8%, about 2% to about 7%, or about 3% to about 6% by weight.

In some embodiments, the concentration of turmeric extract is from about 0.5% to about 10%, about 1% to about 8%, about 2% to about 6%, or about 3% to about 5% by weight. In some instances, the concentration of vitamin C about 1% to about 10%, about 1% to about 8%, about 2% to about 7%, or about 3% to about 6% by weight. In some instances, the concentration of vitamin B is from about 0.5% to about 10%, about 1% to about 10%, about 1% to about 8%, about 2% to about 7%, or about 3% to about 6% by weight. In some embodiments, the concentration of methionine is from about 0.5% to about 15%, about 1% to about 11%, % to about 10%, about 1% to about 8%, about 2% to about 7%, or about 3% to about 6% by weight.

In some cases, the concentration of magnesium is from about 5% to about 60%, about 10% to about 55%, about 12% to about 50%, or about 15% to about 40% by weight.

In some instances, the concentration of trimethylglycine is from about 0.5% to about 50%, about 1% to about 40%, about 2% to about 35%, about 3% to about 30%, or about 5% to about 20% by weight.

In some instances, the concentration of glutathione is from about 0.5% to about 40%, about 0.5% to about 35%, about 1% to about 30%, about 6% to about 25%, or about 8% to about 20% by weight.

In some embodiments, the concentration of N-acetyl-cysteine is from about 0.5% to about 40%, about 0.5% to about 35%, about 1% to about 30%, about 6% to about 25%, or about 8% to about 20% by weight.

In some instances, the concentration of *Cordyceps sinensis* extract is from about 0.5% to about 6%, about 0.8% to about 5%, about 1% to about 4%, or about 1.2% to about 3% by weight.

In some cases, the concentration of glutamine is from about 0.5% to about 6%, about 0.8% to about 5%, about 1% to about 4%, or about 1.2% to about 3% by weight.

In some instances, the concentration of alpha lipoic acid is from about 0.5% to about 6%, about 0.8% to about 5%, about 1% to about 4%, or about 1.2% to about 3% by weight.

In some instances, the concentration of glycine is from about 0.5% to about 6%, about 0.8% to about 5%, about 1% to about 4%, or about 1.2% to about 3% by weight.

In some instances, the concentration of selenium is from about 0.1% to about 5% by weight. In some instances, the concentration of selenium is about 0.2%, 0.4%, 0.6%, 0.8%, 1%, 1.2%, 1.4%, 1.6%, 1.8%, 2%, 3%, 4%, or 5% by weight.

In some embodiments, the concentration of SAMe is from about 0.1% to about 5% by weight. In some instances, the concentration of selenium is about 0.2%, 0.4%, 0.6%, 0.8%, 1%, 1.2%, 1.4%, 1.6%, 1.8%, 2%, 3%, 4%, or 5% by weight.

In some instances, the concentration of pea protein isolate is from about 10% to about 60%, about 11% to about 57%, about 15% to about 55%, or about 20% to about 40% by weight.

In some instances, the concentration of sacha inchi protein is from about 0.5% to about 10%, about 1% to about 10%, about 1% to about 8%, about 2% to about 7%, or about 3% to about 6% by weight.

In some embodiments, the concentration of maca is from about 0.5% to about 3%. In some embodiments, the concentration of maca is about 0.6%, 0.7%, 0.8%, 0.9%, 1%, 1.5%, 2%, 2.5%, or 3% by weight.

In some instances, the concentration of *Cornus officinalis* is from about 0.5% to about 3%. In some embodiments, the concentration of *Cornus officinalis* is about 0.6%, 0.7%, 0.8%, 0.9%, 1%, 1.5%, 2%, 2.5%, or 3% by weight.

In some cases, the concentration of berberine is from about 3% to about 40%, about 5% to about 30%, about 6% to about 28%, about 6% to about 18% by weight.

In some instances, the concentration of bitter melon extract is from about 0.1% to about 20%, about 0.2% to about 18%, about 0.5% to about 15%, about 1% to about 12%, or about 4% to about 8% by weight.

In some instances, the concentration of *Gymnema sylvestre* leaf extract is from about 3% to about 30%, about 5% to about 20%, about 6% to about 18%, about 8% to about 18%, or about 10% to about 15% by weight.

In some instances, the concentration of banaba is from about 0.1% to about 20%, about 0.2% to about 18%, about 0.5% to about 15%, about 1% to about 12%, or about 4% to about 8% by weight.

In some cases, the concentration of carnitine is from about 1% to about 5% or about 2% to about 5% by weight. In some instances, the concentration of carnitine is about 2%, 3%, or 4%.

In some instances, the concentration of *Panax ginseng* root extract is from about 3% to about 30%, about 5% to about 21%, about 6% to about 18%, or about 8% to about 15% by weight.

In some instances, the concentration of Aswagandha root extract is from about 1% to about 30%, about 2% to about 20%, about 4% to about 16%, or about 6% to about 12% by weight.

In some instances, the concentration of holy basil leaf extract is from about 1% to about 15%, about 3% to about 13%, or about 4% to about 10% by weight.

In some instances, the concentration of *Rhodiola rosea* extract is from about 1% to about 15%, about 2% to about 10%, or about 3% to about 8% by weight.

In some cases, the concentration of *Eleutherococcus senticosus* extract is from about 1% to about 10%, or about 1% to about 7% by weight.

In some instances, the concentration of cactus stem extract is from about 1% to about 15%, or about 1% to about 8% by weight.

In some embodiments, the concentration of phosphatidylserine is from about 20% to about 90%, about 30% to about 80%, or about 40% to about 60% by weight.

In some instances, the concentration of broad bean is from about 0.05% to about 0.3% or from about 0.1% to about 0.2% by weight.

In some embodiments, the concentration of *Garcinia cambogia* extract is from about 0.1% to about 1%, about 0.1% to about 0.7%, about 0.2% to about 0.6%, or about 0.4% to about 0.6% by weight.

In some instances, the concentration of *Rehmannia glutinosa* extract is from about 0.1% to about 1%, about 0.1% to about 0.7%, about 0.2% to about 0.6%, or about 0.4% to about 0.6% by weight.

In some embodiments, the concentration of *Poria cocos* root extract is from about 0.1% to about 1%, about 0.1% to about 0.7%, about 0.2% to about 0.6%, or about 0.4% to about 0.6% by weight.

In some instances, the concentration of cinnamon extract is from about 0.1% to about 1%, about 0.1% to about 0.7%, about 0.2% to about 0.6%, or about 0.4% to about 0.6% by weight.

In some cases, the concentration of Fenugreek is from about 0.1% to about 1%, about 0.1% to about 0.7%, about 0.2% to about 0.6%, or about 0.4% to about 0.6% by weight.

In some embodiments, the concentration of Guggul is from about 0.1% to about 1%, about 0.1% to about 0.7%, about 0.2% to about 0.6%, or about 0.4% to about 0.6% by weight.

In some embodiments, the concentration of omega-3 is from about 15% to about 100%, about 20% to about 90%, or about 25% to about 80%. In some instances, the concentration of omega-3 is about 30%, 35%, 40%, 45%, 50%, 55%, 60%, 65%, 70%, or 75%. In some cases, the omega-3 concentration is calculated based on the concentration of eicosapentaenoic acid (EPA) and/or docosahexaenoic acid (DHA). In some instances, the concentration of EPA is from about 15% to about 100%, about 20% to about 90%, or about 25% to about 80%. In some instances, the concentration of EPA is about 30%, 35%, 40%, 45%, 50%, 55%, 60%, 65%, 70%, or 75%. In some embodiments, the concentration of DHA is from about 15% to about 100%, about 20% to about 90%, or about 25% to about 80%. In some embodiments, the concentration of DHA is about 30%, 35%, 40%, 45%, 50%, 55%, 60%, 65%, 70%, or 75%.

In some embodiments, at least one formulation disclosed herein is suitable for reducing the need for insulin administration. In some embodiments, at least one formulation disclosed herein is used for hippocampus rehabilitation. In some embodiments, at least one formulation disclosed herein is suitable for supporting, controlling, restoring, maintaining or enhancing blood sugar metabolism. In some embodiments, at least one formulation disclosed herein is suitable for stabilizing or reducing hemoglobin A1C levels. In some embodiments, at least one formulation disclosed herein is suitable for supporting, controlling, restoring, maintaining or enhancing liver function in a subject. In some embodiments, at least one formulation disclosed herein is suitable for supporting, controlling, restoring, maintaining enhancing normal liver function in a subject. In some embodiments, at least one formulation disclosed herein is suitable for supporting, controlling, restoring, maintaining or enhancing gall bladder function in a subject. In some embodiments, at least one formulation disclosed herein is suitable for supporting, controlling, restoring, maintaining or enhancing liver detoxification in a subject. In some embodiments, at least one formulation disclosed herein is suitable for supporting, controlling, restoring, maintaining or enhancing the immune system in a subject. In some embodiments, at least one formulation disclosed herein is suitable for supporting, controlling, restoring, maintaining or enhancing healthy brain function in a subject. In some embodiments, at least one formulation disclosed herein is suitable for supporting, controlling, restoring, maintaining or enhancing digestion in a subject. In some embodiments, at least one formulation disclosed herein is suitable for supporting, controlling, restoring, maintaining or enhancing platelet activity in a subject.

In some embodiments, at least one formulation disclosed herein is suitable for supporting, controlling, restoring, maintaining or enhancing blood sugar metabolism. In some embodiments, at least one formulation disclosed herein is suitable for supporting, controlling, restoring, maintaining or enhancing blood sugar in a subject with insufficient insulin. In some embodiments, at least one formulation disclosed herein is suitable for supporting, controlling, restoring, maintaining or enhancing liver function. In some embodiments, at least one formulation disclosed herein is suitable for supporting, controlling, restoring, maintaining or enhancing normal cholesterol level. In some embodiments, at least one formulation disclosed herein is suitable for supporting, controlling, restoring, maintaining or enhancing red blood cell formation. In some embodiments, at least one formulation disclosed herein is suitable for supporting, controlling, restoring, maintaining or enhancing a healthy salt balance within the body fluid. In some embodiments, at least one formulation disclosed herein is suitable for supporting, controlling, restoring, maintaining or enhancing gastrointestinal health. In some embodiments, at least one formulation disclosed herein is suitable for supporting, controlling, restoring, maintaining or enhancing gall bladder function. In some embodiments, at least one formulation disclosed herein is suitable for supporting, controlling, restoring, maintaining or enhancing liver detoxification. In some embodiments, at least one formulation disclosed herein is suitable for supporting, controlling, restoring, maintaining or enhancing the immune system. In some embodiments, at least one formulation disclosed herein is suitable for supporting, controlling, restoring, maintaining or enhancing a healthy brain function. In some embodiments, at least one formulation disclosed herein is suitable for supporting, controlling, restoring, maintaining or enhancing digestion. In some embodiments, at least one formulation disclosed herein is suitable for supporting, controlling, restoring, maintaining or enhancing platelet activity. In some embodiments, at least one formulation disclosed herein is suitable for supporting, controlling, restoring, maintaining or enhancing healthy adrenal feedback loop function. In some embodiments, at least one formulation disclosed herein is suitable for supporting, controlling, restoring, maintaining or enhancing a normal sleep pattern. In some embodiments, at least one formulation disclosed herein formulation is suitable for supporting, controlling, restoring, maintaining or enhancing mental alertness or wakefulness. In some embodiments, at least one formulation disclosed herein formulation is suitable for supporting, controlling, restoring, maintaining or enhancing normal bone density. In some embodiments, at least one formulation disclosed herein formulation is suitable for supporting, controlling, restoring, maintaining or enhancing hormonal balance. In some embodiments, at least one formulation is suitable for supporting, controlling, restoring, maintaining or enhancing cognitive function. In some embodiments, at least one formulation is suitable for supporting, controlling, restoring, maintaining or enhancing thyroid function. In some embodiments, at least one formulation is suitable for supporting, controlling, restoring, maintaining or enhancing normal menstruation. In some embodiments, at least one formulation is suitable for supporting, controlling, restoring, maintaining or enhancing joint health. In some embodiments, at least one formulation is suitable for supporting, controlling, restoring, maintaining or enhancing insulin receptor function. In some embodiments, at least one formulation is suitable for supporting, controlling, restoring, maintaining or enhancing healthy arterial wall. In some embodiments, at least one formulation is suitable for supporting, controlling, restoring, maintaining or enhancing a healthy heart function. In some embodiments, at least one formulation is suitable for supporting, controlling, restoring, maintaining or enhancing DNA repair function. In some embodiments, at least one formulation is suitable for supporting, controlling, restoring, maintaining or enhancing dopamine production and function.

In some embodiments, at least one formulation disclosed herein is suitable for supporting, controlling, restoring, maintaining or enhancing the health of those suffering from diabetes (or complication from diabetes) or those who are predisposed to pre-diabetes. In some embodiments, at least one formulation disclosed herein is suitable for supporting, controlling, restoring, maintaining or enhancing the health of those concerned with maintaining proper blood sugar control or those who currently have normal blood sugar but who have a history of blood sugar control problem.

In some embodiments, at least one formulation disclosed herein is suitable for supporting, controlling, restoring, maintaining or enhancing natural liver function, natural blood sugar metabolism, natural blood sugar levels, glycemic control, natural insulin response to glucose load, insulin health, natural iron and sugar utilization, peripheral glucose utilization, natural cellular uptake of glucose, secretions of insulin and glucagon, natural glucose tolerance, natural insulin receptor site sensitivity, or the activity of glucokinase.

In some embodiments, at least one formulation disclosed herein is suitable for supporting, controlling, restoring, maintaining or enhancing organ health. In some embodiments, at least one formulation disclosed herein is suitable for supporting, controlling, restoring, maintaining or enhancing the health of the circulatory system, eyes, ears, skin, mouth (oral), soft tissue, scalp, skeletal tissue, cartilage, connective tissue, liver, kidney, gall bladder, muscle, bone, joint, hair, nails, musculoskeletal, or mucous membranes.

In some embodiments, at least one formulation disclosed herein is suitable for supporting, controlling, restoring, maintaining or enhancing natural bone growth, natural growth and repair of tissues, gene expression, cellular repair, or health and integrity of cellular tissue.

In some embodiments, at least one formulation disclosed herein is suitable for supporting, controlling, restoring, maintaining or enhancing reproductive health. In some embodiments, at least one formulation disclosed herein is suitable for supporting, controlling, restoring, maintaining or enhancing female reproductive health, male reproductive health, menstruation health, or male sexual function health.

In some embodiments, at least one formulation disclosed herein is suitable for supporting, controlling, restoring, maintaining or enhancing hormone health. In some embodiments, at least one formulation disclosed herein is suitable for supporting, controlling, restoring, maintaining or enhancing hormone health in a subject suffering from Polycystic Ovarian Syndrome (PCOS). In some embodiments, at least one formulation disclosed herein is suitable for supporting, controlling, restoring, maintaining or enhancing adrenal function or adrenal hormones.

In some embodiments, at least one formulation disclosed herein is suitable for supporting, controlling, restoring, maintaining or enhancing heart and cardiovascular health. In some embodiments, at least one formulation disclosed herein is suitable for supporting, controlling, restoring, maintaining or enhancing healthy red blood cells, natural white blood cell levels, natural heme production, small blood vessel health, healthy blood pressure levels, or platelet function.

In some embodiments, at least one formulation disclosed herein is suitable for supporting, controlling, restoring, maintaining or enhancing healthy cholesterol levels. In some embodiments, at least one formulation disclosed herein is suitable for supporting, controlling, restoring, maintaining or enhancing triglyceride levels, natural breakdown of fats, or natural biliary levels. In some embodiments, at least one formulation disclosed herein is suitable for supporting, controlling, restoring, maintaining or enhancing digestive health. In some embodiments, at least one formulation disclosed herein is suitable for supporting, controlling, restoring, maintaining or enhancing colon health, nutrient transportation, intestinal health, natural absorption of minerals, or natural nutrient utilization.

In some embodiments, at least one formulation disclosed herein is suitable for supporting, controlling, restoring, maintaining or enhancing a healthy nervous system. In some embodiments, at least one formulation disclosed herein is suitable for supporting, controlling, restoring, maintaining or enhancing neuro-protection, brain function and memory, natural nerve transmission, or GABA. In some embodiments, at least one formulation disclosed herein is suitable for supporting, controlling, restoring, maintaining or enhancing healthy stress responses, natural stress responses, or physical and mental well-being health. In some embodiments, at least one formulation disclosed herein is suitable for supporting, controlling, restoring, maintaining or enhancing respiratory health. In some embodiments, at least one formulation disclosed herein is suitable for supporting, controlling, restoring, maintaining or enhancing appetite control or weight control. In some embodiments, at least one formulation disclosed herein is suitable for supporting, controlling, restoring, maintaining or enhancing, homocysteine levels, natural production of nucleic acids and creatine phosphate, the manufacture and carbohydrate utilization, fats, and amino acids, natural protein synthesis, natural enzymatic reactions, or chemical reactions. In some embodiments, at least one formulation disclosed herein is suitable for supporting, controlling, restoring, maintaining or enhancing detoxification or neutralization of toxin. In some embodiments, at least one formulation disclosed herein is suitable for supporting, controlling, restoring, maintaining or enhancing antioxidant health or natural glutathione levels. In some embodiments, at least one formulation disclosed herein is suitable for supporting, controlling, restoring, maintaining or enhancing energy levels (stamina). In some embodiments, at least one formulation disclosed herein is suitable for supporting, controlling, restoring, maintaining or enhancing natural pH levels. In some embodiments, at least one formulation disclosed herein is suitable for supporting, controlling, restoring, maintaining or enhancing natural recovery time. In some embodiments, at least one formulation disclosed herein is suitable for supporting, controlling, restoring, maintaining or enhancing metabolism health. In some embodiments, at least one formulation disclosed herein is suitable for supporting, controlling, restoring, maintaining or enhancing natural tryptophan metabolism, natural blood sugar metabolism, or methionine metabolism. In some embodiments, at least one formulation disclosed herein is suitable for supporting, controlling, restoring, maintaining or enhancing natural thermogenesis. In some embodiments, at least one formulation disclosed herein is suitable for supporting, controlling, restoring, maintaining or enhancing natural cell division. In some embodiments, at least one formulation disclosed herein is suitable for supporting, controlling, restoring, maintaining or enhancing the immune system health. In some embodiments, at least one formulation disclosed herein is suitable for supporting, controlling, restoring, maintaining or enhancing healthy uric acid levels. In some embodiments, at least one formulation is suitable for controlling stress. In some embodiments, at least one formulation is suitable for relieving stress.

In some embodiments, one or more formulations described herein may be used as a dietary supplement and/or anticancer agent. The formulations may comprise either the above listed ingredients, its active compounds, or said ingredients and active compounds plus one or more pharmaceutically acceptable carriers. In addition to the ingredients discussed above, methods of determining active ingredients and screening for activity in the formulations described herein can be carried out according to methods known to those of skill in the art, and according to methods described in the examples herein. Formulations described herein may be mixed with pharmaceutically acceptable carriers or excipients known to those of skill in the art, and administered according to methods known to those of skill in the art including:

i.) Oral Administration in the form of juice, powders, tablets, suspension, emulsifiers, capsules, granules, troches, pills, suspensions, spirits, syrups, and limonades;

ii.) Injectable Administration intravenously or otherwise;

iii) Topical Administration in the form of ointments, solids, suspensions, powders, paps, suppositories, aerosols, cataplasms, liniments, lotions, enemas, and emulsifiers.

In addition, well-known excipients in the form of solid or liquid maybe used. The several examples of excipients used to administer the dosage forms are as follows:

Excipients in powders and other oral powders: lactose, crystalline cellulose, starch, dextrin, calcium phosphate, calcium carbonate, synthetic and natural aluminum dioxide, magnesium oxide, dried aluminum hydroxide, magnesium stearate, and sodium bicarbonate;

Excipients in topical powders: zinc oxide, talc, starch, kaolin, borate powder, zinc stearate, magnesium stearate, magnesium carbonate, precipitated calcium carbonate, bismuth subgallate, and potassium aluminum sulfate powder;

Excipients in liquids: water, glycerin, propylene glycol, sweet-taste syrup, ethanol, fatty oil, ethylene glycol, polyethylene glycol, and sorbitol;

Excipients in ointments: hydrophobic or hydrophilic base (including oil soluble base, water-soluble base and suspended base) prepared by mixing fat, fatty oil, lanoline, Vaseline, glycerin wax, Japan wax, paraffin, paraffin sulphate, resins, higher alcohols, plastics, glycols, water, or surfactant.

Formulations discussed herein can be administered in any of the forms considered herein, or otherwise known to those of skill in the art. In some embodiments, the formulation is administered orally in a liquid form, either as an extract, concentrated extract or other liquid form. In some embodiments, the formulation is administered orally twice a day, three times a day, or four times a day, with each dosing varying between 5 oz-20 oz. depending on the person's state of health, weight, severity of disease, response of disease or conditions.

A formulation described herein may be administered as a dietary supplement to facilitate normal physiological function and growth.

In certain instance, it is appropriate to administer the formulation disclosed herein in combination with an additional therapeutic agent. In some embodiments, the additional therapeutic agent comprises insulin, metformin, sulfonylureas, meglitinides, thiazolidinediones, DPP-4 inhibitors, GLP-1 receptor agonists, SGLT2 inhibitors, diuretics, beta-blockers, ACE inhibitors, angiotensin II receptor blockers, calcium channel blockers, alpha blockers, alpha-2 receptor agonist, central agonists, peripheral adrenergic inhibitors, vasodilators or a combination thereof. In some embodiments, the additional therapeutic agent comprises CETP inhibitors, FXR agonist, LXR agonist, HMG-CoA reductase inhibitors, bile acid sequestrants, niacin and related compounds, PPARalpha agonists, cholesterol absorption inhibitors, ACAT inhibitors, phenolic anti-oxidant, LDL receptor inducers, platelet aggregation inhibitors, ileal bile acid transporter or a combination thereof.

Provided in Tables A-C are a formulation described herein:

TABLE A

Representative ingredients and nutritional details of one serving of an exemplary formulation described herein. The formulation main also contain one or more additional ingredients not listed in Table A.
Supplement Facts
Serving size: 1 Pouch (14.5 g)

|  | Amount Per Serving | % Daily Value |  | Amount Per Serving | % Daily Value |  | Amount Per Serving | % Daily Value |
| --- | --- | --- | --- | --- | --- | --- | --- | --- |
| Calories | 40 | 1%* | Zinc | 12.5 mg | 84% | Ginger root | 40 | |
| Total fat | 0.5 | 1%* | Selenium | 10 mcg | 15% | Bromelain Concentrate | 0.5 | 1%* |
| Total carbohydrate | 4 g | 7%* | Copper | 210 mcg | 11% | Methylsulfonymethane | 4 g | 1%* |
| Dietary fiber | 2 g | | Manganese | 4 mg | 200% | S-Anenosylmethionine | 2 g | 7%* |
| Sugars | 0 g | | Chromium | 40 mcg | 33% | Dandelion Root Powder | 0 g | |
| Protein | 6 g | | Molybdenum | 200 mcg | 266% | Lecithin Powder | 6 g | |
| Vitamin A | 850 IU | 17% | Trimethylglycine | 550 mg | * | Beet Root Powder | 850 IU | 17% |
| Vitamin C | 250 mg | 416% | Evening Primrose oil powder | 450 mg | * | Protease | 250 mg | 416% |
| Vitamin D | 50 IU | 12% | Inulin | 460 mg | * | Superoxide Dismutase | 50 IU | 12% |
| Vitamin E | 17 IU | 56% | Medium Chain Triglycerides Oil powder | 260 mg | * | Catalase | 17 IU | 56% |
| Thiamine | 57.5 mg | 3833% | Quercetin Dihydrate | 88 mg | * | Sarsparilla Root | 57.5 mg | 3833% |
| Riboflavin | 12 mg | 705% | Rutin | 88 mg | * | DI-Methionine | 12 mg | 705% |
| Niacin | 25 mg | 125% | Hesperidin complex | 70 mg | * | L-Glutathione | 25 mg | 125% |
| Vitamin B6 | 14 mg | 700% | Milk Thistle extract | 230 mg | | *Ginseng* Root Powder | 14 mg | 700% |
| Folate | 1250 mcg | 312% | L-Taurine | 98 mg | * | L-Glycine | 1250 mcg | 312% |
| Vitamin B12 | 700 mcg | 11667% | Choline bitartrate | 100 mg | * | Alpha R-Lipoic Acid | 700 mcg | 11667% |
| Biotin | 2000 mcg | 667% | Betaine Hydrochloride | 110 mg | * | Watercress Leaf Powder | 2000 mcg | 667% |
| Pantothenic acid | 22 mg | 220% | Marshmallow | 30 mg | * | Cellulase | 22 mg | 220% |
| Calcium | 150 mg | 15% | Curcumin | 140 mg | * | Lactase | 150 mg | 15% |
| Phosphorus | 10 mg | 1% | L-Glutamine | 250 mg | * | Lipase | 10 mg | 1% |
| Magnesium | 190 mg | 48% | N-Acetyl L-Cysteine | 100 mg | * | Jerusalem Artichoke | 190 mg | 48% |

† Daily Values are based on a 2,000 calorie diet
*Daily Value (DV) not established.

TABLE B

Representative ingredients and nutritional details of one serving of an exemplary formulation described herein. The formulation main also contain one or more additional ingredients not listed in Table B.
Supplement Facts
Serving size: 1 Pouch (15.4 g)

|  | Amount Per Serving | % Daily Value |  | Amount Per Serving | % Daily Value |  | Amount Per Serving | % Daily Value |
|---|---|---|---|---|---|---|---|---|
| Calories | 35 |  | Manganese | 40 mcg | 84% | Asiatic Dogwood Fruit Extract | 33 mg | * |
| Calories from Fat | 5 |  | Chromium | 280 mcg | 15% | *Cordyceps Sinensis* Extract | 33 mg | * |
| Total fat | 0.5 | 1%* | Vanadium | 20 mcg | 11% | *Gingko Biloba* leaf extract | 33 mg | * |
| Total carbohydrate | 3 g | 1% | R-Alpha-Lipoic Acid | 84 mg | 200% | Maca | 33 mg | * |
| Dietary fiber | 2 g | 8% | Banaba | 300 mg | 33% | Suma Root | 33 mg | * |
| Sugars | 0 g |  | Berberine Hydrochloride | 500 mg | 266% | *Aswagandha* Root Extract | 200 mg | * |
| Protein | 6 g |  | Bitter Melon Extract | 301 mg | * | Holy Basil Leaf Extract | 200 mg | * |
| Vitamin C | 150 mg | 250% | Cactus Stem Extract | 125 mg | * | *Rhodiola Rosea* Extract | 112 mg | * |
| Vitamin E | 1400 IU | 350% | Choline Bitartarate | 85 mg | * | *Eleutherococcus Senticosus* Extract | 100 mg | * |
| Thiamine | 90 IU | 300% | *Cinnamon* Extract | 7 mg | * | Pantethine | 180 mg | * |
| Riboflavin | 35 mg | 2333% | Citrimax Extract | 7 mg | * | Superoxide Dismutase | 165 mg | * |
| Niacin | 10 mg | 588% | Fenugreek | 7 mg | * | Milk Thistle 80% Silymarin | 70 mg | * |
| Vitamin B6 | 45 mg | 225% | Guggul | 7 mg | * | Ginseng Root Extract | 350 mg | * |
| Folate | 3.8 | 190% | *Poria Cocos* Root Extract | 7 mg | * | *Salacia Oblonga* Extract | 250 mg | * |
| Vitamin B12 | 160 mcg | 40% | *Rehmannia Glutinosa* Rhizome | 40 mg | * | Phospholipid Complex | 330 mg | * |
| Biotin | 14 mcg | 234% | *Gymnema Sylvestre* Leaf Extract | 450 mg | * | Phosphatidyl Serine | 165 mg | * |
| Magnesium | 650 mcg | 217% | Inositol | 11 mg | * | S-Acetyl L-Glutathione | 240 mg | * |
| zinc | 50 mg | 13% | L-Carnitine L-Tartrate | 96 mg | * | N-Acetyl L-Cysteine | 305 mg | * |
| Selenium | 10 mg | 67% | PABA | 10 mg | * | L-Glutamine | 195 mg | * |

† Dairy Values are based on a 2,000 calorie diet.
*Daily Value (DV) not established.

TABLE C

Representative ingredients and nutritional details of one serving of an exemplary formulation described herein. The formulation main also contain one or more additional ingredients not listed in Table C.
Supplement Facts
Serving size: 1 Pouch (12.5 g)

|  | Amount Per Serving | % Daily Value |  | Amount Per Serving | % Daily Value |  | Amount Per Serving | % Daily Value |
|---|---|---|---|---|---|---|---|---|
| Calories | 35 |  | Folate | 160 mcg | 40% | Cactus Stem Extract | 60 mg | * |
| Calories from Fat | 5 |  | Vitamin B12 | 12 mcg | 200% | Choline Bitartarate | 85 mg | * |
| Total fat | 0.5 g | 1%* | Biotin | 650 mcg | 217% | *Cinnamon* Extract | 9 mg | * |
| Total carbohydrate | 3 g | 1%* | Calcium | 50 mg | 5% | Citrimax Extract | 12 mg | * |
| Dietary fiber | 2 g | 7%* | Magnesium | 25 mg | 6% | Fenugreek | 9 mg | * |
| Sugars | 0 g |  | Zinc | 6 mg | 40% | Guggul | 9 mg | * |
| Protein | 6 g |  | Selenium | 40 mcg | 60% | Pantethine | 75 mg | * |
| Vitamin C | 360 mg | 600% | Manganese | 5 mg | 250% | Polo Cocos Root Extract | 9 mg | * |
| Vitamin D | 1000 IU | 250% | Chromium | 280 mcg | 235% | *Rehmannia Glutinosa* Rhizome | 9 mg | * |

TABLE C-continued

Representative ingredients and nutritional details of one serving of an exemplary formulation described herein. The formulation main also contain one or more additional ingredients not listed in Table C.
Supplement Facts
Serving size: 1 Pouch (12.5 g)

|  | Amount Per Serving | % Daily Value |  | Amount Per Serving | % Daily Value |  | Amount Per Serving | % Daily Value |
|---|---|---|---|---|---|---|---|---|
| Vitamin E | 90 IU | 300% | Molybdenum | 70 mcg | 93% | *Gymnema Sylvestre* Leaf Extract | 300 mg | * |
| Vitamin K2 | 40 mcg | 50% | Vanadium | 20 mcg | * | Inositol | 12 mg | * |
| Thiamine | 29 mg | 1933% | R-Alpha-Lipoic Acid | 85 mg | * | L-Carnitine L-Tartrate | 60 mg | * |
| Riboflavin | 10 mg | 588% | Banaba | 160 mg | * | PABA | 10 mg | * |
| Niacin | 25 mg | 125% | Berberine Hydrochloride | 340 mg | * | N-Acetyl L-Cysteine | 310 mg | * |
| Vitamin B6 | 10 mg | 500% | Bitter Melon Extract | 160 mg | * | CoQ-10 | 10 mg | * |
|  |  |  |  |  |  | Taurine | 90 mg |  |

† Daily Values are based on a 2,000 calorie diet.
*Daily Value (DV) not established.

Exemplary Methods

Provided herein are methods comprising administration of at least one formulation described herein, for the treatment of diabetes in in subject. In some embodiments, are methods for the treatment of pre-diabetic symptoms in a subject. In certain embodiments are methods for the regulation of blood sugar in a subject. Certain methods described herein may comprise administration of a formulation described herein for the regulation of insulin levels in a subject.

Provided are methods for the treatment of type II diabetes in a subject comprising: administering to the subject a first formulation described herein for at least about 10 days; administering to the subject a second formulation described herein for at least about 30 days; and optionally administering to the subject a third formulation described herein. In some embodiments, a formulation described herein is administered with an additional agent. The additional agent may comprise insulin, metformin, sulfonylureas, meglitinides, thiazolidinediones, DPP-4 inhibitors, GLP-1 receptor agonists, SGLT2 inhibitors, or a combination thereof.

In some embodiments is a method of supporting glucose level in a subject's blood comprising administering to the subject one or more formulations described herein. In some embodiments is a method of supporting glucose level in a subject's blood comprising administering to the subject a formulation described herein, and optionally administering to the subject a second formulation described herein.

Provided are methods comprising administration of at least one formulation described herein, wherein at least one formulation is administered orally, intravenously, intraperitoneal, subcutaneous, topically, or a combination thereof. Optionally, at least one formulation is administered as a pill, or as two or more pills. In some embodiments, the two or more pills are administered simultaneously, sequentially, or intermittently. In some embodiments, at least one formulation is administered as a powder formulation. In some embodiments, at least one formulation is administered as a combination of one or more pills and a powder formulation. The combination maybe administered simultaneously, sequentially, or intermittently.

In some methods provided herein, at least one formulation is administered as a liquid formulation. In some cases, the liquid formulation may be obtained by reconstituting a powder formulation in a liquid. In some cases, at least one formulation is administered as a combination of one or more pills and a liquid formulation. In certain embodiments, the combination is administered simultaneously, sequentially, or intermittently.

In some methods provided herein, at least one formulation is administered as an emulsion formulation. In certain embodiments, at least one formulation is administered as a combination of one or more pills and an emulsion formulation. The combination maybe administered simultaneously, sequentially, or intermittently.

In some methods provided herein, at least one formulation is mixed in food. In some cases, the food is a beverage, a shake, or a snack. In some instances, the beverage is tea, coffee, or energy drink. In an embodiment, the food is consumed by the subject as part of a meal or diet plan.

Provided herein are methods of controlling blood sugar in a subject with insufficient insulin comprising administering to the subject a formulation described herein. In some embodiments, is a method of controlling blood sugar in a subject with insufficient insulin comprising administering to the subject a formulation described herein, and optionally administering to the subject at least one second formulation described herein.

Provided is a method of supporting liver function comprising administering to a subject in need thereof a formulation described herein. In some embodiments is a method of supporting liver function comprising administering to the subject a formulation described herein, and optionally administering to the subject at least one second formulation described herein.

Provided is a method of maintaining normal cholesterol level comprising administering to a subject in need thereof a formulation described herein. In certain embodiments, is a method of maintaining normal cholesterol level comprising administering to the subject a formulation described herein, and optionally administering to the subject at least one second formulation described herein. In some embodiments are methods of supporting normal cholesterol level comprising administering to a subject in need thereof a formulation described herein. In some embodiments are methods of maintaining healthy arterial wall comprising administering to a subject in need thereof a formulation described herein.

Provided is a method of supporting red blood cell formation comprising administering to a subject in need thereof a formulation described herein.

In some embodiments is a method of for supporting, controlling, restoring, or maintaining blood sugar levels in an individual comprising administering to the individual an amount of at least one formulation comprising: group A components consisting essentially of at least one protein optionally selected from a list comprising pea protein isolate and sacha inchi protein; at least one group B component that comprises dandelion extract, milk thistle extract, phospholipids, ginger, taurine, turmeric extract, vitamin C, or methionine; at least one group C component that comprises magnesium, trimethylglycine, glutathione, N-acetyl-cysteine, *Cordyceps sinensis* extract, glutamine, alpha lipoic acid, or glycine; and an excipient.

Provided is a method of for supporting, controlling, restoring, or maintaining blood sugar metabolism in an individual comprising administering to the individual an amount of at least one formulation comprising: group A components consisting essentially of maca, *Cornus officinalis* fruit extract, and optionally broad bean; at least one group B component that comprises berberine, bitter melon extract, *Gymnema sylvestre* leaf extract, banaba, or carnitine; at least one group C component that comprises vitamin C, *Panax ginseng* root extract, Aswagandha root extract, holy basil leaf extract, *Rhodiola rosea* extract, *Eleutherococcus senticosus* extract, vitamin B5, cactus stem extract, phosphatidylserine, or vitamin D; and an excipient.

Provided is a method of for supporting, controlling, restoring, or maintaining blood sugar metabolism in an individual comprising administering to the individual an amount of at least one formulation comprising: group A components consisting essentially of cactus stem extract and optionally broad bean; at least one group B component that comprises berberine, bitter melon extract, *Gymnema sylvestre* leaf extract, banaba, or carnitine; at least one group C component that comprises *Garcinia cambogia* extract, *Rehmannia glutinosa* extract, *Poria cocos* root extract, cinnamon extract, Fenugreek, Guggul, or Vitamin D; and an excipient.

In some embodiments, is a method described herein, wherein the individual suffers from insulin insufficiency. In certain embodiments, the individual is diabetic. In some embodiments, the individual is pre-diabetic. In certain embodiments, a formulation described herein is administered to the individual for a period of about 10, 15, 20, 30, 40, 45, 50, or 60 days. In some embodiments, a formulation described herein may be administered to the individual said formulation for a period of about one month to about sixty months.

In some embodiments, a method described herein further comprises use of a diet plan. In certain embodiments, the diet plan further comprises recipes. In some embodiments, the diet plan further comprises recipes for at least one of breakfast, lunch, snacks, and dinner.

Exemplary Kits

Provided are kits for use in the methods described herein. In some embodiments are provided kits comprising at least one formulation described herein; and instructions for use thereof. In certain embodiments is a kit described herein, further comprising at least one diet plan or meal plan. In some embodiments, the kit further comprises at least one recipe.

In some embodiments is a kit useful for supporting, controlling, restoring, or maintaining blood sugar levels in an individual comprising: at least one formulation described herein; instructions for use of the at least one formulation; and optionally at least one diet plan.

A diet plan described herein may further comprise recipes. In some embodiments, the diet plan further comprises recipes for at least one of breakfast, lunch, snacks, and dinner. In some embodiments, at least one diet plan is tailored to complement said at least one formulation. In some embodiments, the diet plan is tailored based on the level of at least one indicator in the individual. In certain cases, the at least one indicator is body mass index (BMI), liver fat level or hemoglobin A1C count.

In some embodiments, a kit described herein is useful for the treatment of diabetes. In some cases, the kit is useful for the management of blood sugar. In certain cases, the kit further comprises at least one additional therapeutic agent. In a few cases, the additional agent comprises insulin, metformin, sulfonylureas, meglitinides, thiazolidinediones, DPP-4 inhibitors, GLP-1 receptor agonists, SGLT2 inhibitors, or a combination thereof.

Exemplary Diet Plans

In some embodiments provided herein are diet plans (also referred to as diet regimen or simply regimen) for implementation in conjugation with the methods and formulations described herein. A diet plan described herein maybe included in a method and/or kit described herein. In certain embodiments, a diet plan described herein is tailored for the individual based on an understanding of the symptoms exhibited by the individual. In some embodiments, a diet plan described herein works in synergy with a method and/or formulation described herein to achieve a desired result. In some embodiments, the desired result in a reduction or stabilization of blood glucose levels. In certain embodiments, the desired result is a reduction or elimination of insulin administration. In certain embodiments, the desired result is a reduction in BMI. In certain embodiments, the desired result is a reduction or elimination of one or more symptoms of type II diabetes or an associated condition described herein.

In some embodiments, the diet plans described herein, are designed to support some of the integral systems of human physiology, which include, but are not limited to, blood sugar metabolism, insulin receptor site sensitivity, anti-inflammatory support, liver function, gastro-intestinal system, immune system, brain function, adrenal gland functions, anti-oxidant support. In some embodiments, the plans and regimens described herein, are designed to ameliorate diabetes directly. In some embodiments, the regimens described herein, are designed to ameliorate the most common underlying issues associated with your diabetes.

In some embodiments, the diet plans described herein comprises administration of the compositions and formulations described herein to an individual. In some embodiments, the compositions and formulations described herein are administered in the form of pills, tablets, liquid formulations, shakes etc. In some embodiments, the shakes are flavored. In some embodiments, the compositions described herein are in the form of powders and packaged in packets or pouches. In some embodiments, the formulation in the regimen is a powder that can be mixed with cold water or unsweetened almond milk. In some embodiments the contents of the packets or pouches are mixed with a potable liquid, until the powder is completely in solution, to prepare a shake. In some embodiments the formulation in the regimen is stirred.

In some embodiments, each packet represents one dose. In some embodiments the formulation is placed in a container with a lid that can be shaken. In some embodiments the contents of the packets or pouches are mixed with up-to 8 ounces of water, to prepare a shake. In some embodiments the contents of the packets or pouches are mixed with less than 8 ounces of water, to prepare a shake. In some embodiments the contents of the packets or pouches are mixed with up-to 8 ounces of unsweetened almond milk, to prepare a shake. In some embodiments the contents of the packets or pouches are mixed with less than 8 ounces of unsweetened almond milk, to prepare a shake. In some embodiments, the amount of water or milk may be adjusted according to desired consistency of the prepared shake. In some embodiments, the contents of the packets or pouches are not mixed with almond milk, for administration to individuals who are allergic to nuts.

In some embodiments, the compositions or formulations described herein are administered, to individuals, as shakes three times a day. In some embodiments, the formulation in the regimen is taken for 30 days. In some embodiments, the diet regimen is followed until desired quality of life outcomes are achieved. Exemplary desired quality of life outcomes can include, but are not limited to, weight loss, improved sleep patterns, reduced limb pains, reduced joint pains, normalized blood pressure etc. In some embodiments, the diet regimen is followed until normalized blood sugar levels are achieved.

In some embodiments, the compositions described herein are taken with breakfast. In some embodiments, the compositions described herein are taken with lunch. In some embodiments, the compositions described herein are taken with dinner. In some embodiments, the compositions described herein are taken with breakfast and dinner. In some embodiments, the compositions described herein are taken with breakfast, lunch and dinner.

In some embodiments, the regimen is accompanied by plenty of water. In some embodiments, the regimen is accompanied by herbal teas. In some embodiments, the regimen is accompanied by decaf green tea. In some embodiments, the regimen is accompanied by fresh fruits (including blueberries, strawberries, blackberries, lemon, banana, apple). In some embodiments, the regimen is accompanied by vegetables (including celery, carrots, zucchini, cucumbers, avocado, beets, eggplant, asparagus, onion, garlic, spinach, lettuce, butternut squash, cauliflower, broccoli, peppers, yams and sweet potatoes), beans (pinto, black, navy, white, red kidney), and peas (including fresh, split, snap). In some embodiments, the regimen is accompanied by fish. In some embodiments, the regimen is accompanied by moderate amounts of chicken. In some embodiments, the regimen is accompanied by moderate amounts of turkey. In some embodiments, the regimen is accompanied by moderate amounts of lamb. In some embodiments, the regimen is accompanied by olive oil. In some embodiments, the regimen is accompanied by coconut oil. In some embodiments, the regimen is accompanied by flaxseed oil (in moderation). In some embodiments, the regimen is accompanied by seeds and nuts. In some embodiments, peanuts are excluded. In some embodiments, the regimen is accompanied by almond butter. In some embodiments, the regimen is accompanied by cashew butter. In some embodiments, the regimen is accompanied by unsweetened almond or coconut milk. In some embodiments, the regimen is accompanied by turkey bacon (nitrate/nitrite and gluten free). In some embodiments, the regimen is accompanied by turkey sausage patties (nitrate/nitrite and gluten free). In some embodiments, the regimen is accompanied by skinny crisps—Plain Jane or Onion. In some embodiments, the regimen is accompanied by *Stevia*, xylitol, Grade B Maple Syrup, or coconut sugar. In some embodiments, the formulation in the regimen is accompanied by a snack. In some embodiments the snack comprises fresh berries, fruits, nuts, almond, cashew butter on apples, celery, jicama, bananas, avocado, skinny crisps-plain Jane or onion, or a combination thereof.

In some embodiments, dairy (milk, cheeses, yogurt, butter) should be avoided. In some embodiments, eggs, margarine and shortening should be avoided, while being on the regimen. In some embodiments, foods prepared with gluten should be avoided, while being on the regimen. In some embodiments, all grains (including corn, rice, *quinoa*) should be avoided, while being on the regimen. In some embodiments, tomatoes, tomato sauces, corn, and white potatoes should be avoided. In some embodiments, peanuts or peanut butter should be avoided, while being on the regimen. In some embodiments, soy or products made from soy (including soymilk, meat substitutes and tofu) should be avoided, while being on the regimen. In some embodiments, beef should be avoided. In some embodiments, pork should be avoided, while being on the regimen. In some embodiments, cold cuts should be avoided, while being on the regimen. In some embodiments, bacon should be avoided, while being on the regimen. In some embodiments, hotdogs should be avoided. In some embodiments, canned meat should be avoided, while being on the regimen. In some embodiments, sausage should be avoided, while being on the regimen. In some embodiments, shellfish should be avoided, while being on the regimen. In some embodiments, honey, sugar or artificial sweeteners should be avoided, while being on the regimen. In some embodiments, alcohol should be avoided, while being on the regimen. In some embodiments, caffeine (including coffee, decaf coffee, black tea, soda/diet soda) should be avoided, while being on the regimen. In some embodiments, fruit juices should be avoided, while being on the regimen.

In some embodiments, junk foods (e.g.—soda pops, cookies, cakes, candies, ice creams etc.) should be avoided, while being on the regimen. In some embodiments, refined foods should be avoided, while being on the regimen. In some embodiments, foods that contain dairy, corn, wheat, gluten, soy should be avoided, while being on the regimen. In some embodiments, consumption of alcohol should be significantly reduced, while being on the regimen. In some embodiments, consumption of caffeine should be significantly reduced, while being on the regimen. In some embodiments, damaged and harmful fats (e.g.—hydrogenated oils, trans fats etc.) should be avoided, while being on the regimen. In some embodiments, artificial sweeteners should be avoided, while being on the regimen.

In certain embodiments, the introduction of additional food items are allowed, while an individual is administered compositions described herein. Additional food items can include, but are not limited to, grains (including corn, rice), *quinoa*, tomatoes, tomato sauces, corn, white potatoes, peanut butter, soy products, pork, cold cuts, bacon, hot dog, canned meat, sausage, honey, sugar, artificial sweeteners, caffeine (including coffee, decaf coffee, black tea, soda/diet soda), fruit juices, and caffeine. In some embodiments, only one additional food item is introduced to the regimen and no other additional items are introduced for about three days to about five days. In some embodiments, one or more additional items are introduced to the regimen, after about three days to about five days of introducing the only one additional item.

In some embodiments, the diet plan is associated with a myriad of improved physiological outcomes, which include, but are not limited to, increase in urine output, increase in the number of daily bowel movements, decrease in blood sugar, blood pressure, and cholesterol levels, increased energy, weight loss, decrease in need for prescription medication, decrease in insulin requirements, better sleep habits, rested feeling upon rising, overall better sense of well-being, subsiding and or complete elimination of various other negative symptoms.

In some embodiments, the diet plan or regimen comprising administration of the compositions described herein may be associated with decreased blood sugar, blood pressure and cholesterol levels. In some embodiments, the reduction of blood sugar levels are indicated by, low glucometer reading, irritability, light-headedness, sweating, brain fog or confusion, shakiness, fatigue, lethargy, nervousness, anxiety, confusion, rapid heartbeat or pulse, nausea, hunger, tingling or numbness in the lips or tongue, lack of coordination, nightmares or crying out during sleep, seizures, or unconsciousness. In some embodiments, the individual following the regimens described herein, by consumption of the compositions described herein, experiencing low blood sugar levels, is recommended to consult a medical practitioner, to manage and normalize the blood sugar levels. In some embodiments, the blood sugar levels are managed and normalized by food intake in frequent intervals. In some embodiments, the frequent interval is between about 2 hr to about 3 hr. In some embodiments, the blood sugar levels are managed and normalized by altering the dose of blood sugar medicine. In some embodiments, the blood sugar medicine is Insulin. In some embodiments, the blood sugar levels are managed and normalized by eating a health snack or a meal. In some embodiments, the blood sugar medicine is Insulin. In some embodiments, the blood sugar levels are managed and normalized by eating food items that raise blood sugar levels rapidly.

In some embodiments, the reduction of blood pressure levels are indicated by symptoms comprising headaches, fatigue, lethargy, lowered body temperature, chill or cold feeling, or dizziness. In some embodiments, the individual following the regimens described herein, by consumption of the compositions described herein, is recommended to monitor his or her blood pressure levels at regular intervals. In some embodiments, the individual following the regimens described herein, by consumption of the compositions described herein, experiencing low blood pressure levels, is recommended to consult a medical practitioner, to manage and normalize the blood pressure levels. In some embodiments, the reduction of cholesterol levels are indicated by symptoms comprising, cognitive changes, depression, mood changes, behavioral changes, suicidal tendencies, or sexual dysfunction. In some embodiments, the individual following the regimens described herein, by consumption of the compositions described herein, experiencing lower than optimal cholesterol levels, is recommended to consult a medical practitioner, to manage and normalize the cholesterol levels.

In some embodiments, the regimen or diet plan is a metabolic cleansing program, also known as a detoxification program. In some embodiments, symptoms that are consistent with detoxification may be observed. In some embodiments, the symptoms consistent with detoxification comprise headaches, skin breakouts, gas, increased bowel movements, body aches, bloating, irritability, brain fog, fatigue/low energy, food cravings, constipation, diarrhea, or a combination thereof. In some embodiments, these symptoms subside in a few days. In some embodiments, the symptoms listed above may be previously existing, prior to starting the regimen.

In some embodiments, the gas or bloating, constipation, and/or diarrhea may be managed by adhering to one or more of the following recommendations:

Ensuring enough intake of water to stay well hydrated.

Ensuring that the dietary recommendations are being followed as close to 100% as possible.

Reading ingredient labels to make sure you are not consuming anything that is restricted with the regimen.

Consuming high quality source of fiber in nutritional supplement form. Fiber can add bulk to the stool and can be effective in relieving diarrhea.

Reducing the dosage of the compositions described herein by about 50% to about 75%.

If a reduction of 75% of the original dose does not cause the symptoms to significantly reduce to a tolerable level or reduce them completely stopping consumptions of the compositions described herein for a few days, while continuing the other dietary recommendations.

Eliminating any new dietary items that the individual was not eating prior to starting the regimen, and only introduced to his or her diet as part of the regimen.

If after eliminating those foods the gas and bloating are reduces to a tolerable level or are eliminated completely the individual following the regimen is recommended to add the eliminated foods back one at a time to identify the offending food.

If the gas and bloating were present prior to starting the regimen it is likely to subside in a few days to about a week as the system rebalances.

If any negative symptom persists for longer than 7 days or progresses and the above steps have been taken with no improvement it is recommended to discontinue the program all together and consult a health care provider.

Exemplary Indications

Provided herein are methods, formulations and kits comprising dietary supplements for administration to a subject that may be suffering from one or more indications described herein. Exemplary indications that can be treated, supported, prevented or cured by a method, composition, formulation, or kit comprising dietary supplements described herein are stated or enumerated throughout this description. Certain exemplary indications are discussed in further depth below.

For instance, disclosed herein are methods, formulations and kits for administration to an individual diagnosed with diabetes and/or complications associated with diabetes.

Diabetes: Diabetes mellitus is a metabolic disorder characterized by hyperglycemia and disturbances of carbohydrate, protein and fat metabolisms or relative lack of the hormone insulin. Diabetes mellitus, often simply referred to as diabetes, is a group of metabolic diseases in which a person has high blood sugar, either because the body does not produce enough insulin or because cells do not respond to the insulin that produce enough insulin or because cells do not respond to the insulin that is produced. This high blood sugar produces the classical symptoms of polyuria (frequent urination), polydipsia (increased thirst) and polyphagia (increased hunger).

Types of Diabetes: Type I diabetes is characterized by loss of the insulin-producing beta cells of the islets of Langerhans in the pancreas leading to insulin deficiency. This type of diabetes is further classified as immune-mediated or idiopathic. The majority of type I diabetes is of the immune-mediated nature, where beta cell loss is a T-cell mediated autoimmune attack. There is no known preventive measure against type I diabetes, which causes approximately 10% of diabetes mellitus cases in North America and Europe. Most affected people are otherwise healthy and of a healthy weight when onset occurs. Sensitivity and responsiveness to insulin are usually normal, especially in the early stages. Type I diabetes affects children or adults but was traditionally termed "juvenile diabetes" because it represents a majority of the diabetes cases in children. Type II diabetes is characterized by insulin resistance which may be combined with relatively reduced insulin secretion. The defective responsiveness of body tissues to insulin is believed to involve the insulin receptor. However, the specific defects are not known. Diabetes mellitus due to a known defect are classified separately. Type II diabetes is the most common type. In the early stage of type II diabetes, the predominant abnormality is reduced insulin sensitivity. At this stage hyperglycemia can be reversed by a variety of measures and medications that improve insulin sensitivity or reduce glucose production by the liver. Type II diabetes, is believed to develop when: the receptors on cells in the body that normally respond to the action of insulin fail to be stimulated by it (insulin resistance). In response to this more insulin may be produced, and this over-production exhausts the insulin-manufacturing cells in the pancreas; insufficient insulin available; and the insulin that is available may be abnormal and therefore doesn't work properly. In certain embodiments, methods, formulations and kits described herein are useful for support and/or treatment of an individual suffering from diabetes. In certain embodiments the diabetes is type I diabetes. In some cases, the individual is diagnosed to type II diabetes. In certain embodiments, the individual is identified as pre-disposed to diabetes. In certain instances, the predisposition is societal or genetic.

Complications associated with diabetes: In certain embodiments, methods, formulations and kits described herein are useful for support and/or treatment of an individual demonstrating or diagnosed with complications associated with diabetes.

Skin complications: diabetes affects every part of the body, including the skin. In fact, such problems are sometimes the first sign that a person has diabetes. These include bacterial infections, fungal infections, and itching. Other skin problems happen mostly or only to people with diabetes. These include but are not limited to acanthosis nigricans, diabetic dermopathy, necrobiosis lipoidica diabeticorum, diabetic blisters, eruptive xanthomatosis, digital sclerosis, and disseminated granuloma annulare. Diabetes can cause changes in the skin of the feet. At times the feet may become very dry. The skin may peel and crack. In certain cases, the nerves that control the oil and moisture in the feet are no longer functioning. In certain embodiments, methods, formulations and kits described herein are useful for support and/or treatment of an individual suffering from skin complications associated with diabetes.

Eye complications: these include glaucoma (people with diabetes are 40% more likely to suffer from glaucoma than people without diabetes), cataracts (people with diabetes are 60% more likely to develop cataract), retinopathy (including nonproliferative retinopathy, macular edema, and proliferative retinopathy). In certain embodiments, methods, formulations and kits described herein are useful for support and/or treatment of an individual suffering from eye complications associated with diabetes.

Neuropathy (nerve damage): nerve damage from diabetes is called diabetic neuropathy. About half of all people with diabetes have some form of nerve damage. It is more common in those who have had the disease for a number of years and can lead to many kinds of problems. If the blood glucose levels are kept on target, it may help prevent or delay nerve damage. Although it can hurt, diabetic nerve damage can also lessen the ability to feel pain, heat, and cold. Loss of feeling often means the patient may not feel a foot injury. Nerve damage can also lead to changes in the shape of the feet and toes. In certain embodiments, methods, formulations and kits described herein are useful for support and/or treatment of an individual suffering from neuropathy.

Foot complications: such as calluses, foot ulcers, poor circulation or amputation. Calluses occur more often and build up faster on the feet of people with diabetes. Foot ulcers occur most often on the ball of the foot or on the bottom of the big toe. Ulcers on the sides of the foot are usually due to poorly fitting shoes. People with diabetes are far more likely to have a foot or leg amputated than other people. Many people with diabetes have peripheral arterial disease (PAD), which reduces blood flow to the feet. Also, many people with diabetes have nerve disease, which reduces sensation. Together, these problems make it easy to get ulcers and infections that may lead to amputation. In certain embodiments, methods, formulations and kits described herein are useful for support and/or treatment of an individual suffering from or at risk of foot complications that may be associated with diabetes.

Diabetic ketoacidosis (DKA): Diabetic ketoacidosis (DKA) is a serious condition that can lead to diabetic coma (passing out for a long time) or even death. When the cells don't get the glucose they need for energy, the body begins to burn fat for energy, which produces ketones. Ketones are acids that build up in the blood and appear in the urine when the body doesn't have enough insulin. They are a warning sign that the diabetes is out of control. High levels of ketones can poison the body. In certain embodiments, methods, formulations and kits described herein are useful for support and/or treatment of an individual suffering from or at risk of diabetic ketoacidosis.

Kidney disease (Nephropathy): Inside kidneys are millions of tiny blood vessels that act as filters. Their job is to remove waste products from the blood. Sometimes this filtering system breaks down. Diabetes can damage the kidneys and cause them to fail. Failing lose their ability to filter out waste products, resulting in kidney disease. Diabetes can damage this system. High levels of blood sugar make the kidneys filter too much blood. All this extra work is hard on the filters. After many years, they start to leak and useful protein is lost in the urine. Having small amounts of protein in the urine is called microalbuminuria. In certain embodiments, methods, formulations and kits described herein are useful for support and/or treatment of an individual suffering from or at risk of kidney disease.

High blood pressure (Hypertension): nearly 1 in 3 American adults has high blood pressure and 2 in 3 people with diabetes report having high blood pressure or take prescription medications to lower their blood pressure. The heart has to work harder when blood pressure is high, and the risk for heart disease, and other problems goes up. In certain embodiments, methods, formulations and kits described herein are useful for support and/or treatment of an individual suffering from or at risk of high blood pressure.

Hyperosmolar Hyperglycemic Nonketotic Syndrome (HHNS): this is a serious condition most frequently seen in older persons. HHNS can happen to people with either type 1 or type 2 that is not being controlled properly, but it occurs more often in people with type 2. HHNS is usually brought on by something else, such as an illness or infection. In HHNS, blood sugar levels rise, and the body tries to get rid of the excess sugar by passing it into the urine. Lots of urine is made at first, and the patient has to go to the bathroom more often. Later the patient may not have to go to the bathroom as often, and the urine becomes very dark. Also, the patient may be very thirsty. If HHNS continues, the severe dehydration will lead to seizures, coma and eventually death. HHNS may take days or even weeks to develop. In certain embodiments, methods, formulations and kits described herein are useful for support and/or treatment of an individual suffering from or at risk of HHNS.

Gastroparesis: Disorder affecting people with both type 1 and type 2 diabetes in which the stomach takes too long to empty its contents (delayed gastric emptying). The vagus nerve controls the movement of food through the digestive tract. If the vagus nerve is damaged or stops working, the muscles of the stomach and intestines do not work normally, and the movement of food is slowed or stopped. Just as with other types of neuropathy, diabetes can damage the vagus nerve if blood glucose levels remain high over a long period of time. High blood glucose causes chemical changes in nerves and damages the blood vessels that carry oxygen and nutrients to the nerves. In certain embodiments, methods, formulations and kits described herein are useful for support and/or treatment of an individual suffering from or at risk of gastroparesis.

Heart diseases: People with diabetes have a higher-than-average risk of having a heart attack or stroke. These strike people with diabetes more than twice as often as people without diabetes. There's a big link between diabetes, heart disease, and stroke. In fact, two out of three people with diabetes die from heart disease or stroke, also called cardiovascular disease. Clogged blood vessels can lead to heart attack, stroke, and other problems. But there are treatments for heart disease, stroke, and blood vessel disease. In certain embodiments, methods, formulations and kits described herein are useful for support and/or treatment of an individual suffering from or at risk of heart diseases.

Inflammation: People with type 2 diabetes don't produce enough insulin or their bodies can't use the insulin adequately. Insulin may also have an impact on tissue in the body. Its effects on tissue are influenced by many factors, including obesity and the accumulation of fat around the belly and on major organs in the abdomen. The fat cells can produce chemicals that lead to inflammation. Scientists are only beginning to understand the role this form of internal inflammation may play in the development of chronic diseases like diabetes. In certain embodiments, methods, formulations and kits described herein are useful for support and/or treatment of an individual suffering from or at risk of inflammation.

Mental health: People with diabetes often deal with natural emotions like stress, sadness, anger and denial before they lead to depression. In certain embodiments, methods, formulations and kits described herein are useful for support and/or treatment of an individual suffering from or at risk of mental health issues.

Disclosed herein are methods, formulations and kits for treating skin complications resulting from diabetes. Disclosed herein are methods, formulations and kits for treating eye complications resulting from diabetes. Disclosed herein are methods, formulations and kits for treating neuropathy resulting from diabetes. Disclosed herein are methods, formulations and kits for treating foot complications resulting from diabetes. Disclosed herein are methods, formulations and kits for treating diabetic ketoacidosis. Disclosed herein are methods, formulations and kits for treating kidney disease resulting from diabetes. Disclosed herein are methods, formulations and kits for treating high blood pressure resulting from diabetes. Disclosed herein are methods, formulations and kits for treating hyperosmolar hyperglycemic nonketotic syndrome resulting from diabetes. Disclosed herein are methods, formulations and kits for treating gastroparesis resulting from diabetes. Disclosed herein are methods, formulations and kits for treating heart disease resulting from diabetes. Disclosed herein are methods, formulations and kits for treating mental diseases resulting from diabetes. Disclosed herein are methods, formulations and kits for treating inflammation resulting from diabetes.

High cholesterol: Abnormal cholesterol levels (hypercholesterolemia)—higher concentrations of LDL particles and lower concentrations of functional HDL particles—are strongly associated with cardiovascular disease because these promote atheroma development in arteries (atherosclerosis). This disease process leads to myocardial infarction (heart attack), stroke, and peripheral vascular disease. Since higher blood LDL, especially higher LDL particle concentrations and smaller LDL particle size, contribute to this process more than the cholesterol content of the HDL particles, LDL particles are often termed "bad cholesterol" because they have been linked to atheroma formation. On the other hand, high concentrations of functional HDL, which can remove cholesterol from cells and atheroma, offer protection and are sometimes referred to as "good cholesterol". These balances are mostly genetically determined, but can be changed by body build, medications, food choices, and other factors. Disclosed herein are methods, formulations and kits for treating high cholesterol and complications resulting from high cholesterol.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

Example 1

Formulations and diet plans described herein were administered to 311 individuals, to assess the effect of a diet comprising the formulations described herein, on biological markers and other parameters indicative of blood glucose control. Blood levels were measured, before and after the administration of formulations and diet plans described herein, for the following biological markers: glycated hemoglobin (HbA1C), total cholesterol, triglycerides, homocysteine, C-reactive protein (CRP), vitamin D. Other parameters that were monitored before and after the administration of formulations and diet plans described herein included overall weight Change, requirement for oral diabetes medications and/or insulin injections.

Out of the 311 participants, 152 (about 48%) were fully compliant with proper administration of formulations and diet plans described herein, for the entire duration of the study. The average change in the biological markers assessed are listed in Table 1

TABLE 1

Biological Markers before and after administration

| Biological Marker | Average Change in Blood Levels |
|---|---|
| HbA1C | 17% reduction |
| Total Cholesterol | 3.2% reduction |
| Triglycerides | 30% reduction |
| Homocysteine | 10% reduction |
| C-reactive protein | 5% increase |
| Vitamin D | 70% increase |

The total number of participants, who experienced reduction in oral and parenteral (insulin) diabetic medication requirements, are listed below in Table 2.

TABLE 2

Diabetic medication requirements before and after administration of formulations and diet plans described herein

| Parameter | Number of Participants/% of Compliant Participants |
|---|---|
| Off Oral Medications | 85/(55%) |
| Off Insulin Injections | 32/(21%) |
| Participant became Non-Diabetic at the end of the Study | 85/(55%) |

The study participants also experienced varying degrees of weight loss, and the results, grouped according to starting weights are shown below, in Table 3

TABLE 3

Weight loss after Life Support Diet

| Starting Weight Range | Final Weight Range | Average Weight Loss |
|---|---|---|
| 300-350 lbs. | 280-320 lbs. | 40 lbs. |
| 250-300 lbs. | 190-260 lbs. | 31 lbs. |
| 200-250 lbs. | 150-240 lbs. | 24 lbs. |
| 135-200 lbs. | 120-190 lbs. | 16 lbs. |

Collectively, the clinical study indicated that administration of a formulation described herein optionally combined with a diet plan described herein resulted in significant improvement in management of a wide range of conditions associated with type II diabetes.

Example 2: Case Studies on Type II Diabetes Patients

The following examples describe case studies of six participants, who experienced remarkable improvements in diabetes and other associated conditions, after being on the regimen, by administration of the compositions described herein.

Study Goals: The primary goal of the study was to assess the effects of administering a composition described herein, using methods described herein, on the overall glucose homeostatis in the participant. Secondary goals included monitoring blood levels of other markers associated with improper glucose homeostasis.

Study Design and Assessment: The participants were administered with at least one formulation or composition described herein, and blood marker levels were assessed before beginning administration and after being in a method or regimen comprising administration of at least one formulation for various lengths of time.

Participant No. 1:

Clinical Background of Participant: The participant had a family history of diabetes, elevated blood glucose levels and was under various medications to manage cardiovascular, endocrinal, digestive, and ocular issues.

The participant was diagnosed to have impairment in the following mechanisms, as a result of hyperglycemia: dysglycemia, inflammation, viral infection pattern, adrenal fatigue, hippocampus dysfunction, dysregulation of hypothalamic-pituitary-adrenal axis, vitamin D deficiency, and intestinal dysbiosis.

Formulations described herein were administered to the individual. The following ingredients were to address dysglycemia were present in one or more formulations administered to the individual:

*Gymnema Sylvestre*: The natural substance has demonstrated positive impacts in managing and supporting insulin resistance patterns. Specifically, it has been associated with a reduction in insulin requirements, decrease fasting blood sugar, enhance the action of insulin, aid in the regeneration of pancreatic beta cells, thereby correcting insulin resistance.

Chromium: Chromium levels are known to play a role in insulin resistance. In view of that knowledge, chromium was included in the compositions described herein, to improve insulin resistance. The mineral was found to increases the health and sensitivity of the receptor sites, resulting in better transport of glucose molecules across the cell membrane, and utilization of glucose for energy production, in the form of ATP.

Vanadium: This was also a critical mineral included in the compositions described herein, for managing insulin resistance.

Alpha Lipoic acid: This ingredient was also included in the compositions described herein, as it is known to improve insulin resistance by increasing activation of glucose transporter 1 and 4 which enhance glucose disposal by sensitizing tissues to insulin and by restoring proper intracellular redox states which then reset signalling and response to insulin.

Banaba Leaf Extract: The natural substance, containing triterpenoid, lager stroemin, flosin B, reginin A, and corosolic acid, which have been shown to help regulate glucose levels, was included in the compositions described herein, to produce glucose lowering effects by enhancing peripheral glucose utilization.

Bitter Melon: The popular plant used worldwide to support patients with diabetes.

Vitamin D: Blood levels of the prohormone Vit. D have been shown to be very important in blood sugar metabolism, insulin receptor site activity, immune function, cardiovascular health, bone health, reduced risk of some forms of cancer, musculoskeletal pain, preventative role in Type 1 diabetes, and some neurodegenerative disease etc.

In addition, to manage intestinal dysbiosis, probiotic therapy was carried out. The supplementation of probiotics has been shown to facilitate and normalize healthy gut flora. Unhealthy gut flora (intestine dysbiosis) has been associated with intestinal permeability, malabsorption, irritable bowel disease, inflammatory bowel disease, reduced immune function, digestive distress etc.

Table 4, shows the blood levels of selected markers, measured before and after six weeks of administering the compositions described herein, to participant no. 1, using the methods described herein.

| Blood Marker | Prior to administration of Claimed Compositions | After six weeks of administration of Claimed Compositions |
|---|---|---|
| HbA1c (glycated hemoglobin) | 7.2 | 6.4 |
| Total Cholesterol | 126 mg/dL | 108 mg/dL |
| Vitamin D | 34.1 ng/mL | 64.7 ng/mL |
| Absolute Lymphocyte Count | 3.5 | 2.6 |

Apart from the blood work results listed above, the participant also experienced the following quality of life improvements:

A weight loss of 15 lbs. without any exercise, which indicated that the glucose metabolism was returning to homeostasis.

A reduction in the amount of prescription medication was observed within a month of being on the Life Support regimen, carried out by administration of the composition described herein.

Increased energy levels were observed within a month of being on the Life Support regimen, carried out by administration of the composition described herein.

An improvement in eyesight, verified by an ophthalmologist, was observed within a month and a half of administration of the composition described herein.

Complete elimination of peripheral neuropathy and numbness in both feet, was observed within four months of being on the Life Support regimen, carried out by administration of the composition described herein.

The reduction in weight achieved only by administration of the compositions described herein, without any exercise was beneficial and especially helpful for people who have medical restrictions and are not advised exercise. The glycated hemoglobin levels were indicative of a reversal from diabetic to pre-diabetic state. The reduction in lymphocyte count indicated that the immune system responded to the administration of compositions described herein, and the viral infection pattern was also ameliorated.

Participant No. 2:

Clinical Background of Participant: The participant suffered from Type II diabetes and was under insulin medication, at a dosage of 20-30 units, four times a day.

The participant was diagnosed to have irregularities in the following mechanisms, as a result of hyperglycemia: dysglycemia, inflammation, liver dysfunction, fatty liver, intestinal dysbiosis.

The participant was administered formulations described herein. The following ingredients were present in one or more formulations administered to the participant:

Magnesium: It improved insulin resistance by optimizing insulin secretion, activating glucose transport for insulin mediated glucose uptake.

Biotin: It improved insulin response to glucose load, lowered post-prandial glucose levels, and upregulated the enzyme glucokinase, which is responsible for the first step in glucose utilization by the liver.

Glutathione and Superoxide dismutase: One of the most powerful antioxidants known to the human species, thus very important in the management of inflammation. The status of glutathione is considered the single most accurate indicator of the health of a cell. Blood sugar disorders deplete both nutrients. Also important for heart health, liver detox, immune modulation, fatty liver and other conditions.

Carnitine, choline, inositol, taurine, L-methionine, and N-acetyl cysteine promote the synthesis of phospholipids which are the building blocks of the lipoprotein used to transport lipids out of the liver.

Table 5, shows the blood levels of selected markers, measured before and after six weeks of administering the compositions described herein, to participant no. 2, using the methods described herein.

| Blood Marker | Prior to administration of Claimed Compositions | After twelve weeks of administration of Claimed Compositions |
|---|---|---|
| HbA1c (glycated hemoglobin) | 8.4 | 6.9 |
| Alanine Aminotransferase (Liver Enzyme) | 49 IU/L | 22 IU/L |
| Triglycerides | 243 mg/dL | 179 |
| Total Cholesterol | 170 | 146 mg/dL |
| VLDL (Very Low Density Lipoprotein) | 49 mg/dL | 36 mg/dL |
| C-Reactive Protein | 4.14 mg/dL | 1.94 mg/dL |
| Vitamin D | 29.7 ng/dL | 60 g/dL |

Apart from the blood work results listed above, the participant also experienced quality of life improvements, some of which are outlined in FIG. 1A:

Reduction of Insulin from 30 units daily to 10 units daily. On certain days, no Insulin administration was needed, based on the low blood glucose readings.

Increased energy levels were observed within a week of being on the Life Support regimen, carried out by administration of the composition described herein.

Pain in joints and symptoms of restless legs were reduced within a month of being on the Life Support regimen, carried out by administration of the composition described herein.

A weight loss of 25 lbs. without any exercise, which indicated that the glucose metabolism was returning to homeostasis.

Participant No. 3:

Clinical Background of Participant: The participant suffered from Type II diabetes and was under insulin medication, about six to seven times per day.

The participant was diagnosed to have impairment in the following mechanisms, as a result of hyperglycemia: adrenal gland dysfunction, dysregulation of the HPA axis, evidence suggesting deterioration of hippocampus. Saliva test performed on samples from the participant indicated adrenal stress index which is characterized by excess cortisol production and hippocampal dysfunction.

Formulations described herein were provided to the participant. One or more formulations comprising the following ingredients were administered:

Ashwagandga root: The natural substance has adaptogenic properties, which imparts it with a capability of dealing with adrenal dysfunction at times of high as well as low function. The glucocorticoid activity makes it helpful in adrenal stress syndrome. It also has the ability to counteract some of the adverse physical responses to stress such as changes in blood sugar metabolism.

Holy basil leaf extract: Studies have shown that the holy basil prevents the increased plasma levels of cortisol induced exposure to both chronic and acute stress, supports normal blood sugar levels, modulates HPA activity etc.

*Rhodiola*: It is an adaptogenic plant that has demonstrated Central Nervous system enhancement, anti-depressant properties, anti-carcinogenic properties, and cardioprotective properties.

Pantethine and/or Pantothenic Acid: An important nutrient in stress conditions. It has demonstrated the ability to down regulate the exaggerated secretion of cortisol under times of stress as well as the ability to support adrenal cortical functions when needed.

Phosphatidylserine: Has shown the ability to enhance cellular metabolism and communication, protect cells from oxidative damage, decrease anxiety, improve mood, motivation and depression, enhance memory and cognition, and decrease cortisol. Its activity in decreasing cortisol makes it an important factor in rehabilitating the hippocampus Table 6, shows the blood levels of selected markers, measured before and after six weeks of administering the compositions described herein, to participant no. 4, using the methods described herein.

| Blood Marker | Prior to administration of Claimed Compositions | After eight weeks of administration of Claimed Compositions |
|---|---|---|
| HbA1c (glycated hemoglobin) | 10 | 6.5 |
| Alanine Aminotransferase (Liver Enzyme) | 49 IU/L | 22 IU/L |
| Triglycerides | 199 mg/dL | 169 mg/dL |
| Total Cholesterol | 195 | 143 mg/dL |
| Low Density Lipoprotein (LDL) | 116 mg/dL | 78 mg/dL |

Figure 1B:
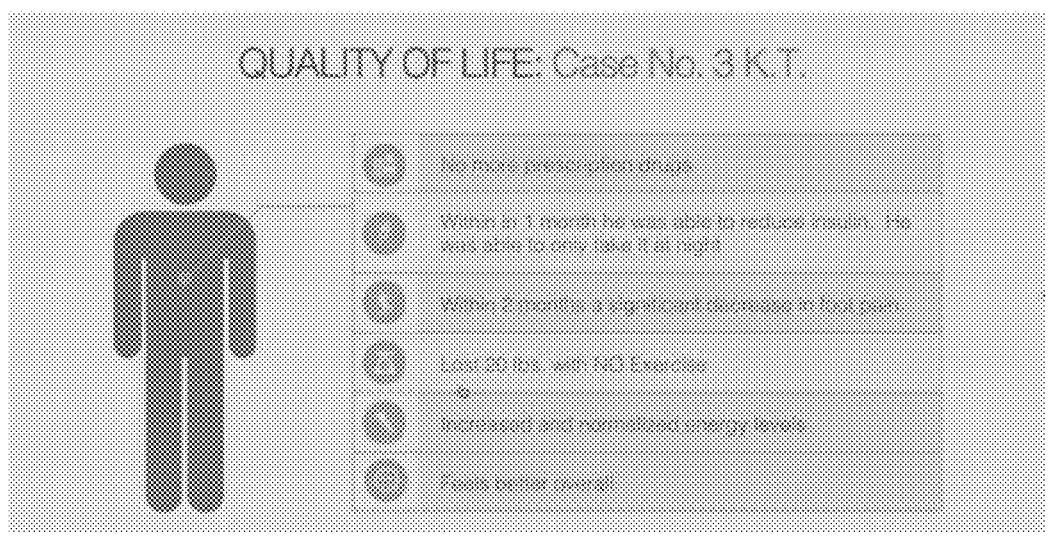

Apart from the blood work results listed above, the participant also experienced the following quality of life improvements, some of which are noted in FIG. 1B:

The patient did not have to continue taking any prescription drugs after two months of being on the regimen.

The insulin dosage was reduced within a month, when the patient needed to take only one insulin dose at night.

There was also significant reduction in foot pain, indicative of amelioration of diabetic neuropathy, within two months.

A total weight loss of 20 lbs, with no exercise, which indicated that the glucose metabolism was returning to homeostasis.

Participant No. 4:

Clinical Background of Participant: The participant suffered from Type II diabetes and presented with very high glucose in hemoglobin levels.

Table 7, shows the blood levels of selected markers, measured before and after six weeks of administering the compositions, to participant no. 4, described herein, using the methods described herein.

| Blood Marker | Prior to administration of Claimed Compositions | After eight weeks of administration of Claimed Compositions |
|---|---|---|
| HbA1c (glycated hemoglobin) | 9.1 | 7.6 |
| Vitamin D | 13.2 ng/dL | 62.7 ng/dL |

Figure 1C:
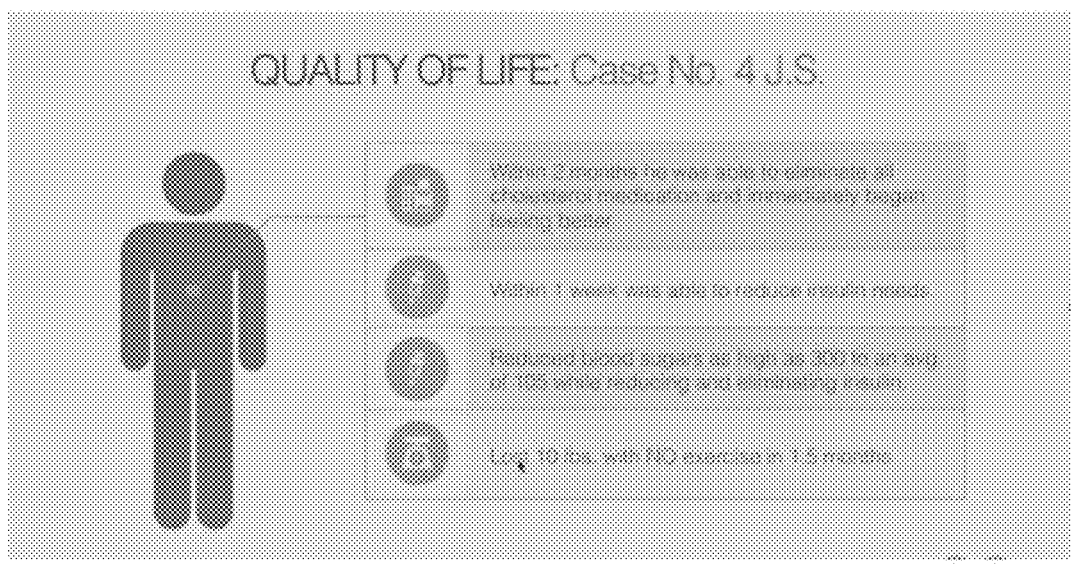

Apart from the blood work results listed above, the participant also experienced the following quality of life improvements, some of which are outlined in FIG. 1C:

The patient was able to eliminate all cholesterol medications within 2 months and began feeling better immediately after starting the regimen.

Insulin needs were reduced within one week.

The blood sugar levels were reduce from 300 mg/dL to an average of 105 mg/dL concurrently with reduction and elimination with the need for Insulin.

A total weight loss of 10 lbs, in one and half months, with no exercise, which indicated that the glucose metabolism was returning to homeostasis.

Participant No. 5:

Table 8, shows the blood levels of selected markers, measured before and after six weeks of administering the compositions described herein, to participant no. 5, using the methods described herein.

| Blood Marker | Prior to administration of Claimed Compositions | After two months of administration of Claimed Compositions |
|---|---|---|
| Glucose | 326 mg/dL | 181 mg/dL |
| HbA1c (glycated hemoglobin) | 14.8 | 10.8 |
| Vitamin D | 13.2 ng/dL | 62.7 ng/dL |
| Triglycerides | 3504 mg/dL | 209 |
| Total Cholesterol | 564 mg/dL | 194 mg/dL |
| LDH (lactic dehydrogenase) | 289 IU/L | 133 |
| GGT (Liver Enzyme) | 78 IU/L | 41 (amelioration of fatty liver pattern) |
| C-Reactive Protein | 6.5 mg/L | 3.42 |
| Glucose in Urine | 3+ | Trace |
| Ketones in Urine | 2+ | Negative |

Participant No. 6:

Clinical Background of Participant: The participant suffered from Type II diabetes and had a heart surgery just before starting a regimen using the compositions described herein. The patient was taking over 300 units on Insulin daily, with no improvement in blood glucose management.

Table 9, shows the blood levels of selected markers, measured before and after six weeks of administering the compositions described herein, to participant no. 6, using the methods described herein.

| Blood Marker | Prior to administration of Life Support Compositions | After eight weeks of administration of Life Support Compositions |
|---|---|---|
| HbA1c (glycated hemoglobin) | 8.4 | 6.3 |
| Aspartate Aminotransferase (Liver Enzyme) | 63 IU/L | 22 U/L |

| Blood Marker | Prior to administration of Life Support Compositions | After eight weeks of administration of Life Support Compositions |
|---|---|---|
| Alanine Aminotransferase (Liver Enzyme) | 79 U/L | 23 U/L |
| Triglycerides | 182 mg/dL | 95 mg/dL |
| Lactic dehydrogenase (LDH) | 289 IU/L | 133 |
| Gamma glutamyl transpeptidase (GGT-Liver Enzyme) | 78 IU/L | 41 (amelioration of fatty liver pattern) |
| C-Reactive Protein | 6.5 mg/L | 3.42 |
| Glucose in Urine | 3+ | Trace |
| Ketones in Urine | 2+ | Negative |

Apart from the blood work results listed above, the participant also experienced the following quality of life improvements:

The patient was able to completely eliminate insulin, lisinopril, cozaar, omeprazole, HCTZ, byetta, and synthroid.

The only medication that the patient had to continue taking was metformin, but only half of the usual dose.

A total weight loss of 150 lbs, in one and half months, with no exercise, which indicated that the glucose metabolism was returning to homeostasis.

Summary of Case Studies:

The Type 2 diabetes patients using formulations, methods and/or kits described herein, prepared using dietary supplements that were carefully constructed to deal with the underlying mechanisms that cause diabetes, were shown to have desirable and positive clinical outcomes.

It is to be understood that the terminology used herein is used for the purpose of describing specific embodiments, and is not intended to limit the scope of the present invention. It should be noted that as used herein, the singular forms of "a", "an" and "the" include plural references unless the context clearly dictates otherwise. In addition, unless defined otherwise, all technical and scientific terms used herein have the same meaning as commonly understood by one of ordinary skill in the art to which this invention belongs.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A dietary supplement in a form selected from the group consisting of a tablet, capsule, pill, emulsion, ointment, lotion, suppository, and aerosol, the dietary supplement consisting essentially of:
   a) a protein selected from the group consisting of pea protein isolate, sacha inchi protein, hemp protein, rice protein, artichoke protein, chia seed protein, beef protein, and combinations thereof;
   b) dandelion extract, milk thistle extract, ginger, taurine, turmeric extract, vitamin C, and methionine;
   c) magnesium, trimethylglycine, glutathione, N-acetyl-cysteine, glutamine, alpha lipoic acid, and glycine;
   d) hesperidin, beet root, enzyme blend, sarsparilla root, bromelain, betaine, methyl sulfonylmethane (MSM), choline bitartarate, primrose, inulin, watercress leaf, *Panax ginseng* root extract, selenium, lecithin, S-anenosylmethionine (SAM-e), thiamine, vitamin B5, niacin, vitamin E, riboflavin, vitamin B6, folate, vitamin B12, biotin, zinc, copper, molybdenum, carotene, vitamin D, sodium phosphate, vitamin A, calcium, phosphorus, chromium, triglyceride, quercetin, rutin, Marshmallow extract, Jerusalem artichoke tuber, fiber, manganese, luo han guo, and *stevia* extract rebaudioside; and
   e) an excipient.

2. The dietary supplement of claim 1, wherein the enzyme blend consists essentially of a lactase, a cellulase, a protease, a lipase, a dismutase, a catalase, or a combination thereof.

3. The dietary supplement of claim 1, wherein the excipient is selected from the group consisting of gelatin, cellulose, medium-chain triglyceride (MCT) oil, silicon dioxide, stearic acid, and combinations thereof.

4. The dietary supplement of claim 1, wherein the dietary supplement is used for supporting glucose level in a subject's blood.

5. The dietary supplement of claim 2, wherein the dietary supplement is used for reducing the need for insulin administration.

6. The dietary supplement of claim 1, wherein the dietary supplement supports, controls, restores, or maintains blood sugar levels in a subject.

7. The dietary supplement of claim 6, wherein the subject has diabetes or complications associated with diabetes.

8. The dietary supplement of claim 6, wherein the subject has type II diabetes.

9. The dietary supplement of claim 6, wherein the subject has type I diabetes.

10. The dietary supplement of claim 6, wherein the subject has skin complications, eye complications, foot complications, heart diseases, or inflammation.

11. The dietary supplement of claim 6, wherein the subject has neuropathy, diabetic ketoacidosis, kidney disease, hypertension, gastroparesis, or high cholesterol.

12. The dietary supplement of claim 6, wherein the subject has pre-diabetes.

* * * * *